United States Patent
Lundqvist et al.

(10) Patent No.: US 10,975,046 B2
(45) Date of Patent: Apr. 13, 2021

(54) CRYSTAL MODIFICATIONS OF ODEVIXIBAT

(71) Applicant: Albireo AB, Göteborg (SE)

(72) Inventors: Robert Lundqvist, Hälsö (SE); Ingvar Ymen, Saltsjö-Boo (SE); Martin Bohlin, Johanneshov (SE); Eva Byröd, Mölndal (SE); Per-Göran Gillberg, Mölndal (SE); Anna-Maria Tivert, Gothenburg (SE); Rikard Bryland, Limhamn (SE); Ann-Charlotte Dahlquist, Lund (SE); Jessica Elversson, Dalby (SE); Nils Ove Gustafsson, Löddeköpinge (SE)

(73) Assignee: Albireo AB, Gothenburg (SE)

( * ) Notice: Subject to any disclaimer, the term of this patent is extended or adjusted under 35 U.S.C. 154(b) by 0 days.

(21) Appl. No.: 16/508,036

(22) Filed: Jul. 10, 2019

(65) Prior Publication Data

US 2020/0002299 A1 Jan. 2, 2020

Related U.S. Application Data

(63) Continuation of application No. PCT/SE2019/050602, filed on Jun. 20, 2019.

(30) Foreign Application Priority Data

Jun. 20, 2018 (SE) .................................... 1850761-6
Jun. 20, 2018 (SE) .................................... 1850762-4

(51) Int. Cl.
*A61K 31/551* (2006.01)
*A61P 1/16* (2006.01)
*C07D 285/36* (2006.01)

(52) U.S. Cl.
CPC ........ *C07D 285/36* (2013.01); *C07B 2200/13* (2013.01)

(58) Field of Classification Search
CPC ........ A61K 31/554; A61P 1/16; C07D 285/36
See application file for complete search history.

(56) References Cited

U.S. PATENT DOCUMENTS

| | | | |
|---|---|---|---|
| 3,539,380 A | 11/1970 | Johnson | |
| 4,172,120 A | 10/1979 | Todd et al. | |
| 4,507,235 A | 3/1985 | Wunsch | |
| 5,167,965 A | 12/1992 | Schulz | |
| 5,294,448 A | 3/1994 | Ring | |
| 5,350,584 A | 9/1994 | McClelland et al. | |
| 5,422,124 A | 6/1995 | Valducci | |
| 5,578,316 A | 11/1996 | Bhardwaj et al. | |
| 5,663,165 A | 9/1997 | Brieaddy | |
| 5,681,584 A | 10/1997 | Savastano | |
| 5,723,458 A | 3/1998 | Brieaddy et al. | |
| 5,811,388 A | 9/1998 | Friend et al. | |
| 5,817,652 A | 10/1998 | Brieaddy et al. | |
| 5,900,233 A | 5/1999 | Day | |
| 5,910,494 A | 6/1999 | Brieaddy | |
| 5,976,811 A | 11/1999 | Mullner et al. | |
| 5,994,391 A | 11/1999 | Lee et al. | |
| 5,998,400 A | 12/1999 | Brieaddy et al. | |
| 6,020,330 A | 2/2000 | Enhsen et al. | |
| 6,069,167 A | 5/2000 | Sokol | |
| 6,277,831 B1 | 8/2001 | Frick et al. | |
| 6,346,527 B1 | 2/2002 | Takanaka et al. | |
| 6,355,672 B1 | 3/2002 | Yasuma et al. | |
| 6,387,924 B2 | 5/2002 | Lee et al. | |
| 6,387,944 B1 | 5/2002 | Frick et al. | |
| 6,426,340 B1 | 7/2002 | Gibson et al. | |
| 6,562,860 B1 | 5/2003 | Keller et al. | |
| 6,592,900 B1 | 7/2003 | Buhler | |
| 6,635,280 B2 | 10/2003 | Shell et al. | |
| 6,642,269 B2 | 11/2003 | Frick et al. | |
| 6,676,979 B2 | 1/2004 | Marlett et al. | |
| 6,784,201 B2 | 8/2004 | Lee et al. | |
| 6,906,058 B2 | 6/2005 | Starke et al. | |
| 6,943,189 B2 | 9/2005 | Keller et al. | |
| 7,019,023 B2 | 3/2006 | Frick et al. | |
| 7,125,864 B2 | 10/2006 | Starke et al. | |
| 7,132,416 B2 | 11/2006 | Starke et al. | |

(Continued)

FOREIGN PATENT DOCUMENTS

| | | |
|---|---|---|
| CA | 20651511 | 3/1991 |
| DE | 3930168 | 3/1991 |

(Continued)

OTHER PUBLICATIONS

"A Long-Term, Open-Label Study of LUM001 With a Double-Blind, Placebo Controlled, Randomized Drug Withdrawal Period to Evaluate Safety and. Efficacy in Children With Alagille Syndrome (ICONIC)," Clinical Trials.gov, Jun. 9, 2014, retrieved Oct. 3, 2014, http://clinicaltrials.gov/ct2/show;NCT02160782?term=LUM001&rank=7, 4 pages.

"Alagile Syndrome " Wikipedia, the free encyclopedia, posted on or about Feb. 11, 2005, retrieved Feb. 12, 2014, http://en.wikipedia.org/wiki/Alagille_syndrome, 3 pages.

"Albireo's Lead Compound in Cholestatic Liver Diseases, A4250, Projects Against Bile Acid-Mediated Cholestatic Liver Injury in Mice," Albireo Press Release, Apr. 11, 2014, 2 pages.

(Continued)

*Primary Examiner* — Brenda L Coleman
(74) *Attorney, Agent, or Firm* — Fish & Richardson P.C.

(57) ABSTRACT

The present invention relates to crystal modifications of 1,1-dioxo-3,3-dibutyl-5-phenyl-7-methylthio-8-(N—{(R)-α-[N—((S)-1-carboxypropyl)carbamoyl]-4-hydroxybenzyl}carbamoylmethoxy)-2,3,4,5-tetrahydro-1,2,5-benzothiadiazepine (odevixibat), more specifically crystal modifications 1 and 2 of odevixibat. The invention also relates to a process for the preparation of crystal modification 1 of odevixibat, to a pharmaceutical composition comprising crystal modification 1, and to the use of this crystal modification in the treatment of various conditions as described herein.

20 Claims, 16 Drawing Sheets

Specification includes a Sequence Listing.

(56) References Cited

U.S. PATENT DOCUMENTS

| | | |
|---|---|---|
| 7,132,557 B2 | 11/2006 | Wilkes et al. |
| 7,192,945 B2 | 3/2007 | Starke et al. |
| 7,192,946 B2 | 3/2007 | Starke et al. |
| 7,192,947 B2 | 3/2007 | Starke et al. |
| 7,226,943 B2 | 6/2007 | Starke et al. |
| 7,238,684 B2 | 7/2007 | Starke et al. |
| 7,514,421 B2 | 4/2009 | Abrahamsson et al. |
| 7,615,536 B2 | 11/2009 | Frick et al. |
| 7,767,229 B1 | 8/2010 | Milne et al. |
| 7,923,468 B2 | 4/2011 | Frick et al. |
| 7,939,061 B2 | 5/2011 | Prakash et al. |
| 7,956,085 B2 | 6/2011 | Frick et al. |
| 8,048,413 B2 | 11/2011 | Huguet |
| 8,067,584 B2 | 11/2011 | Starke et al. |
| 8,101,583 B2 | 1/2012 | Glombik et al. |
| 8,106,023 B2 | 1/2012 | Glombik et al. |
| 9,023,368 B2 | 5/2015 | Basit et al. |
| 9,295,677 B2 | 3/2016 | Ling et al. |
| 9,339,480 B2 | 5/2016 | Young et al. |
| 9,409,875 B2 | 8/2016 | Bohlin et al. |
| 9,684,018 B2 | 6/2017 | Horanzy |
| 9,694,018 B1 | 7/2017 | Gillberg et al. |
| 9,701,649 B2 | 7/2017 | Bohlin et al. |
| 9,745,276 B2 | 8/2017 | Bohlin et al. |
| 9,872,844 B2 | 1/2018 | Zemel et al. |
| 2002/0054903 A1 | 5/2002 | Tyler et al. |
| 2002/0142054 A1 | 10/2002 | Marlett et al. |
| 2003/0124088 A1 | 7/2003 | Masuda et al. |
| 2003/0125316 A1 | 7/2003 | Keller et al. |
| 2003/0143183 A1 | 7/2003 | Knudsen et al. |
| 2003/0153541 A1 | 8/2003 | Dudley et al. |
| 2003/0166927 A1 | 9/2003 | Starke et al. |
| 2003/0199515 A1 | 10/2003 | Mudipalli et al. |
| 2003/0215843 A1 | 11/2003 | Poupon et al. |
| 2004/0014806 A1 | 1/2004 | Bhat et al. |
| 2004/0038862 A1 | 2/2004 | Goodwin et al. |
| 2004/0062745 A1 | 4/2004 | Green et al. |
| 2004/0067933 A1 | 4/2004 | Starke et al. |
| 2004/0077625 A1 | 4/2004 | Tremont et al. |
| 2004/0082647 A1 | 4/2004 | Babiak et al. |
| 2004/0176438 A1 | 9/2004 | Tremont et al. |
| 2005/0009805 A1 | 1/2005 | Sasahara et al. |
| 2005/0089572 A1 | 4/2005 | Kumar |
| 2005/0113362 A1 | 5/2005 | Lindstedt et al. |
| 2005/0118326 A1 | 6/2005 | Anfinsen |
| 2005/0124557 A1 | 6/2005 | Lindqvist |
| 2005/0171204 A1 | 8/2005 | Lindstedt et al. |
| 2005/0197376 A1 | 9/2005 | Kayakiri et al. |
| 2005/0215882 A1 | 9/2005 | Chenevert et al. |
| 2005/0266080 A1 | 12/2005 | Desai et al. |
| 2005/0282822 A1 | 12/2005 | Alstermark et al. |
| 2006/0083790 A1 | 4/2006 | Anderberg et al. |
| 2006/0210631 A1 | 9/2006 | Patel |
| 2006/0210633 A1 | 9/2006 | Dharmadhikari |
| 2007/0197522 A1 | 8/2007 | Edwards et al. |
| 2007/0237818 A1 | 10/2007 | Malcom et al. |
| 2008/0193543 A1 | 8/2008 | Morello |
| 2008/0207592 A1 | 8/2008 | Frick et al. |
| 2008/0300171 A1 | 12/2008 | Balkan et al. |
| 2009/0098200 A1 | 4/2009 | Temtsin Krayz et al. |
| 2009/0131395 A1 | 5/2009 | Antonelli et al. |
| 2010/0130472 A1 | 5/2010 | Young et al. |
| 2010/0286122 A1 | 11/2010 | Belyk |
| 2011/0003782 A1 | 1/2011 | Pellicciari |
| 2011/0152204 A1 | 6/2011 | Gedulin et al. |
| 2011/0159087 A1 | 6/2011 | Sathe et al. |
| 2011/0294767 A1 | 12/2011 | Gedulin et al. |
| 2012/0114588 A1 | 5/2012 | Starke et al. |
| 2012/0157399 A1 | 6/2012 | Young et al. |
| 2013/0029938 A1 | 1/2013 | Aquino et al. |
| 2013/0052269 A1 | 2/2013 | Lescure |
| 2013/0059807 A1 | 3/2013 | Gedulin et al. |
| 2013/0108573 A1 | 5/2013 | Gedulin et al. |
| 2013/0109671 A1 | 5/2013 | Gedulin et al. |
| 2013/0225511 A1 | 8/2013 | Gillberg et al. |
| 2013/0236541 A1 | 9/2013 | Gillberg et al. |
| 2015/0031636 A1 | 1/2015 | Gillberg et al. |
| 2015/0031637 A1 | 1/2015 | Gillberg et al. |
| 2016/0039777 A1 | 2/2016 | Bohlin et al. |
| 2016/0146715 A1 | 5/2016 | Shim et al. |
| 2016/0193277 A1 | 7/2016 | Gillberg et al. |
| 2016/0194353 A1 | 7/2016 | Gillberg et al. |
| 2016/0229822 A1 | 8/2016 | Bohlin |
| 2016/0237049 A1 | 8/2016 | Bohlin |
| 2017/0143738 A1 | 5/2017 | Ando et al. |
| 2017/0143783 A1 | 5/2017 | Ando et al. |
| 2017/0182115 A1 | 6/2017 | Gillberg et al. |
| 2017/0224719 A1 | 8/2017 | Gillberg et al. |
| 2017/0224720 A1 | 8/2017 | Gillberg et al. |
| 2017/0224721 A1 | 8/2017 | Gillberg et al. |
| 2017/0240516 A1 | 8/2017 | Ymen et al. |
| 2018/0022776 A1 | 1/2018 | Gillberg et al. |
| 2018/0030088 A1 | 2/2018 | Gillberg et al. |
| 2018/0030089 A1 | 2/2018 | Gillberg et al. |
| 2018/0140219 A1 | 5/2018 | Yin et al. |
| 2018/0030009 A1 | 6/2018 | Gillberg et al. |
| 2018/0264029 A1 | 9/2018 | Gillberg et al. |
| 2018/0264030 A1 | 9/2018 | Gillberg et al. |
| 2018/0264031 A1 | 9/2018 | Gillberg et al. |
| 2018/0360869 A1 | 12/2018 | Gillberg et al. |
| 2018/0360870 A1 | 12/2018 | Gillberg et al. |
| 2018/0360871 A1 | 12/2018 | Gillberg et al. |
| 2018/0362577 A1 | 12/2018 | Gillberg et al. |
| 2019/0046451 A1 | 2/2019 | Gillberg et al. |
| 2019/0070217 A1 | 3/2019 | Gillberg et al. |
| 2019/0177286 A1 | 6/2019 | Ymen et al. |
| 2019/0367467 A1 | 12/2019 | Gillberg et al. |
| 2020/0046635 A1 | 2/2020 | Gillberg et al. |
| 2020/0046636 A1 | 2/2020 | Gillberg et al. |
| 2020/0046757 A1 | 2/2020 | Gillberg et al. |
| 2020/0046758 A1 | 2/2020 | Gillberg et al. |
| 2020/0049611 A1 | 2/2020 | Gillberg et al. |
| 2020/0140484 A1 | 5/2020 | Gillberg et al. |

FOREIGN PATENT DOCUMENTS

| | | |
|---|---|---|
| DE | 19825804 | 8/2000 |
| EP | 0278464 | 8/1988 |
| EP | 0489423 | 12/1991 |
| EP | 0372542 | 10/1992 |
| EP | 0573848 | 5/1993 |
| EP | 0549967 | 7/1993 |
| EP | 0624593 | 11/1994 |
| EP | 0624594 | 11/1994 |
| EP | 0624595 | 11/1994 |
| EP | 0624596 | 11/1994 |
| EP | 0864582 | 11/1994 |
| EP | 0594570 | 7/1995 |
| EP | 1173205 | 4/2000 |
| EP | 1273307 | 1/2003 |
| EP | 1535913 | 6/2005 |
| EP | 1719768 | 6/2005 |
| EP | 2144599 | 2/2008 |
| EP | 3210977 | 8/2017 |
| GB | 1573487 | 8/1980 |
| GB | 2262888 | 7/1996 |
| JP | 2000-513028 | 10/2000 |
| JP | A-2004-516285 | 6/2004 |
| JP | B-3665055 | 6/2005 |
| JP | 2006/124695 | 5/2006 |
| JP | 2013-541584 | 11/2013 |
| JP | A-2013-542953 | 11/2013 |
| JP | H02258719 | 10/2019 |
| WO | WO 1993/16055 | 8/1993 |
| WO | WO 1994/00111 | 1/1994 |
| WO | WO 1994/18183 | 8/1994 |
| WO | WO 1994/18184 | 8/1994 |
| WO | WO 1996/05188 | 2/1996 |
| WO | WO 1996/08484 | 3/1996 |
| WO | WO 1996/16051 | 5/1996 |
| WO | WO 1997/33882 | 9/1997 |
| WO | WO 1998/03818 | 1/1998 |
| WO | WO 1998/07449 | 1/1998 |
| WO | WO 1998/38182 | 9/1998 |

(56) References Cited

FOREIGN PATENT DOCUMENTS

| | | |
|---|---|---|
| WO | WO 1998/40375 | 9/1998 |
| WO | WO 1998/56757 | 12/1998 |
| WO | WO 1999/01149 | 1/1999 |
| WO | WO 1999/32478 | 7/1999 |
| WO | WO 1999/35135 | 7/1999 |
| WO | WO 1999/64409 | 7/1999 |
| WO | WO 1999/64410 | 12/1999 |
| WO | WO 2000/01687 | 1/2000 |
| WO | WO 2000/38725 | 7/2000 |
| WO | WO 2000/38726 | 7/2000 |
| WO | WO 2000/38727 | 7/2000 |
| WO | WO 2000/38728 | 7/2000 |
| WO | WO 2000/38729 | 7/2000 |
| WO | WO 2000/47568 | 8/2000 |
| WO | WO 2000/61568 | 10/2000 |
| WO | WO 2000/62810 | 10/2000 |
| WO | WO 2001/34570 | 5/2001 |
| WO | WO 2001/60807 | 8/2001 |
| WO | WO 2001/66533 | 9/2001 |
| WO | WO 2001/68096 | 9/2001 |
| WO | WO 2001/68637 | 9/2001 |
| WO | WO 2002/08211 | 1/2002 |
| WO | WO 2002/09815 | 4/2002 |
| WO | WO 2002/32428 | 4/2002 |
| WO | WO 2002/50051 | 6/2002 |
| WO | WO 2002/53548 | 6/2002 |
| WO | WO 2003/020710 | 3/2003 |
| WO | WO 2003/022286 | 3/2003 |
| WO | WO 2003/022804 | 3/2003 |
| WO | WO 2003/022825 | 3/2003 |
| WO | WO 2003/022830 | 3/2003 |
| WO | WO 2003/043992 | 5/2003 |
| WO | WO 2003/051821 | 6/2003 |
| WO | WO 2003/051822 | 6/2003 |
| WO | WO 2003/061663 | 7/2003 |
| WO | WO 2003/091232 | 11/2003 |
| WO | WO 2003/106482 | 12/2003 |
| WO | WO 2004/006899 | 1/2004 |
| WO | WO 2004/056748 | 7/2004 |
| WO | WO 2004/076430 | 7/2004 |
| WO | WO 2004/020421 | 10/2004 |
| WO | WO 2004/089350 | 10/2004 |
| WO | WO 1991/03249 | 6/2005 |
| WO | WO 2005/082874 | 9/2005 |
| WO | WO 2007/009655 | 1/2007 |
| WO | WO 2007/009656 | 1/2007 |
| WO | WO 2008/058628 | 5/2008 |
| WO | WO 2008/058630 | 5/2008 |
| WO | WO 2008/058631 | 5/2008 |
| WO | WO 2010/062861 | 6/2010 |
| WO | WO 2010/041268 | 9/2010 |
| WO | WO 2011/137135 | 11/2011 |
| WO | WO 2011/150286 | 12/2011 |
| WO | WO 2012/064267 | 5/2012 |
| WO | WO 2012/064268 | 5/2012 |
| WO | WO 2013/063512 | 5/2013 |
| WO | WO 2013/063526 | 5/2013 |
| WO | WO 2014/174066 | 10/2014 |
| WO | WO 2015/193788 | 12/2015 |
| WO | WO 2017/138876 | 8/2017 |
| WO | WO 2017/138877 | 8/2017 |
| WO | WO 2017/138878 | 8/2017 |
| WO | WO 2019/032026 | 2/2019 |
| WO | WO 2019/032027 | 2/2019 |

OTHER PUBLICATIONS

"An Extension Study to Evaluate the Long-Tern Safety and Durability of Effect of LUM001 in the Treatment of Cholestatic Liver Disease in Subjects With Alagille Syndrome (IMAGINE)," Clinical Trials.gov, Jan. 23, 2014, retrieved on Oct. 3, 2014, http://clinicaltrials.gov/ct2/show/NCT02047318?term=LUM001&rank=3, 3 pages.

"Art Extension Study to Evaluate the Long-Term Safety and Durability of Effect of LUM001 in the Treatment of Cholestatic Liver Disease in Subjects With Alagille Syndrome (IMAGINE-II)," Clincal Trials.gov, Apr. 16, 2014, retrieved on Oct. 3, 2014, http://clinicaltrials.gov/ct2/show/NCT02117713?term=LUM001&rank=2, 3 pages.

"Bowel Diversion Surgeries: Ileostomy, Colostomy, Ileoanal Reservoir and Continent Ileostomy," US Department of Health and Human Services: National Institute of Diabetes and Digestive and Kidney Diseases, Feb. 2009, retrieved on Jan. 27, 2014, http://digestive.niddk.nih.gov/ddiseases/pub/ileostomy/Bowel_Diversion_508.pdf, 4 pages.

"EASL Clinical Practice Guidelines: Management of cholestatic liver diseases," European Assoc. for the Study of the Liver, Journal of Hepatology, 2009, 51:237-267.

"Evaluation of LUM001 in the Reduction of Pruritus in Alagille Syndrome (ITCH)," Clinical Trials.gov, Feb. 5, 2014, retrieved on Oct. 3, 2014, hap://clinicaltrials.gov/ct2/show/NCT02057692?term=LUM001&rank=5, 4 pages.

"IBAT inhibitor A4250 for Cholestatic Pruritus," ClinicalTrials.gov, Last updated Feb. 10, 2015, https://clinicaltrials.gov/ct2/show/NCT02360852?term=a4250&rank=1, 3 pages.

"Initiation of a Phase II Trial for A4250, the Company's Lead Compound for Cholestatic Liver Diseases and NASH," Alhireo Pharma Press Release, Feb. 5. 2015, http://www.alberiopharma.com/News.aspx?PageID=1600872, 2 pages.

"Lamella Pharmaceuticals Now Dosing Patients in the INDIGO Phase 2 Clinical Trial of LUM001 in Pediatric Patients with Progressive Familial Intrahepatic Cholestasis," PR Newswire, May 9, 2014, retrieved on Oct. 3, 2014, http://www.prnewswire.com/news-releases/lumena-pharmaceuticals-now-dosing-patients-in-the-indigo-phase-2-clinical-trial-of-lum001-in-pediatric-patients-with-progressive-familial-intrahepatic-cholestasis-258609691.html, 3 pages.

"Open Label Study to Evaluate Efficacy and Long Term Safety of LUM001 in the Treatment of Cholestatic Liver Disease in Patients With Progressive Familial Intrahepatic Cholestasis (INDIGO)," Clinical Trials.gov, Feb. 5, 2014, retrieved on Oct. 3, 2014, http://clinicaltrials.gov/ct2/show/NCT02057718?term=LUM001&rank-4, 3 pages.

"Open Label Study to Evaluate Safety and Efficacy of LUM001 in Patients With Primary Sclerosing Cholangitis (CAMEO)," Clinical Trials.gov, Feb. 11, 2014, retrieved Oct. 3, 2014, http://clinicaltrials.gov/ct2/show/NCT02061540?term=LUM001&rank=6, 3 pages.

"Phase 2 Study to Evaluate LUM001 in Combination With Ursodeoxycholic Acid in Patients With Primary Biliary Cirrhosis (CLARITY)," Clinical Trials.gov, Jul. 17, 2013, retrieved Oct. 3, 2014, http://clinicaltrials.gov/ct2/show/NCT01904058?term=LUM001&rank-8, 3 pages.

"Progressive familial intrahepatic cholestasis," Wikipedia, the free encyclopedia, posted on or about Feb. 24, 2006, http://en.wikipedia.org/wiki/Progressive_familial_intrahepatic_cholestasis, 3 pages.

"Safety and Efficacy Study of LUM001 in the Treatment of Cholestatic Liver Disease in Patients With Alagille Syndrome (IMAGO)," Clinical Trials.gov, Jul. 16, 2013, http://clinicaltrials.gov/ct2/show/NCT01903460?term=LUM001&rank=1, 3 pages.

"What is Alagille Syndrome?," European Medicines Agency, Jan. 21, 2014, retrieved on Oct. 3, 2014. http://www.ema.europa.eu/docs/en_GB/document_library/Orphan_designation/2014/01/WC500159874.pdf, 6 pages.

AASLD: 2017 68th Annual Meeting of the American Association for the Study of Liver Diseases, Washington, DC, Oct. 20-24, 2017, (Abstract only).

Adams et al., "Hepascore: an accurate validated predictor of liver fibrosis in chronic hepatitis C infection," Clin. Chem. 2005, vol. 51(10), p. 1867-1873.

Alashkar et al., "Meeting Info: 57th Annual Meeting of the American Society-of-Hematology," Orlando, FL, USA. Dec. 5-8, 2015, Amer Soc Hematol, Blood, 2015, 126(23).

Alissa et al., "Invited Review: Update on Progressive Familial Intrahepatic Cholestasis," Journal of Pediatric Gastroenterology and Nutrition, 2008, 46:241-252.

Alonso et al., "Histologic pathology of the liver in progressive familial intrahepatic cholestasis," Journal of Pediatric Gastroenterology and Nutrition, 14: 128-133, 1994.

(56) References Cited

OTHER PUBLICATIONS

Alvarez et al., "Reduced hepatic expression of farnesoid X receptor in hereditaly cholestasis associated to mutation in ATP891," Hum Mol Genet, 2004, 13(20):2451-2460.
Alvarez, Fernando; "Treatments in chronic cholestasis in children." Ann. Nestlé (2008) 66 p. 127-135.
American Diabetes Association, "Management of Dyslipidemia in Adults with Diabetes," Diabetes Care, Jan. 2003, 26(1).
Anakk et al., "Bile acids activate YAP to promote liver carcinogenesis," Cell Rep., Nov. 27, 2013, 5(4):1060-1069.
Angulo et al., "Independent Predictors of Liver Fibrosis in Patients With Nonalcoholic Steatohepatitis," Hepatology, Dec. 1999, 30(6): 1356-1362.
Angulo et al., "The NAELD fibrosis score: a noninvasive system that identifies liver fibrosis in patients with NAFLD," Hepatology, 2007, vol. 45(4), p. 846-54.
Angulo, "Use of ursodeoxycholic acid in patients with liver disease," Current Gastroenterology Reports, Feb. 1, 2002, 4(1):37-44.
Anzivino et al., "ABCB4 and ABCB11 mutations in intrahepatic cholestasis of pregnancy in an Italian population." Dig Liver Dis., 2013. 45(3):226-232.
Appleby et al., "Effects of conventional and a novel colonic-release bile acid sequestrant, A3384, on fibroblast growth factor 19 and bile acid metabolism in healthy volunteers and patients with bile acid diarrhoea", United Eur. Gastroent. J., vol. 5, pp. 380-388, 2017.
Arnell et al., "Follow-up in children with progressive familial intrahepatic cholestasis after partial external biliary diversion," J Pediatr Gastroenterol Nutr., 2010, 51(4):494-499.
Artursson and Karlsson, "Correlation Between Oral Drug Absorption in Humans and Apparent Drug Permeability Coefficients in Human Intestinal Epithelial (CACO-2) Cells," Biochemical and Biophysical Research Communications, Mar. 1991, 175(3):880-885.
Attili et al., "Bile Acid-induced Liver Toxicity: Relation to the Hydrophobic-Hydrophilic Balance of Bile Acids," Medical Hypotheses, 1986, 19:57-69.
Baghdasaryan et al., "Inhibition of intestinal bile acid absorption by ASBT inhibitor A4250 protects against bile acid-mediated cholestatic liver injury in mice," J. Hepatology, 2014, 60:S57.
Baghdasaryan et al., "Inhibition of intestinal bile acid absorption by ASBT inhibitor A4250 protects against bile acid-mediated cholestatic liver injury in mice," Presented at the EASL Conference, London, UK, Apr. 12, 2015, http://www.albireopharma.com/News.aspx?PageID=1591817, 22 pages.
Bajor et al., "Bile acids: short and long term effects in the intestine," Scandinavian J. Gastro., 2010, 45:645-664.
Balbach et al., "Pharmaceutical evaluation of early development candidates "The 100 mg-approach"," Int J Pharm, May 4, 2004, 275(1):1-12.
Banker et al., "Modern Pharmaceutics, 3ed.", Marcel Dekker, New York, 1996, pp. 451 and 596.
Baumann, U. et al., "The ileal bile acid transport inhibitor A4250 decreases pruritus and serum bile acids in cholestatic liver diseases—an ongoing multiple dose, open-label, multicenter study," Hepatology, 2017, 66(1): S91 (Abstract only).
Ravin, "Polymorphism in Process Development," Chemistry and industry, 527-529, 1989.
Beausejour et al., "Description of two new ABCB11 mutations responsible for type 2 benign recurrent intrahepatic cholestasis in a French-Canadian family," Can J Gastroenterol., 2011, 25(6):311-314.
Beraza et al., Nor-ursodeoxycholic acid reverses hepatocyte-specific nemo-dependant steatohepatitis. Gut, 2011: 60: 387-396.
Bhaskaran et al., "Extrusion Spheronization—A Review," International Journal of PharnnTech Research. vol. 2, No. 4, pp. 2429-2433, Oct.-Dec. 2010 (Year: 2010).
Billington et al., "Effects of bile salts on the plasma membranes of isolated rat hepatocytes," Bichem. J. 188: 321-327, 1980.

Blackmore et al., "Polymorphisms in ABCB11 and ATP8B1 Associated with Development of Severe Intrahepatic Cholestasis in Hodgkin's Lymphoma," J Clin Exp Hepatol., 2013, 3(2):159-161.
Board of Appeal of European Patent Office, Case No. T 077/08-3.3.01, dated May 24, 2011, 17 pages.
Bonge et al., "Cytostar-T Scintillating Microplate Assay for Measurement of Sodium-Dependent Bile Acid Uptake in Transfected HEK-293 Cells," Analytical Biochemistry, 2000, 282:94-101.
Bounford. University of Birmingham. Dissertation Abstracts International, (2016) vol. 75, No. 1C. Order No. AA110588329. ProQuest Dissertations & Theses.
Brunt et al., "Nonalcoholic Steatohepatitis: A Proposal for Grading and Staging the Histological Lesions," American Journal of Gastroenterology, Sep. 1999, 94(9): 2467-2474.
Brunzell and Hokanson, "Dislipidemia of Central Obesity and Insulin Resistance," Diabetes Care, 1999, 22(Suppl. 3):C10-C13.
Bull et al., "Genetic and morphological findings in progressive familial intrahepatic cholestasis (Byler disease [PFIC-1] and Byler syndrome): Evidence for Heterogeneity," Hepatology, 26: 1, 155-164, 1997.
Burrows, "Interventions for treating cholestasis in pregnancy," Cochrane Database Syst. Rev., 4:CD00493, 2001.
Byrn et al., "Pharmaceutical Solids: A Strategic Approach to Regulatory Considerations," Pharmaceutical Research, 1995, 12(7), pp. 945-954.
Byrne et al., "Missense mutations and single nucleotide polymorphisms in ABCB11 impair bile salt export pump processing and function or disrupt pre-messenger RNA splicing," Hepatology., 2009, 49(2):553-567.
Caira, "Crystalline Polymorphism of Organic Compounds," in: Topics in Current Chemistry, Jan. 1998, 198:163-208.
Camilleri, "Probiotics and irritable bowel syndrome: rationale, putative mechanisms, and evidence of clinical efficacy," Clin. Gastroenterol., 40(3):264-9, Mar. 2006.
Carulli et al, "Review article: effect of bile salt pool composition on hepatic and biliary functions," Aliment. Pharmacol. Ther. 2000, vol. 14. suppl. 2, p. 14-18.
Centeno, "Molecular mechanisms triggered by low-calcium diets," Nutrition research reviews., 22(2):163-74, Dec. 2009.
Chalasani et al., "The diagnosis and management of nonalcoholic fatty liver disease: Practice guidance from the American Association for the Study of Liver Diseases," Hepatology, 2018, 67(1):328-357.
Chen et al., "Bile salt export pump is dysregulated with altered farnesoid X receptor isoform expression inpatients with hepatocellular carcinoma," Hepatology, 57: 4, 1530-1541, 2013.
Chen et al., "Diagnosis of BSEP/ABCB11 mutations in Asian patients with cholestasis using denaturing high performance liquid chromatography," J Pediatr., 2008, 153(6):825-832.
Chen et al., "FIC1 and BSEP defects in Taiwanese patients with chronic intrahepatic cholestasis with low gamma-glutamyltranspeptidase levels," Journal of Pediatrics, 2002, 140(1):119-124.
Chen et al., "Inhibition of apical sodium-dependent bile acid transporter as a novel treatment for diabetes," Am J Physiol Endocrinol Metab, 2012, 302:E68-E76.
Chen et al., "Progressive Familial Intrahepatic Cholestasis, Type 1, Is Associated with Decreased Farnesoid X Receptor Activity," Gastroenterology, 2004, 126:756-764.
Chen et al., "Serum and urine metabolite profiling reveals potential biomarkers of human hepatocellular carcinoma," Molecular and Cellular Ptolemies 10.7, 2011.
Chen et al., "The effects of diets enriched in beta-glucans on blood lipoprotein concentrations," J. Clin. Lipidol., 3(3):154-8, May 2009.
Chen et al., "Treatment effect of rifampicin on cholestasis," Internet Journal of Pharmacology, 4(2), 2006.
Chey et al., "A Randomized Placebo-Controlled Phase II b Trial of A3309, a Bile Acid Transporter Inhibitor, for Chronic Idiopathic Constipation," Am. J. Gastroenterology, May 2011, 106:1803-1812.
Chiang, "Bile acids: regulation of synthesis," J. Lipid Res, 2009, 50(10):1955-1966.
Chourasia et al., "Polysaccharides for colon targeted drug delivery," Drug Delivery, Academic Press, vol. 11, No. 2, Jan. 1, 2004, 129-148, XP008060983.

(56) References Cited

OTHER PUBLICATIONS

Copeland et al., "Novel splice-site mutation in ATP8B1 results in atypical progressive familial intrahepatic cholestasis type 1," J Gastroenterol Hepatol., 2013, 28(3):560-564.
Danese et al., "Analytical evaluation of three enzymatic assays for measuring total bile acids in plasma using a fully-automated clinical chemistry platform," PLoS One, 2017, 12(6):e0179200.
Das & Kar., Nonalcoholic steatohepatitis. JAPI. 53:, Mar. 2005.
Dashti et al., "A Phospholipidomic Analysis of All Defined Human Plasma Lipoproteins," Nature.com: Scientific Reports, Nov. 2011, DOI: 10.1038, 11 pages.
Davit_Spraul et al., "ATP8B1 and ABCB11 Analysis in 62 Children with Normal Gamma-Glutamyl Transferase Progressive Familial Intrahepatic Cholestasis (PFIC): Phenotypic Differences Between (PFIC): and PFIC2 and Natural History," Hepatology: Autoimmune, Cholestatic and Biliary Disease, May 2010, 1645-1655.
Davit-Spraul et al., "Liver transcript analysis reveals aberrant splicing due to silent and intronic variations in the ABCB11 gene," Mol Genet Metab., 2014, 113(3):225-229.
Davit-Spraul et al., "Progressive familial intrahepatic cholestasis," Orphanet Journal of Rare Diseases, Jan. 2009, 4:1-12.
Dawson et al., "Bile acid transporters" J. Lipid Res. 2009, 50, 2340-2357.
Dawson, "Role of the intestinal bile acid transporters in bile acid and drug disposition," Handb. Exp. Pharmacol. 2011, 201:169-203.
De Lédinghen et al., "Controlled attenuation parameter for the diagnosis of steatosis in non-alcoholic fatty liver disease," J Gastroenterol Hepatol., 2016, 31(4):848-855.
DeFronzo et al., "Insulin resistance, a multi-surfaced syndrome responsible for NIDDM, obesity, hypertension, dyslipidemia and atherosclerotic cardiovascular disease," Diabetes Care, 1991, 14:173-194.
Deng et al "Novel ATP8B1 mutation in an adult male with progressive familial intrahepatic cholestasis," World J Gastroenterol., 2012, 18(44):6504-6509.
Di Lascio et al., "Steato-Score: Non-Invasive Quantitative Assessment of Liver Fat by Ultrasound Imaging," Ultrasound Med Biol., 2018, 44(8):1585-1596.
Di Padova et al., "Double-blind placebo-controlled clinical trial of microporous chlestyramine in the treatment of intra- and extra-hepatic cholestasis: relationship between itching and serum bile acids," Methods Find Exp Clin Pharmacol., Dec. 1984, 6(12):773-776 (Abstract only).
DiBaise et al., "Bile Acids: An Under recognized and Underappreciated Cause of Chronic Diarrhea", Pract. Gastroenterol. vol. 36(10), p. 32-44, 2012.
Dixon et al., "An expanded role for heterozygous mutations of ABCB4, ABCB11, ATP8B1, ABCC2 and TJP2 in intrahepatic cholestasis of pregnancy," Scientific Reports, 2017, 7(1):11823.
Dong et al., "Structure-activity relationship for FDA approved drugs as inhibitors of the human sodium taurocholate cotransporting polypeptide (NTCP).," Mol. Pharm. 2013, 10(3):1008-1019.
Dongiovanni et al., "Genetic Predisposition in NAFLD and NASH: Impact on Severity of Liver Disease and Response to Treatment," Curren Pharma Design, 2013, 19:5219-5238.
Drage et al., "Exon-skipping and mRNA decay in human liver tissue: molecular consequences of pathogenic bile salt export pump mutations," Sci Rep., 2016, vol. 6: 24827.
Drage et al., "Sequencing of FIC1, BSEP and MDR3 in a large cohort of patients with cholestasis revealed a high number of different genetic variants," J Hepatol. 2017, 67(6):1253-1264.
Droge et al., "Joint Annual Meeting," Zeitschrift fur Gastroenterologie 2015, 53(12) Abstract No. A3-27. Meeting Info: 32. Jahrestagung der Deutschen Arbeitsgemeinschaft zum Studium der Leber. Dusseldorf, Germany, Jan. 22, 2016-Jan. 23, 2016.
Einspahr et al., "Protective role of wheat bran fiber: data from marker trials," Am. J. Med., 106(1A):32s-37s, Jan. 1999.
Ekkehard Sturm et al. The ileal bile acid transport inhibitor A4250 reduced pruritus and serum bile acid levels in children with cholestatic liver disease and pruritus: final results from a multiple-dose, open-label, multinational study Hepatology 2017; 66: 646-47 (Suppl. 1). doi: 10.1002/hep.29501.
Ellinger et al., "Partial external biliary diversion in bile salt export pump deficiency: Association between outcome and mutation," World J Gastroenterol., 2017, 23(29):5295-5303.
Ellis et al., "Zebrafish abcb11b mutant reveals strategies to restore bile excretion inipaired by bile salt export pump deficiency," Hepatology, 2018, 67(4)1531-1545.
Espenshade and Hughes, "Regulation of Sterol Synthesis in Eukaryotes," Annu. Rev. Genet., 2007, 41:401-427.
Evason et al., "Morphologic findings in progressive familial intrahepatic cholestasis 2 (PFIC2): correlation with genetic and in immunohistochemical studies," Am J Surg Pathol., 2011, 35(5):687-696.
Evonik Industries, "Eudragit FS 30 D," Jul. 9, 2008, http://www.pharma-polymers.com.pharmapolymers/MCMbase/Pages/ProvideResource.aspx?respath=/NR/rdonlyres/BDD7E168-922E-4AB1-861F-EEEB58B85642/0/ELDRAGITES30D_Promotiondatasheet_09072008.
Extended European Search Report in European Application No. 11840392.2, dated Feb. 24, 2014, 7 pages.
Extended European Search Report in European Application No. 11840481.3, dated Feb. 13, 2014, 10 pages.
Faubion et al., "Toxic bile salts induce rodent hepatocyte apoptosis via direct activation of Fas," The Journal of Clinical Investigation, 103: 1, 137-145, 1999.
Ferreira et al., Pediatric Transplantation 2013, 17 (Suppl. 1):99. Abstract No. 239. Meeting Info: IPTA 7th Congress on Pediatric Transplantation. Warsaw, Poland. Jul. 13, 2013-Jul. 16, 2013.
Ferslew et al., "Altered Bile Acid Metabolome in Patients with Nonalcoholic Steatohepatitis," Dig Dis Sci., 2015, 60(11):3318-3328.
Folmer et al., "Differential effects of progressive familial intrahepatic cholestasis type 1 and benign recurrent intrahepatic cholestasis type 1 mutations on canalicular localization of ATP8B1," Hepatology., 2009, 50(5):1597-1605.
Forner et al., "Treatment of hepatocellular carcinoma," Critical Reviews in Oncology/Hematology, 2006, 60:89-98.
Francalanci et al., "Progressive familial intrahepatic cholestasis: Detection of new mutations and unusal modality of transmission," Digestive and Liver Disease 2010, 42(Suppl. 1):516, Abstract No. T.N.5.
Francalanci et al., Laboratory Investigation 2011, vol. 91, Supp. Suppl. 1, pp. 360A. Abstract No. 1526.
Fuentes-Zaragoza al., "Resistant Starch as functional ingredient: A review", Food Research International, 43, 931-942, 2010.
Gao et al., "Detection of hepatitis in children with idiopathic cholestatic bile salt export pump gene mutations," Shandong Yiyao, 2012, 52(10):14-16.
Gao et al., "The Identification of Two New ABCB11 Gene Mutations and the Treatment Outcome in a Young Adult with Benign Recurrent Intrahepatic Cholestasis: A Case Report," Hepatitis Monthly 2017, 17(10):e55087/1-e55087/6.
Gibney, "Shire Reports Topline Results from First of Three Placebo-Controlled Phase 2 Studies of SHP625 (LUM001) in Children with Alagille Syndrome," FierceBiotech.com, Apr. 9, 2015, http://www.firecebiotech.com/node/443176/print, 3 pages.
Gillberg et al., "The IBAT Inhibition by A3309—A Potential Mechanism for the Treatment of Constipation," Gastroenterology, 2010, 138(5), Supp 1, S-224.
Giovannoni et al., "Genetics and Molecular Modeling of New Mutations of Familial Intrahepatic Cholestasis in a Single Italian Center," PLoS One, 2015, 10(12):e0145021.
Glagov et al., "Compensatory enlargement of human athersclerotic coronary arteries," N Engl. J. Med., May 1987, 316(22):1371-1375 (Abstract Only).
Goldschmidt et al., "Increased frequency of double and triple heterozygous gene variants in children with intrahepatic cholestasis," Hepatol Res., 2016, 46(4):306-311.
Govers et al., "Characterization of the adsorption of conjugated and unconjugated bile acids to insoluble, amorphous calcium phosphate", Journal of Lipid Research 35(5):741-748, 1994.

(56) References Cited

OTHER PUBLICATIONS

Griffin, et al., "A novel gene mutation in ABCB11 in siblings with progressive familial intrahepatic cholestasis type 2," Canadian Journal of Gastroenterology and Hepatology 2016, vol. 2016, Abstract No. A200. Meeting Info: 2016 Canadian Digestive Diseases Week, CDDW 2016. Montreal, QC, United States. Feb. 26, 2016-Feb. 29, 2016.
Gunaydin et al., "Progressive familial intrahepatic cholestasis: diagnosis, management, and treatment," Hepat Med., 2018, 10:95-104.
Guorui et al., "Genetic diagnosis of progressive familial intrahepatic cholestasis type 2," Linchnang Erke Zazhi, 2013, 31(10):905-909.
Guzman et al., "Does Nonalcoholic Fatty Liver Disease Predispose Patients to Hepatocellular Carcinoma in the Absence of Cirrhosis?" Archives of pathology & laboratory medicine, Nov. 2008, 132(11):1761-1766.
Hancock et al., "Molecular Mobility of amorphous pharmaceutical solids below their glass transition temperatures," 12(6): 799-806, 1995.
Hao et al., "Application of high-throughput sequencing technologies with target capture/target next-generation sequencing in diagnosis of neonatal intrahepatic cholestasis causes by citrin deficiency (NICDD)," International Journal of Clinical and Experimental Pathology, 2017, 10(3):3480-3487.
Harmanci et al., "Late onset drug induced cholestasis in a living-related liver transplantation donor to son with progressive familial intrahepatic cholestasis," Experimental and Clinical Transplantation 2015, 13(2):76, Abstract No. P62. Meeting Info: 1st Congress of the Turkic World Transplantation Society. Astana, Kazakhstan. May 20, 2015-May 22, 2015.
Hasegawa et al., "Intractable itch relieved by 4-phenylbutyrate therapy in patients with progressive familial intrahepatic cholestasis type 1," Orphanet J Rare Dis., 2014, 9:89.
Hayashi et al., "Assessment of ATP8B1 Deficiency in Pediatric Patients With Cholestasis Using Peripheral Blood Monocyte-Derived Macrophages," EBioMedicine, 2018, 27:187-199.
Hayashi et al., "Successful treatment with 4-phenylbutyrate in a patient with benign recurrent intrahepatic cholestasis type 2 refractory to biliary drainage and bilirubin absorption," Hepatol Res., 2016, 46(2):192-200.
Heathcote, "Management of primary biliary cirrhosis," Hepatology, 2000, 31(4):1005-1013.
hepc.liverfoundation.org [online]. "Nonalcoholic Fatty Liver Disease," Brochure, 2016 [retrieved on Feb. 1, 2018]. Retrieved from the Internet: URL<http://hepc.liverfoundation.org/wp-content/uploads/2012/07/NAFLD-Brochure-2016.pdf>, 8 pages.
Herbst et al., "Taking the next step forward—Diagnosing inherited infantile cholestatic disorders with next generation sequencing," Mol Cell Probes, 2015, 29(5):291-298.
Higaki et al., "Inhibition of ileal na+/bile acid cotranporter by S-8921 reduces serum cholesteral and prevents atherosclerosis in rabbits", Arteriosclerosis, Thrombosis, and Vascular Biology 18(8):1304-1311, 1998.
Ho et al., "Polymorphic variants in the human bile salt export pump (BSEP; ABCB11): functional characterization and interindividual-variability," Pharmacogenet Genomics, 2010, 20(1):45-57.
Hoffman et al., Human Anatomy, picture of the colon, p. 1-7, https://www.webmd.com/digestive-disorders/picture-of-the-colon #1, Accesses Aug. 4, 2019.
Hollands et al., "Illeal exclusion for Byler's disease: an alternative surgical approach with promising early results for pruritis," Journal of Pediatric Surgery, Feb. 1988, 33(2): 220-224.
Holz et al., "Can genetic testing guide the therapy of cholestatic pruritus? A case of benign recurrent intrahepatic cholestasis type 2 with severe nasobiliary drainage-refractory itch," Hepatol Commun., 2018, 2(2):152-154.
Holz et al., "Plasma separation and anion adsorption results in rapid improvement of nasobiliary drainage (NBD)-refractory pruritus in BRIC type 2," Zeitschrift fur Gastroenterologic 2016, vol. 54, No. 8. Abstract. No. KV275. Meeting Info: Viszeralmedizin 2016, 71, Hamburg, Germany. Sep. 21, 2016-Sep. 24, 2016.
Hsu et al., "Adult progressive intrahepatic cholestasis associated with genetic variations in ATP8B1 and ABCB11," Hepatol Res., 2009, 39(6):625-631.
Hu et al., "Diagnosis of ABCB11 gene mutations in children with intrahepatic cholestasis using high resolution melting analysis and direct sequencing," Mol Med Rep., 2014, 10(3):1264-1274.
Huang et al., "Discovery of Potent, Non-systemic Apical Sodium-Codependent Bile Acid Transporter Inhibitors (Part 2)," J. Med. Chem., 2005, 48:5853-5868.
Imagawa et al., "Clinical phenotype and molecular analysis of a homozygous ABCB11 mutation responsible for progressive infantile cholestasis," J Hum Genet, 2018, 63(5):569-577.
Imagawa et al., "Generation of a bile salt export pump deficiency model using patient-specific induced pluripotent stem cell-derived hepatocyte-like cells," Sci Rep., 2017, 7:41806.
Imagawa et al., "Splicing analysis using induced pluripotent stem cell-derived hepatocyte-like cells generated from a patient with progressive familial intrahepatic cholestatsis type 2," Journal of Pediatric Gastroenterology and Nutrition 2016, 63(2):551, Abstract No. 166, Meeting Info: World Congress of Pediatric Gastroenterology, Hepatology and Nutrition 2016. Montreal, QC, Canada, Oct. 5, 2016-Oct. 8, 2016.
International Preliminary Report on Patentability for Application No. PCT/JP2015/068240, dated Jan. 5, 2017, 12 pages. (with English translation).
International Preliminary Report on Patentability for international Application No. PCT/EP2015/074573, dated Apr. 25, 2017, 8 pages.
International Preliminary Report on Patentability for International Application No. PCT/SE2011/051335, dated May 23, 2011, 7 pages.
International Preliminary Report on Patentability for International Application No. PCT/SE2011/051336, dated May 23, 2013, 11 pages.
International Search Report and Written Opinion for Application No. PCT/EP2014/058432, dated Jul. 11, 2014, 9 pages.
International Search Report and Written Opinion for Application No. PCT/SE2017/050126, dated Apr. 24, 2017, 27 pages.
International Search Report and Written Opinion for Application No. PCT/SE2017/050127, dated May 8, 2017, 16 pages.
International Search Report and Written Opinion for Application No. PCT/SE2017/050128, dared May 8, 2017, 16 pages.
International Search Report and Written Opinion for Application No. PCT/EP2019/064602, dated Aug. 9, 2019, 11 pages.
International Search Report and Written Opinion for International Application No. PCT/EP2015/074573, dated Apr. 28, 2016, 11 pages.
International Search Report and Written Opinion for International Application No. PCT/SE2011/051335, dated Feb. 3, 2012, 12 pages.
International Search Report and Written Opinion for International Application No., dated Feb. 22, 2012, 18 pages.
International Search Report and Written Opinion in International Application No. PCT/SE2018/050802, dated Oct. 26, 2018.
International Search Report and Written Opinion in International Application No. PCT/SE2018/050803, dated Oct. 26, 2018.
International Search Report, Application No. PCT/JP2015/068240, dated Sep. 15, 2015, 11 pages (with English translation).
Ishak et al., "Histological grading and staging of chronic hepatitis," J. Hepatol. 1995, vol. 22, p. 696-699.
Ishibashi et al., "Hypercholesterolemia in low density lipoprotein receptor knockout mice and its reversal by adenovirus-mediated gene delivery", Journal of Clinical Investigation 92(2):883-893, 1993.
Islam and Di Baise. "Bile Acids: An underrecognized and under-appreciated cause of chronic diarrhea," Pract. Gastroenterol. 2012, vol. 36(10), p. 32-44.
Ivashkin et al., "A novel mutation of ATP8B1 gene in young patient with familial intrahepatic cholestasis.," Hepatology International 2016, 10(1):5461, Abstract No. LBO-38. Meeting Info: 25th Annual Conference of the Asian Pacific Association for the Study of the Liver, APASL 2016. Tokyo, Japan. Feb. 20, 2016-Feb. 24, 2016.

(56) References Cited

OTHER PUBLICATIONS

Jacobsen et al., "Effect of enterocoated cholestyramine on bowel habit after ileal resection: a double blind crossover study," Br. Med. J. 1985, vol. 290, p. 1315-1318.

Jacquet et al., "Alagille Syndrome in Adult Patients: It is Never Too Late," American Journal of Kidney Diseases, May 2007, 49(5):705-709.

Jankowska et al., "[Cholestatic liver disease in children]," Przegl. Epidemiol., 56:16-21, 2002.

Jankowska et al., "Heal exclusion in children with progressive familial intrahepatic cholestasis," J Pediatr Gastroenterol Nutr. 2014,58(1):92-95.

Jansen et al., "Endogenous bile acids as carcinogens," Journal of Hepatology, Sep. 2007, 47(3):434-435.

Jaquotot-Haerranz et al., "Clinical variability of mutations in the ABCB11 gene: a case report," Rev Esp Enferm Dig., 2013, 105(1):52-54.

Jericho et al., "Bile Acid Pool Dynamics in Progressive Familial Intrahepatic Cholestasis with Partial External Bile Diversion," Journal of Pediatric Gastroenterology and Nutrition, 2015, 60(3):368-374.

Jiang et al., "Nonalcoholic steatohepatitis a precursor for hepatocellular carcinoma development," World Journal of Gastroenterology: WJG, Nov. 28, 2014, 20(44):16464-16473.

Jirsa et al., "Indel in the FIC1/ATP8B1 gene—a novel rare type of mutation associated with benign recurrent intrahepatic cholestasis," Hepatol Res. 2004, 30(1):1-3.

Jung et al., "Prenatal molecular diagnosis of inherited cholestatic diseases," J Pediatr Gastroenterol Nutr. 2007, 44(4):453-458.

Kagawa et al., "Phenotypic differences in PFIC2 and BRIC2 correlate with protein stability of mutant Bsep and impaired taurocholate secretion in MDCK II cells," Am J Physiol Gastrointest Liver Physiol., 2008, 294(1):G58-67.

Kang et al., "Progressive Familial Intrahepatic Cholestasis in Korea: A Clinicopathological Study of Five Patients," J Pathol Transl Med. May 16, 2019, 53(4):253-260.

Karpen and Dawson, "Not all (bile acids) who wander are lost: the first report of a patient with an isolated NTCP defect," Hepatology, 2015, 61(1):24-27.

Khosla et al., "Recurrent Post-partum Jaundice: Rare Genetic Disorder With Novel Genetic Mutations Identified," American Journal of Gastroenterology 2015, 110(1):5397. Meeting Info.: 80th Annual Scientific Meeting of the American-College-of-Gastroenterology. Honolulu, HI, USA. Oct. 16-21, 2015.

Kim, "Novel mutation of ABCB11 heterozygote associated with transient neonatal intrahepatic cholestasis," Journal of Pediatric Gastroenterology and Nutrition 2016, 62(1):620, Abstract No. H-P-045. Meeting Info: 49th Annual Meeting of the European Society for Pediatric Gastroenterology, Hepatology and Nutrition, ESPGHAN 2016. Athens, Greece. May 25, 2016-May 28, 2016.

Kleiner et al., "Design and validation of a histological scoring system for nonalcoholic fatty liver disease," Hepatology, 2005, 41(6):1313-1321.

Klomp et al., "Characterization of mutations in ATP8B1 associated with hereditary cholestasis," Hepatology, 2004, 40(1):27-38.

Knisely et al., "Hepatocellular Carcinoma in ten children under five years of age with bile salt export pump deficiency," Hepatology, Aug. 2006, 44(2):478-486.

Kooistra, et al., "KLIFS: A structural kinase-ligand interaction database," Nucleic Acids Res., 2016, vol. 44, No. D1, pp. D365-D371.

Korman et al., "Assessment of Activity in Chronic Active Liver Disease," New England Journal of Medicine, 2010, 290(25):1399-1402.

Kosters et al., "Bile acid transporters in health and disease," Xenobiotica 2008, 38(7-8):1043-1071.

Krawczyk et al., "Prolonged cholestasis triggered by hepatitis A virus infection and variants of the hepatocanalicular phospholipid and bile salt transporters," Ann Hepatol., 2012, 11(5):710-744.

Kumar and Tandon, "Use of ursodeoxycholic acid in liver diseases," J. Gastroenterology and Hepatology, 2001, 16:3-14.

Kurata et al., "A novel class of apical sodium-dependent bile acid transporter inhibitors: the amphiphilic 4-oxo-1-phenyl-1,4-dihydroquinotine derivatives," Bioorganic & Medicinal Chemistry Letters, 2004, 14:1183-1186.

Kurbegov et al., Biliary diversion for progressive familial intrahepatic cholestasis: Improved liver morphology and bile acid profile, Gastroenterology, 125: 4, 1227-1234, 2003.

Lam et al., "A patient with novel ABCB11 gene mutations with phenotypic transition between BRIC2 and PFIC2," J Hepatol. 2006, 44(1):240-242.

Lam et al., "Levels of plasma membrane expression in progressive and benign mutations of the bile salt export pump (Bsep/Abcb11) correlate with severity of cholestatic diseases," Am J Physiol Cell Physiol. 2007, 293(5):C1709-16.

Lang et al., "Genetic variability, haplotype structures, and ethnic diversity of hepatic transporters MDR3 (ABCB4) and bile salt export pump (ABCB11)," Drug Metab Dispos. 2006, 34(9):1582-1599.

Lang et al., "Mutations and polymorphisms in the bile salt export pump and the multidnig resistance protein 3 associated with drug-induced liver injury," Pharmacogenet Genomics, 2007, 17(1):47-60.

Lanzini et al., "Intestinal absorption of the bile acid analogue $^{75}$Se-homocholic acid-taurine is increased in primary biliary cirrhosis and reverts to normal during ursodeoycholic acid administrations," Gut, 2003, 52:1371-1375.

Lee et al., "Early Diagnosis of ABCB11 Spectnun Liver Disorders by Next Generation Sequencing," Pediatr Gastroenterol Hepatol Nutr. 2017, 20(2):114-123.

Lewis et al., "Effects of 2164U90 on ileal bile acid adsorption and serum cholesterol in rats and mice", Journal of Lipid Research 36(5):1098-1105, 1995.

Li et al., "ATP8B1 and ABCB11 mutations in Chinese patients with normal gamma-glutamyl transferase cholestasis: Phenotypic differences between progressive familial intrahepatic cholestasis type 1 and 2," Hepatology International 2017, 11(1):5180. Abstract No. OP284.

Li et al., "Clinical feature and gene mutation analysis of one pedigree with progressive familial intrahepatic cholestasis type II," Hepatology International 2017, 11(1):5362, Abstract No. PP0347. Meeting Info: 26th Annual Conference of the Asian Pacific Association for the Study of the Liver, APASL 2017. Shanghai, China. Feb. 15, 2017-Feb. 19, 2017.

Li et al., "Effect of Resistant Starch Film Properties on the Colon-Targeting Release of Drug From Coated Pellets", 152 J Control. Rel. e5, 2011.

Lichtinghagen R, et al., "The Enhanced Liver Fibrosis (ELF) score: normal values, influence factors and proposed cut-off values," J Hepatol. Aug. 2013;59(2):236-42.

Lin et al., "[Clinical and genetic analysis of an infant with progressive cholestasis type II]," Zhongguo Dang Dai Er Ke Za Zhi. 2018, 20(9)758-764 (with English abstract).

Ling, "Congenital cholestatic syndromes: What happens when children grow up?," Can J Gastroenterol, Nov. 11, 2007, 21(11):743-751.

Liu et al., "ABCB11 gene mutations in Chinese children with progressive intrahepatic cholestasis and low gamma glutamyltransferase," Liver International 2010, 30(6):809-815.

Liu et al., "Association of variants of ABCB11, with transient neonatal cholestasis," Pediatr Int. 2013, 55(2):138-144.

Liu et al., "Characterization of ATP8B1 gene mutations and a hot-linked mutation found in Chinese children with progressive intrahepatic cholestasis and low GGT," J Pediatr Gastroenterol Nutr., 2010, 50(2):179-183.

Liu et al., "Characterization of ATP8B1 mutations and a hot linked mutation found in Chinese children with progressive intrahepatic cholestasis and low GGT," Hepatology International 2009, 3(1):184-185, Abstract No. PE405. Meeting Info: 19th Conference of the Asian Pacific Association for the Study of the Liver. Hong Kong, China. Feb. 13, 2009-Feb. 16, 2009.

(56) References Cited

OTHER PUBLICATIONS

Liu et al., "Homozygous p.Ser267Phe in SLC10A1 is associated with a new type of hypercholanemia and implications for personalized medicine," Scientific Reports, 2017, 7:9214.
Longo et al., "Hyperlipidemia in chronic cholestatic liver disease," Curr. Treat. Options Gastrenterol., 2001, 4:111-114.
Lv et al., "Noninvasive Quantitative Detection Methods of Liver Fat Content in Nonalcoholic Fatty Liver Disease," J Clin Transl Hepatol, 2018, 6(2):217-221.
Lykavieris et al., "Outcome of liver disease in children with Alagille syndrome: a study of 163 patients," Gut, 2001, 49:431-435.
Maggiore et al., "Relapsing features of bile salt export pump deficiency after liver transplantation in two patients with progressive familial intrahepatic cholestasis type 2," J Hepatol. 2010, 53(5):981-6.
Manghat and Wierzbicki, "Colesevelam hydrochloride: a specifically engineered bile acid sequestrant," Future Lipidology, 3(3):237-255, Jun. 2008.
Marzorati et al., "A novel hypromellose capsule, with acid resistance properties, permits the targeted delivery of acid-sensitive products to the intestine," LWT—Food Sci. Technol 2015, vol. 60, p. 544-551.
Masahata et al., "Recurrence of Progressive Familial Intraltepatic Cholestasis Type 2 Phenotype After Living-donor Liver Transplantation: A Case Report," Transplant Proc. 2016, 48(9):3156-3162.
Matte et al., "Analysis of gene mutations in children with cholestasis of undefined etiology," J Pediatr Gastroenterol Nutr. 2010, 51(4):488-493.
McCullough et al., "The epidemiology and risk factors of NASH.", Blackwell Publishing, Chapter 3, 2005.
McKay et al., "Mutation detection in cholestatic patients using microarray resequencing of ATP8B1 and ABCB11 [version 2; peer review: 2 approved, 1 approved with reservations]," F1000 Res., 2013, 2:32.
McMichael and Potter, "Reproduction, endogenous and exogenous sex hormones, and colon cancer: a review and hypothesis," J. Natl. Cancer Inst., 65(6):1201-07, Dec. 1980.
McPherson et al., "Simple non-invasive fibrosis scoring systems can reliably exclude advanced fibrosis in patients with non-alcoholic fatty liver disease," Gut 2010, 59(9):1265-9.
MerckManuals.com, "Obesity," 2008, Merch Manual for Health Care Professionals, Section—Nutritional Disorders, Chapter—"Obesity and the metabolic syndrome," retrieved on Feb. 22, 2012, http://www.merchmanuals.com/professional/nutritional_disorders/obesity_and_the_metabolic_syndrome/metabolic_syndrome.html?qt=metabolicsyndrome&alt=sh, 10 pages.
Miloh et al., Gastroenterology 2006, vol. 130, No. 4, Suppl. 2, pp. A759-A760. Meeting Info: Digestive Disease Week Meeting/107th Annual Meeting of the American-Gastroenterological Association. Los Angeles, CA, USA. May 19.
Mizuochi et al., "Characterization of urinary bile acids in a pediatric BRIC-1 patient: effect of rifampicin treatment," Clin Chim Acta. 2012, 413(15-16):1301-1304.
Moghadamrad et al., "Cholestasis in a patient with gallstones and a normal gamma-glutamyl transferase," Hepatology, 2013, 57(6):2539-2541.
Morissette et al., "High-throughput crystallization: polymorphs, salts, co-crystals and solvates of pharmaceutical solids," Advanced Drug Delivery Reviews, 2004, 56:275-300.
Mouzaki and Allard, "Non-alcoholic steatohepatitis: the therapeutic challenge of a global epidemic," Annals of Gastroenterology, 2012, 25: 207-217.
Mowat et al., "Respiratory chain complex III [correction of complex] in deficiency with pruritus: a novel vitamin responsive clinical feature," J. Pediatr., 134(3):352-4, Mar. 1999.
Nagasaka et al., "Depletion of high-density lipoprotein and appearance of triglyceride-rich low-density lipoprotein in a Japanese patient with FIC1 deficiency manifesting benign recurrent intrahepatic cholestasis," J Pediatr Gastroenterol Nutr., 2007, 45(1)96-105.

Nagase et al., "Preparation of Benzothiazepine derivatives with activity of bringing about high blood GLP-1 concentration," CAPLUS Database, Jul. 2002, retrieved from STN Database on Mar. 31, 2014, https://stneasy.cas.org/tmp/20140331/443268-0025347726-200/349520738.html, 2 pages.
Narchi et al., "Intrahepatic cholestasis in two omani siblings associated with a novel homozygous ATP8B1 mutation, c.379C>G (p.L127V).," Saudi J Gastroenterol. 2017, 23(5):303-305.
Neuman, et al., "Biomarkers in nonalcoholic fatty liver disease," Can. J. Gastroenterol. Hepatol. 2014, 28(11):607-618.
Ng et al., "Autoimmune haemolytic anaemia with giant cell hepatitis and concurrent bile salt export pump deficiency: Challenges in diagnosis and management," Journal of Pediatric Gastroenterology and Nutrition 2018, 66(2):860, Abstract No. H-P-127. Meeting Info: 51st Annual Meeting European Society for Paediatric Gastroenterology, Hepatology and Nutrition, ESPGHAN 2018. Geneva, Switzerland. May 9, 2018-May 12, 2018.
Noe et al., "Impaired expression and function of the bile salt export pump due to three novel ABCB11 mutations in intrahepatic cholestasis," J Hepatol. 2005, 43(3):536-543.
O'Neill et al.,"Comparison of efficacy of plant sterol ester and sterol ester: short-term and longer-term studies," American Journal of Cardiology, 96(1A):29d-36D, Jul. 2005.
Okubo et al., "II, Daihyoteki Shikkan no Shimyo to Genkyo to Shorai Tenbo 6. Nanjisei Benpi," The Journal of the Japanese Society of Internal Medicine Jan. 10, 2013 (Jan. 10, 2013), 102(1), pp. 83-89.
Pai et al. Compression and evaluation of extended release matrix pellets prepared by the extrusion/spheronization process into disintegrating tablets. Brazilian Journal of Pharmaceutical Sciences. vol. 48, n. 1, Jan. 2012 (Year: 2012).
Painter et al., "Sequence variation in the ATP8B1 gene and intrahepatic cholestasis of pregnancy," Eur J Hum Genet. 2005, 13(4):435-439.
Park et al., "Clinical and ABCB11 profiles in Korean infants with progressive familial intrahepatic cholestasis," World J Gastroenterol., 2016, 22(20):4901-4907.
Parker et al., "Molecular mechanisms underlying bile acid-stimulated glucagon-like peptide-1 secretion," British J. Pharmacology, 2012, 165:414-423.
Patani et al., "Bioisosterism: A Rational Approach in Drug Design," Chem Rev, 1996, 96:3147-3176.
Pattni and Walters, "Recent advances in the understanding of bile acid malabsorption," Br. Med. Bull. 2009, vol. 92, p. 79-93.
Pauli-Magnus et al., "Enterohepatic transport of bile salts and genetics of cholestasis," Journal of Hepatology, 2005, 43(2):342-357.
Pauli-Magnus et al., "Impaired expression and function of the bile salt export pump due to three novel ABCB11 mutations in intrahepatic cholestasis," Hepatology 2003, vol. 38, No. 4 Suppl. 1, pp. 518A. print. Meeting Info.: 54th Annual Meeting of the Anietican Association for the Study of Liver Diseases. Boston, MA, USA. Oct. 24-28, 2003. American Association for the Study of Liver Diseases.
Peng et al., "[Relationship between phenotype and genotype of ABCB11 deficiency in siblings and literature review].," Zhonghua er ke za zhi (Chinese journal of pediatrics) 2018, 56(6):440-444.
Perez et al., "Bile-acid-induced cell injury and protection," World J Gastroenterol, Apr. 2009, 15(14)1677-1689.
Perumpail et al., "Clinical epidemiology and disease burden of nonalcoholic fatty liver disease," World Journal of Gastroenterology, Dec. 2017, 23(47): 8263-8276.
Plump et al., "Severe hypercholesterolemia and atherosclerosis in apolipoprotein E-deficient mice created by homologous recombination in ES cells", Cell (71):343-353, 1992.
Podesta et al., "Treatment of pruritus of primary biliary cirrhosis with rifampin," Dig. Dis. Sci, 1991, 36(2):216-220.
Possemiers et al, "PCR-DGGE-based quantification of stability of the microbial community in a simulator of the human intestinal microbial ecosystem," FEMS Microbiol. Ecol. 2004, vol. 49, p. 495-507.
Poupon et al., "Chronic Cholestatic Disease," J. Hepatology, 2000, 32(1):12-140.

(56) References Cited

OTHER PUBLICATIONS

Qiu et al., "Defects in myosin VB are associated with a spectrum of previously undiagnosed low γ-glutamyltransferase cholestasis," Hepatology 2017, 65(5)1655-1669.
Qiu et al., "Disruption of BSEP function in HepaRG cells alters bile acid disposition and is a susceptive factor to drug-induced cholestatic injury," Mol. Pharmaceutics, 13:4,, 2016 (Abstract only).
Reeder et al., "Quantitative assessment of liver fat with magnetic resonance imaging and spectroscopy," J Magn Reson Imaging. 2011, 34(4):729-749.
Renga et al., "Role of FXR in regulating bile acid homeostasis and relevance for human diseases," Curr. Drug. Targets Immune Endocr. Metabol. Disord., 5(3):289-303, Sep. 2005.
Report EC20082069.02.01 dated Feb. 2009, filed with appellant's letter of Apr. 26, 2011.
Report filed at oral proceedings before opposition division, GMS-CFEP-2007-20, "Filtration and Drying Study on Amorphous and Form IV Atorvastatin Calcium," 2007.
Rolo et al., "Bile acids affect liver mitochondrial bioenergetics: Possible relevance for cholestasis therapy," Toxocological Sciences, 57: 177-185, 2000.
Rumbo et al., Transplantation 2018, vol. 102, No. 7, Supp. Supplement 1, pp. 5848. Abstract No. p. 752. Meeting Info: 27th International Congress of the Transplantation Society, TTS 2018. Madrid, Spain. Jun. 30, 2018-Jul. 5, 2018.
Sanyal et al. The etiology of hepatocellular carcinoma and consequences of treatment. The Oncologist, 2010, 15 Suppl 4, 14-22.
Satapathy and Sanyal, "Epidemiology and Natural History of Nonalcoholic Fatty Liver Disease," Seminars in Liver Disease, Aug. 2015, 35(3): 221-235.
Sattler et al., "Functional analysis of previously uncharacterised disease-causing mutations of the bile salt export pump," Journal of Hepatology 2017, 66(1):5177. Meeting Info: International Liver Congress/ 52nd Annual Meeting of the European-Association-for-the-Studyof- the-Liver. Amsterdam, Netherlands. Apr. 19-23, 2017. European Assoc Study Liver.
Scheimann et al., "Prevalence of Abcb 11 mutations among children with cholelithiasis," Gastroenterology 2007, 132(4)Suppl. 2:A452, Meeting Info.: Digestive Disease Week Meeting/108th Annual Meeting of the American-GastroenterologicalAssociation. Washington, DC, USA. May 19-24, 2007. Amer Gastroenterol Assoc; Amer Assoc Study Liver Dis; Amer Soc Gastrointestinal Endoscopy; Soc Surg Alimentary Tract.
Scheuer. "Primary Biliary Cirrhosis," Proc. R. Soc. Med., Dec. 1967, 60:1257-1260.
Schiller, "Review article: the therapy of constipation", Alimentary Pharmacology and Therapeutics 15(6):749-763, 2001.
Schumpelick et al., "[Ulcerative colitis—late functional results of ileoanal pouch anastomosis]," Chirung, 69(10):1013-19, Oct. 1998.
Sciveres. "Relapsing features of bile salt export pump (BSEP) deficiency in a patient successfully transplanted for progressive familial intrahepatic cholestasis type 2 (PFIC2).," Digestive and Liver Disease 2010, 42(5):5329. Abstract No. 4 CO18. Meeting Info: 17th National Congress SIGENP. Pescara, Italy. Oct. 7, 2010-Oct. 9, 2010.
Shah et al.. "Progressive Familial Intrahepatic Cholestasis Type 2 in an Indian Child," J Pediatr Genet. 2017, 6(2):126-127.
Shah et al., "Role of Caco-2 Cell Monolayers in Prediction of Intestinal Drug, Absorption," Biotechnol. Prog., 2006, 22:186-198.
Shang et al., "Colesevelam improves insulin resistance in a diet-induced obesity (F-DIO) rat model by increasing the release of GLP-1," Am J. Physiol Gastrointest Liver Physiol, 2010, 298:G419-G424.
Shaprio et al., "DHPLC screening for mutations in progressive familial intrahepatic cholestasis patients," J Hum Genet. 2010, 55(5):308-313.
Sharma et al., "Spectrum of genomic variations in Indian patients with progressive familial intrahepatic cholestasis," BMC Gastroenterol, 2018, 18(1):107.

Sharma et al., "Spectrum of sequence variations in Indian patients with progressive familial intrahepatic cholestasis show several novel polymoiphisms," Indian Journal of Gastroenterology 2017, 36(1):A99. Abstract No. M-20. Meeting Info: 58th Annual Conference of the Indian Society of Gastroenterology, ISGCON 2017. Bhubaneswar, India, Dec. 14, 2017-Dec. 17, 2017.
Sherrif et al., "Hepatotoxicity from anabolic androgenic steroids marketed as dietary supplements: contribution from ATP8B1/ABCB11 mutations?," Liver international: official journal of the International Association for the Study of the Liver, 2013, 33(8):1266-1270.
Shimizu et al., "Living-related liver transplantation for siblings with progressive familial intrahepatic cholestasis 2, with novel genetic findings," Am J Transplant 2011, 11(2):394-398.
Simons, "The fate of the orally administered bile acid sequestrant, polidexide, in humans," Clin. Exp. Pharmacol. Physiol., 3(1):99-101, Jan.-Feb. 1976.
Singhal et al., "Drug polymorphism and dosage form design: a practical perspective," Adv Drug Deliv Rev, Feb. 23, 2004, 56(3):335-347.
Sinha and Kumria, "Microbially triggered drug delivery to the colon," Eur. J. Pharm. Sci. 2003, vol. 18, p. 3-18.
Sirtori, "Mechanisms of lipid-lowering agents," Cardiology, 78(3):226-35, 1991.
Sohn et al., "Benign Recurrent Intrahepatic Cholestasis Type 2 in Siblings with Novel ABCB11 Mutations," Pediatr Gastroenterol Hepatol Nutr. 2019, 22(2):201-206.
Sorrentino et al., "A Clinical-Morphological Study on Cholestatic Presentation of Nonalcoholic Fatty Liver Disease," Digestive Disease and Sciences, Jun. 2005, 50(6):1130-1135.
Sprong et al., "Dietary Calcium Phosphate Promotes Listeria monosytogenes colonization and translocation in rats red diets containing corn oil but not milk fat1", J. Nutrition (US) 132(6):1269-1274, 2002.
Squires et al., "Clinical Variability After Partial External Binary Diversion in Familial Intrahepatic Cholestasis 1 Deficiency," J Pediatr Gastroenterol Nutr. 2017, 64(3):425-430.
Staels and Kuipers, "Bile Acid Sequestrants and the Treatment of Type 2 Diabetes Mellitus," Drugs, 2007, 67(10):1383-1392.
Stein, "Managing Dyslipidemia in the High-Risk Patient," Am J. Cardiol., 2002, 89:50-57.
Stindt et al., "A novel mutation within a transmembrane helix of the bile salt export pump (BSEP, ABCB11) with delayed development of cirrhosis," Liver Int. 2013, 33(10):1527-1735.
Stolz et al., "Severe and protracted cholestasis in 44 young men taking bodybuilding supplements: assessment of genetic, clinical and chemical risk factors," Aliment Pharmacol Ther. 2019, 49(9):1195-1204.
Stone et al., "Biochemical characterization of P4-ATPase mutations identified in patients with progressive familial intrahepatic cholestasis," J Biol Chem. 2012, 287(49):41139-51.
Strautnieks et al., "Severe bile salt export pump deficiency: 82 different ABCB11 mutations in 109 families," Gastroenterology, 2008, 134(4):1203-1214.
Sun et al., "Bile acids promote diethyl nitrosamine-induced hepatocellular carcinoma via increased inflammatory signaling," American Journal of Physiology—Gastrointestinal and Liver Physiology, May 5, 2016, 311(1):G91-104.
Suzuki and Takada, "Mechanisms of regulation of bile acid transport in the small intestine," Falk Symposium, 165:76-81, 2009.
Swedish Office Action for Swedish Appln. No. 1850915-8, dated Feb. 15, 2019, 6 pages.
Swedish Search Report for Swedish Appln. No. 1850915-8, dated Feb. 15, 2019, 2 pages.
Takahashi et al., "Gradual improvement of liver function after administration of ursodeoxycholic acid in an infant with a novel ABCB11 gene mutation with phenotypic continuum between BRIC2 and PFIC2," Eur J Gastroenterol Hepatol. 2007, 19(11):942-6.
Tanaka et al., "Genetic and Familial considerations of Primary Binary Cirrhosis," Am. J. Gastroenterology, 2001, 96(1): 8-15.
Tibesar et al., "Two Cases of Progressive Familial Intrahepatic Cholestasis Type 2 Presenting with Severe Coagulopathy without Jaundice," Case Rep Pediatr. 2014, 2014:185923.

(56) References Cited

OTHER PUBLICATIONS

Togawa et al., "Diversity of ATP8B1 mutations in Japanese patients with intrahepatic cholestasis associated with low gamma-glutamyl transpeptidase level," Journal of Pediatric Gastroenterology and Nutrition 2018, 67(1):5363, Abstract No. 615.
Tollefson et al., "A novel class of apical sodium co-dependent bile acid transporter inhibitors: the 1,2-Benzothiazepines", Bioorganic and Medicinal Chemistry Letters 12:3727-3730, 2003.
Treepongkaruna et al., "Novel ABCB11 mutations in a Thai infant with progressive familial intrahepatic cholestasis," World J Gastroenterol. 2009, 15(34):4339-4342.
Tremont et al., "Discovery of Potent, Nonsystemic Apical Sodium-Codependent Bile Acid Transporter Inhibitors (Part 1)," J. Med. Chem, 2005, 48:5837-5852.
Uegaki et al., "Successful treatment with colestimide for a bout of cholestasis in a Japanese patient with benign recurrent intrahepatic cholestasis caused by ATP8B1 mutation," Intern Med. 2008, 47(7):599-602.
Van der Woerd et al., "Analysis of aberrant pre-messenger RNA splicing resulting from mutations in ATP8B1 and efficient in vitro rescue by adapted U1 small nuclear RNA," Hepatology 2015, 61(4):1382-1391.
Van der Woerd et al., "Mutational analysis of ATP8B1 in patients with chronic pancreatitis," PLoS One. 2013, 8(11):e80553.
Van Heek et al., "In vivo metabolism-based discovery of a potent cholesterol absorptions inhibitor, sch58235, in the rat and rhesus monkey through the identification of the active metabolites of sch48461," J. Pharmacol. Exp. Med, 1997, 283(1):157-163.
Van Mil et al., "Benign recurrent intrahepatic cholestasis type 2 is caused by mutations in ABCB11," Gastroenterology. 2004, 127(2):379-384.
Van Tilberg et al., "Na+-dependent bile acid transport in the ileum: the balance between diarrhea and constipation", Gastroenterology 98(1):25-32, 1989.
Varma et al., "Retargeting of bile salt export pump and favorable outcome in children with progressive familial intrahepatic cholestasis type 2," Hepatology 2015, 62(1):198-206.
Vaz et al., "Sodium taurocholate cotransporting polypeptide (SLC10A1) deficiency: conjugated hypercholanemia without a clear clinical phenotype," Hepatology, 2015, 61(1):260-267.
Vertommen and Kinget, "The influence of five selected processing and formulation variables on the particle size, particle size distribution, and friability of pellets produced in a rotary processor," Drug Dev. Ind. Pharm. 1997, vol. 23, p. 39-46.
Vippagunta et al., "Crystalline solids", Advanced Drug Delivery Reviews 48:3-26, 2001.
Vitale et al., "Cryptogenic cholestasis in young and adults: ATP8B1, ABCB11, ABCB4, and TJP2 gene variants analysis by high-throughput sequencing," J Gastroenterol. 2018, 53(8):945-958.
Waisbourd-Zinman et al., "A Rare BSEP Mutation Associated with a Mild Form of Progressive Familial Intrahepatic Cholestasis Type 2," Ann Hepatol. 2017, 16(3):465-468.
Walkowiak-Tomczak, "Characteristics of plums as a raw material with valuable nutritive and dietary properties—a review," Pol. J. Food. Nutr. Sci., 58(4):401-405, 2008.
Wang et al., "Bile acid receptors and liver cancer," Curr. Pathobiol Rep, Mar. 2013, 1(1):29-35.
Wang et al., "Increased hepatocellular carcinoma risk in chronic hepatitis B patients with persistently elevated serum total bile acid: a retrospective cohort study," Scientific reports, Dec. 1, 2016, 6:38180, 9 pages.
Wang, et al., "Splicing analysis of rare/novel synonymous or intronic variants identified in ABCB11 heterozygotes presenting as progressive intrahepatic cholestasis with low γ-glutamyltransferase," Hepatol Res. 2018, 48(7):574-584.
Wang et al., "The Features of GGT in Patients with ATP8B1 or ABCB11 Deficiency Improve the Diagnostic Efficiency," PLoS One. 2016; 11(4):e0153114.
Watts and Illum, "Colonic Drug Delivery," Drug Development and Industrial Pharmacy, 1997, 23(9):893-913.

Welberg et al., "Calcium and the prevention of colon cancer", Scandinavian J. Gasteroenterology Suppl. 188:52-59, 1991.
Whitington et al., "Partial external diversion of bile for the treatment of intractable pruritus associated with intrahepatic cholestasis," Gastroenterology, 95: 1, 130-136, 1988 (Abstract only).
Williams et al., Foye's Principles of Medicinal Chemistry, 5th Edition, 2002, 59-63.
Wolff, "Burger's Medicinal Chemistry, 5ed, Part I", John Wiley & Sons, 1995, pp. 975-977.
Wong et al., "Utility of oligonucleotide array-based comparative genomic hybridization for detection of target gene deletions," Clin Chem. 2008, 54(7)1141-1148.
Woolbright et al., "Novel insight into mechanisms of cholestatic liver injury," World Journal of Gastroenterology, 18: 36, 4985-4993, 2012.
Wu et al., "Discovery of a highly potent, non-absorbable apical sodium-dependent bile acid transporter inhibitor (GSK2330672) for treatment of type 2 diabetes," J. Med. Chem., 2013, 53(12):5094-5117.
Xie et al., "Dysregulated hepatic bile acids collaboratively promote liver carcinogenesis," Int J Cancer, Oct. 15, 2016, 139(8):1764-1775.
Yang et al., "Partial external binary diversion in children with progressive familial intrahepatic cholestasis and alagille disease," Journal of Pediatric Gastroenterology and Nutrition, 49: 216-221, 2009.
Yerushalmi et al., "Bile acid-induced rat hepatocyte apoptosis is inhibited by antioxidants and Mockers of the mitochondrial," Hepatology, 33: 3, 616-626, 2001.
Zarenezhad et al., "Investigation of Common Variations of ABCB4, ATP8B1 and ABCB11 Genes in Patients with Progressive Familial Intrahepatic Cholestasis," Hepatitis Monthly: 2017, 17(2):e43500.
Zhang et al., "Effect of bile duct ligation on bile acid composition in mouse serum and liver," Liver int, 32 58-69, 2012.
Zhang et al., Abcb11 deficiency induces cholestasis coupled to impaired B-Fatty acid oxidation in mice, Journal of biological chemistry, 287: 29, 24784-2479, 2012.
Allison et al., "Studies on mixed populations of human intestinal bacteria grown in single-stage and multistage continuous culture systems," Appl. Environ. Microbial. 1989, 55(3):672-678.
Alvarez, "Development of crystallization processes for pharmaceutical applications," LACCEI, 2007, 2E.3-1-2E.3-9.
Chauhan et al., "Pharmaceutical polymers," Encycl. Biomed. Polymers and Polymeric Biomaterials, 2016, 5929-5942.
Drumond et al., "Patients' appropriateness, acceptability, usability and preferences for pharmaceutical preparations: Results from a literature review on clinical evidence," Int. J. Pharm. 2017, 521(1-2):294-305.
Engelen et al., "Oral size perception of particles: effect of size, type, viscosity and method," J. Text. Studies 2005, 36(4):373-386.
Fuller, "Probiotics in man and animals," Appl. Bacterial. 1989, 66(5):365-378.
Gao et al., "Recent developments in the crystallization process: toward the pharmaceutical industry," Engineering, 2017, 3:343-353.
Gibson and Roberfroid, "Dietary modulation of the human colonic microbiota: introducing the concept of prebiotics," J. Nutr. 1995, 125(6):1401-1412.
International Search Report and Written Opinion in Appln. No. PCT/SE2019/050603, dated Sep. 18, 2019, 11 pages.
Kolter et al., "Structure and dry binding activity of different polymers, including Kollidon VA 64," Drug Development, 2000, 26(11):1159-65.
Kozarewicz, "Regulatory perspectives on acceptability testing of dosage forms in children," Int. J. Pharm. 2014, 469(2):245-248.
Liu, et al., "Patient-centered pharmaceutical design to improve acceptability of medicines: similarities and differences in paediatric and geriatric populations," Drugs 2014, 74(16):1871-1889.
Loh et al., "Overview of milling techniques for improving the solubility of poorly water-soluble drugs," Asian J Pharm Sci., 2015, 10:225-274.
Lopez et al., "Effect of formulation variables on oral grittiness and preferences of multiparticulate formulations in adult volunteers," Eur. J. Pharm. Sci. 2016, 92:156-162.

(56) References Cited

OTHER PUBLICATIONS

Lopez et al., "Formulation approaches to pediatric oral drug delivery: benefits and limitations of current platforms," Expert Opin. Drug Deliv., 2015, 12(11):1727-1740.

Minekus et al., "A computer-controlled system to simulate conditions of the large intestine with peristaltic mixing, water absorption and absorption of fermentation products," Appl. Microbiol Biatechnol. 1999, 53(1):108-114.

Mishra et al., "Investigation of organoleptic characteristics in the development of soft chews of calcium carbonate as mineral supplement," Yakugaku Zasshi 2009, 129(12):1537-1544.

Mistry et al., "Evidence of acceptability of oral paediatric medicines: a review," J. Pharm. Pharmacol. 2017, 69(4):361-376.

Molly et al., "Development of a 5-step multi-chamber reactor as a simulation of the human intestinal microbial system," Appl. Microbiol. Biatechnol. 1993, 39:254-258.

Neuvonen et al., "Activated charcoal in the treatment of hypercholesterolaemia: dose-response relationships and comparison with cholestyramine," Eur J Clin Pharnnacol, 1989, 37(3):225.

Ricci, "Bridging studies in support of oral pediatric formulation development," Int. J. Pharmaceuticals, 2013, 457:323-326.

Swedish Office Action in Swedish Appln. No. 1850761-6, dated Dec. 17, 2018, 8 pages.

Swedish Office Action in Swedish Appln. No. 1850762-4, dated Dec. 27, 2018, 7 pages.

Swedish Search Report in Swedish Appln. No. 1850761-6, dated Dec. 17, 2018, 3 pages.

Swedish Search Report in Swedish Appln. No. 1850762-4, dated Dec. 27, 2018, 3 pages.

Tian et al., "Factors affecting crystallization of hydrates," J. Pharm. Pharmacol., 2010, 62:1534-1546.

Tyle, "Effect of size, shape and hardness of particles in suspension on oral texture and palatability," Acta Psychological 1993, 84(1):111-118.

Walsh et al., "Patient acceptability, safety and access: A balancing act for selecting age-appropriate oral dosage forms for paediatric and geriatric populations," Int. J. Pharm. 2017, 536(2):547-562.

CRYSTAL MODIFICATIONS OF ODEVIXIBAT

CROSS-REFERENCE TO RELATED APPLICATIONS

This application is a Continuation under 35 U.S.C. § 111(a) of International Application No. PCT/SE2019/050602, filed Jun. 20, 2019, which claims priority to Swedish Application No. 1850761-6, filed Jun. 20, 2018, and to Swedish Application No. 1850762-4, filed Jun. 20, 2018, the disclosures of which are incorporated by reference herein in their entireties.

TECHNICAL FIELD

The present invention relates to crystal modifications of 1,1-dioxo-3,3-dibutyl-5-phenyl-7-methylthio-8-(N—{(R)-α-[N—((S)-1-carboxypropyl)carbamoyl]-4-hydroxybenzyl} carbamoylmethoxy)-2,3,4,5-tetrahydro-1,2,5-benzothiadiazepine (odevixibat), more specifically crystal modifications 1 and 2 of odevixibat. The invention also relates to a process for the preparation of crystal modification 1 of odevixibat, to a pharmaceutical composition comprising crystal modification 1, and to the use of this crystal modification in the treatment of various conditions as described herein.

BACKGROUND

The compound 1,1-dioxo-3,3-dibutyl-5-phenyl-7-methylthio-8-(N—{(R)-α-[N—((S)-1-carboxypropyl) carbamoyl]-4-hydroxybenzyl}carbamoylmethoxy)-2,3,4,5-tetrahydro-1,2,5-benzothiadiazepine (odevixibat; also known as A4250) is disclosed in WO 03/022286. The structure of odevixibat is shown below.

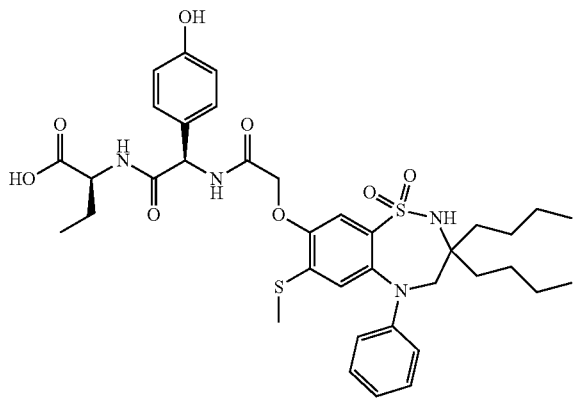 [SMILES: CCCCC1(CCCC)CN(c2ccccc2)c2cc(SC)c(OCC(=O)N[C@@H](C(=O)N[C@@H](CC)C(=O)O)c3ccc(O)cc3)cc2S(=O)(=O)N1]

As an inhibitor of the ileal bile acid transporter (IBAT) mechanism, odevixibat inhibits the natural reabsorption of bile acids from the ileum into the hepatic portal circulation. Bile acids that are not reabsorbed from the ileum are instead excreted into the faeces. The overall removal of bile acids from the enterohepatic circulation leads to a decrease in the level of bile acids in serum and the liver. Odevixibat, or a pharmaceutically acceptable salt thereof, is therefore useful in the treatment or prevention of diseases such as dyslipidemia, constipation, diabetes and liver diseases, and especially liver diseases that are associated with elevated bile acid levels.

According to the experimental section of WO 03/022286, the last step in the preparation of odevixibat involves the hydrolysis of a tert-butyl ester under acidic conditions. The crude compound was obtained by evaporation of the solvent under reduced pressure followed by purification of the residue by preparative HPLC (Example 29). No crystalline material was identified.

Amorphous materials may contain high levels of residual solvents, which is highly undesirable for materials that should be used as pharmaceuticals. Also, because of their lower chemical and physical stability, as compared with crystalline material, amorphous materials may display faster decomposition and may spontaneously form crystals with a variable degree of crystallinity. This may result in unreproducible solubility rates and difficulties in storing and handling the material. In pharmaceutical preparations, the active pharmaceutical ingredient (API) is for that reason preferably used in a highly crystalline state. Thus, there is a need for crystal modifications of odevixibat having improved properties with respect to stability, bulk handling and solubility. In particular, it is an object of the present invention to provide a stable crystal modification of odevixibat that does not contain high levels of residual solvents, that has improved chemical stability and can be obtained in high levels of crystallinity.

SUMMARY OF THE INVENTION

The invention provides crystal modifications of odevixibat. In a first aspect, the crystal modification is a crystalline hydrate of odevixibat. This crystalline hydrate is a channel hydrate, which may contain up to 2 moles of water associated with the crystal per mole of odevixibat. The amount of water calculated herein excludes water adsorbed to the surface of the crystal. In one embodiment, the crystalline hydrate is a sesquihydrate, i.e., contains about 1.5 moles of water associated with the crystal per mole of odevixibat. In another aspect, which may be related to the first aspect, the invention provides crystal modification 1 of odevixibat. Crystal modification 1 is a stable crystalline hydrate which at 30% relative humidity (RH) contains about 1.5 moles of water per mole of odevixibat.

In another aspect, the invention provides a dihydrate-disolvate of odevixibat. This mixed solvate can exist as different isostructural solvates and may comprise methanol, ethanol, 2-propanol, acetone, acetonitrile, 1,4-dioxane, DMF or DMSO as the organic solvent. When the mixed solvate is dried, it loses its solvate molecules and transforms into crystal modification 1 of odevixibat. In another aspect, which may be related to this aspect, the invention provides crystal modifications 2A, 2B and 2C of odevixibat, herein collectively referred to as crystal modification 2 of odevixibat. Upon drying, crystal modification 2 loses its organic solvent molecules and generates crystal modification 1 of odevixibat.

The invention further provides the use of crystal modification 1 of odevixibat in the treatment of a condition described herein, a pharmaceutical composition comprising crystal modification 1 of odevixibat, as well as a process for the preparation of crystal modification 1 of odevixibat.

DETAILED DESCRIPTION OF THE INVENTION

Figure 1:
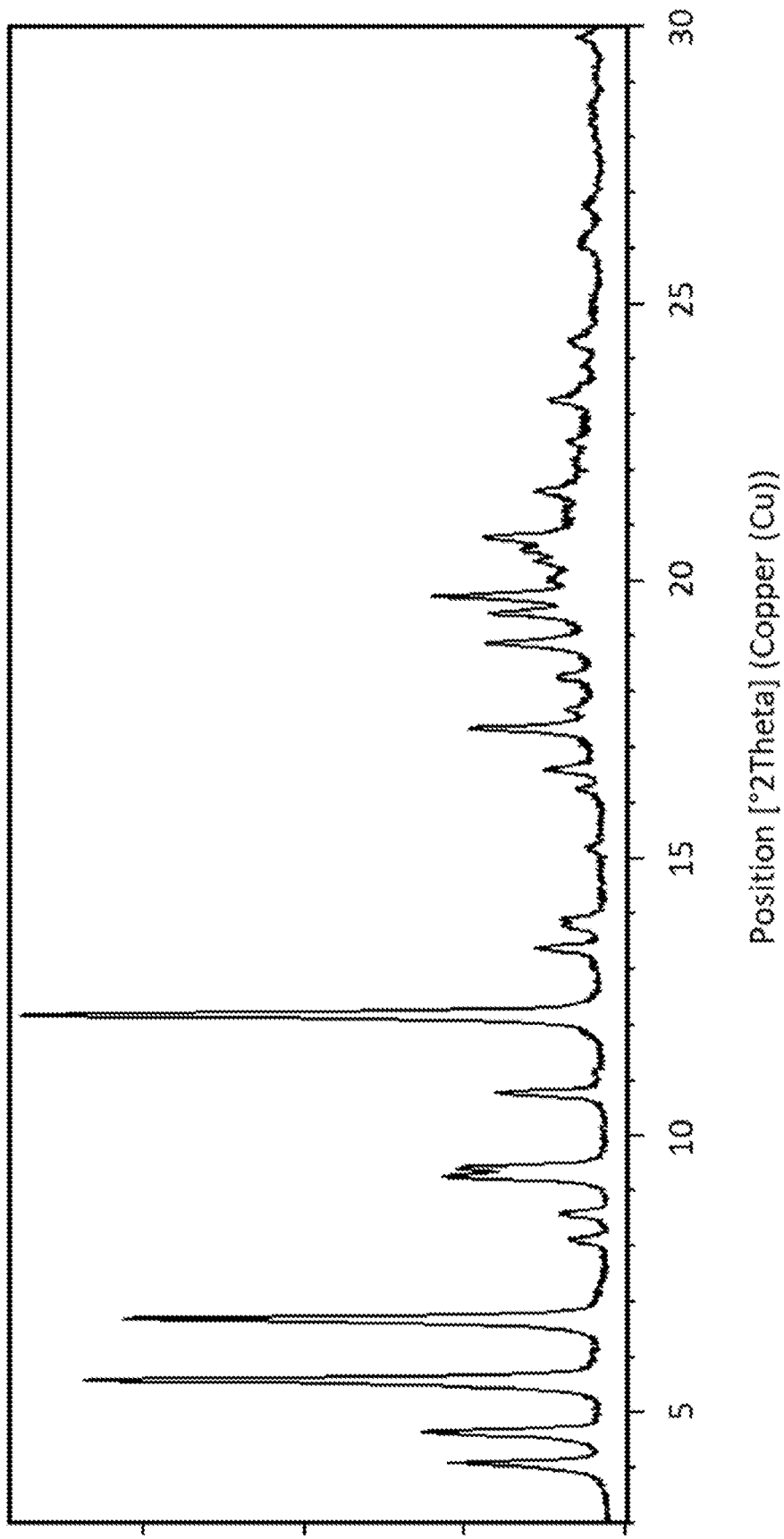
FIG. 1 shows the X-ray powder diffractogram of dried crystal modification 1.

The invention described herein relates to crystal modifications that were discovered in extensive studies on odevixibat. It has been observed that odevixibat can crystallize from a variety of organic solvents (or mixtures of solvents) by incorporating solvate molecules in its structure, thereby forming various solvates or mixed solvates. While most of these (mixed) solvates are unstable in air and become amorphous upon drying, it has surprisingly been discovered that certain mixed solvates of odevixibat could be dried and transformed into a stable crystalline form of odevixibat. It is remarkable that this stable form, hereinafter referred to as crystal modification 1 of odevixibat, can be formed from different mixed solvates of odevixibat.

Thus, in a first aspect, the invention relates to crystal modification 1 of odevixibat. This stable crystal modification can be obtained from a slurry of odevixibat in a mixture of water and an organic solvent such as ethanol. Under these conditions, a mixed solvate containing about two moles of water and about one to about three, such as about two to about three, moles of ethanol per mole of odevixibat (e.g., a dihydrate-diethanolate or a dihydrate-triethanolate) is initially formed. In some embodiments, this mixed solvate is referred to as crystal modification 2. When the mixed solvate is dried, it loses its organic solvent molecules and becomes crystal modification 1. While not wishing to be bound by theory, it is believed that the solvent molecules can be removed without dissolution and recrystallization of the crystals.

Crystal modification 1 contains void volumes that are capable of containing up to about 2 moles of water associated with the crystal per mole of odevixibat, depending on the relative humidity. This form is therefore formally a channel hydrate. At about 30% relative humidity, however, crystal modification 1 contains a substantially stoichiometric amount of about 1.5 moles of water per mole of organic compound and is thus a sesquihydrate. The substantially stoichiometric amount of water is considered advantageous, as the water content of the crystals remains substantially constant even with humidity changes within the normal relative humidity range of about 30% to about 70% RH.

Indeed, at normal humidities, such as between about 30 and about 70% RH, crystal modification 1 exhibits relatively low hygroscopicity.

In one embodiment, the invention relates to crystal modification 1 of odevixibat having an X-ray powder diffraction (XRPD) pattern, obtained with CuKα1-radiation, with at least specific peaks at °2θ positions 5.6±0.2, 6.7±0.2 and/or 12.1±0.2.

In a specific embodiment thereof, the invention relates to crystal modification 1 having an XRPD pattern, obtained with CuKα1-radiation, with specific peaks at °2θ positions 5.6±0.2, 6.7±0.2 and 12.1±0.2 and one or more of the characteristic peaks: 4.1±0.2, 4.6±0.2, 9.3±0.2, 9.4±0.2 and 10.7±0.2.

In a more specific embodiment thereof, the invention relates to crystal modification 1 having an XRPD pattern, obtained with CuKα1-radiation, with specific peaks at °2θ positions 4.6±0.2, 5.6±0.2, 6.7±0.2, 9.3±0.2, 9.4±0.2 and 12.1±0.2.

In a yet more specific embodiment thereof, the invention relates to crystal modification 1 having an XRPD pattern, obtained with CuKα1-radiation, with characteristic peaks at °2θ positions 4.1±0.2, 4.6±0.2, 5.6±0.2, 6.7±0.2, 9.3±0.2, 9.4±0.2, 10.7±0.2 and 12.1±0.2, and one or more of 8.1±0.2, 8.6±0.2, 13.4±0.2, 13.8±0.2, 13.9±0.2, 16.6±0.2, 17.3±0.2, 17.7±0.2, 18.3±0.2, 18.9±0.2, 19.4±0.2, 19.7±0.2, 20.5±0.2, 20.8±0.2, 21.6±0.2, 23.2±0.2, 24.3±0.2, 29.8±0.2 and 30.6±0.2.

In a yet even more specific embodiment thereof, the invention relates to crystal modification 1 having an XRPD pattern, obtained with CuKα1-radiation, with characteristic peaks at °2θ positions 4.1±0.2, 4.6±0.2, 5.6±0.2, 6.7±0.2, 8.1±0.2, 8.6±0.2, 9.3±0.2, 9.4±0.2, 10.7±0.2, 12.1±0.2, 13.4±0.2, 13.8±0.2, 13.9±0.2, 16.6±0.2, 17.3±0.2, 17.7±0.2, 18.3±0.2, 18.9±0.2, 19.4±0.2, 19.7±0.2, 20.5±0.2, 20.8±0.2, 21.6±0.2, 23.2±0.2, 24.3±0.2, 29.8±0.2 and 30.6±0.2.

In a particular embodiment, the invention relates to crystal modification 1 having an XRPD pattern, obtained with CuKα1-radiation, substantially as shown in FIG. 1.

Whereas crystal modification 1 is a sesquihydrate containing about 3.5% (w/w) water at about 30% relative humidity (based on the total crystal weight), it has been observed that the crystal can take up an additional 1.5% (w/w) water when the humidity is increased up to 95% RH. The sorption and desorption of this additional water is fully reversible (see e.g. Example 10). The additional water may be adsorbed on the surface or may further fill the channels of the structure. In some embodiments, the term "overhydrated" refers to crystal modification 1 containing from about 1.5 to about 4 moles of water per mole of odevixibat, such as from about 1.5 to about 3.5, or such as from about 1.5 to 3, or such as from about 1.5 to about 2.5, or such as from about 1.5 to about 2 moles of water per mole of odevixibat. In some embodiments, the term "overhydrated" refers to crystal modification 1 containing from about 2 to about 4 moles of water per mole of odevixibat, such as from about 2 to about 3.5, or such as from about 2 to about 3, or such as from about 2 to 2.5 moles of water per mole of odevixibat.

Figure 3:
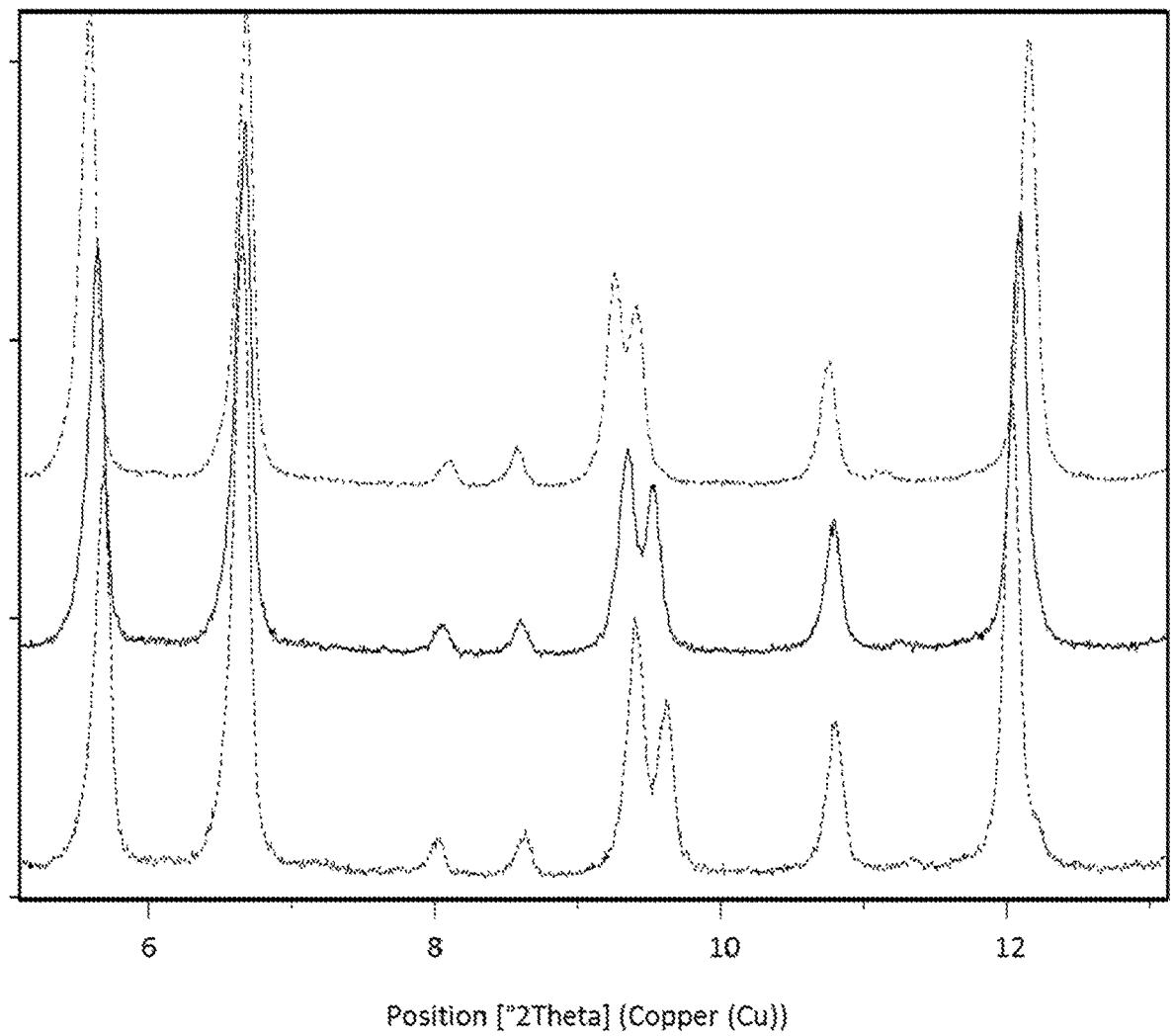
FIG. 3 shows the drying of crystal modification 1, with the X-ray powder diffractogram of an overhydrated sample of crystal modification 1 at the bottom and of a dried sample at the top (2θ range 5-13°).
Figure 4:
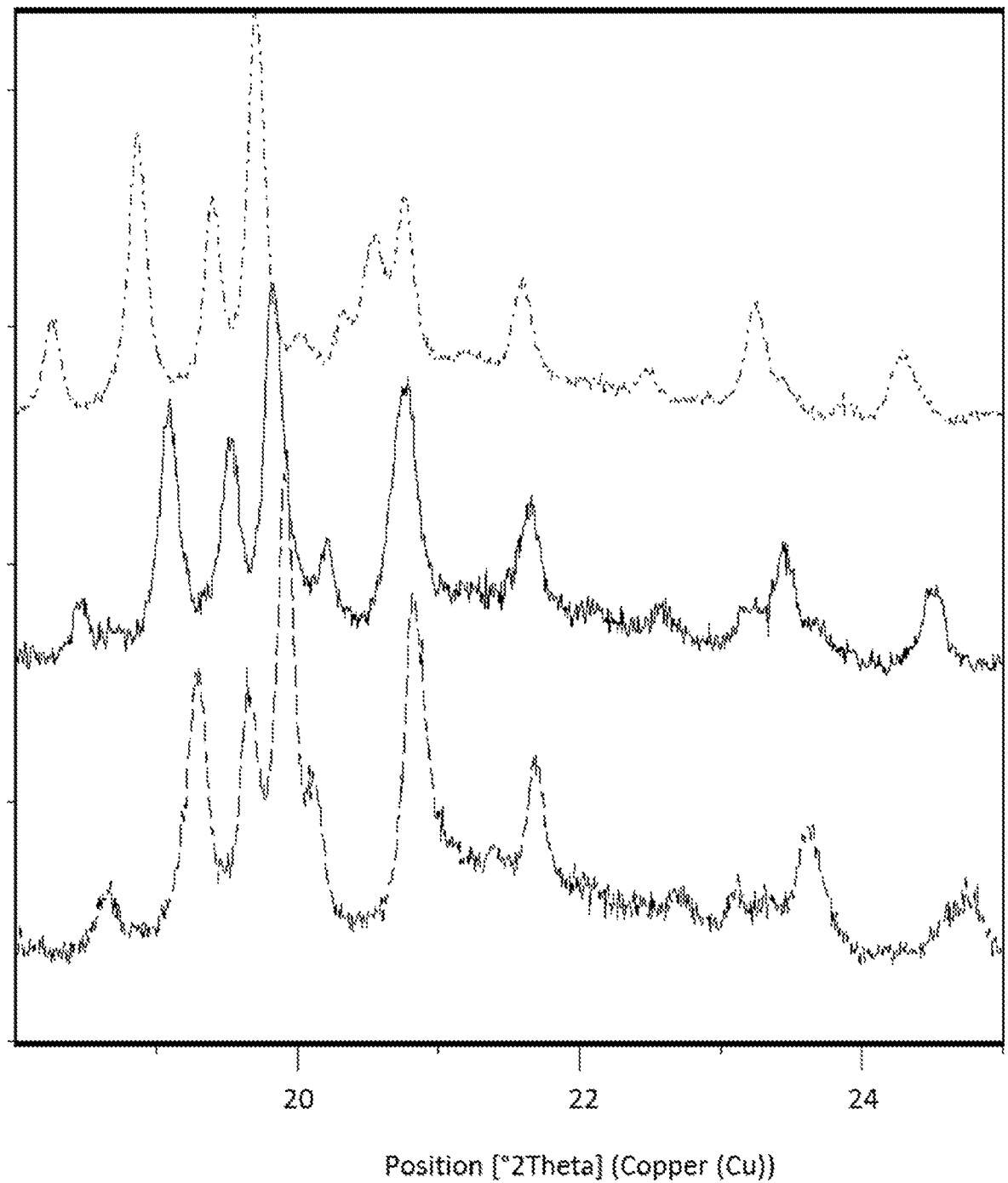
FIG. 4 shows the drying of crystal modification 1, with the X-ray powder diffractogram of an overhydrated sample of crystal modification 1 at the bottom and of a dry sample at the top (2θ range 18-25°).

It has been observed that the XRPD pattern of overhydrated crystal modification 1 slightly changes when it is dried, e.g. at 50° C. in vacuum. A small shift of peaks is most clearly seen in the 2θ ranges 5-13° and 18-25°, as shown in FIGS. 3 and 4, respectively. Exposing the dried modification to elevated relative humidity, such as up to 95% RH, makes the XRPD pattern of the overhydrated modification appear again. The peak shifts are a result of the unit cell volume changes, which occur as water molecules go in and out of the crystal structure.

Therefore, in another embodiment, the invention relates to overhydrated crystal modification 1 having an X-ray powder diffraction (XRPD) pattern, obtained with CuKα1-radiation, with at least specific peaks at °2θ positions 5.7±0.2, 6.7±0.2 and/or 12.0±0.2.

In certain embodiments, the invention relates to overhydrated crystal modification 1 having an XRPD pattern, obtained with CuKα1-radiation, with specific peaks at °2θ positions 5.7±0.2, 6.7±0.2 and 12.0±0.2 and one or more of the characteristic peaks: 4.0±0.2, 9.4±0.2, 9.6±0.2 and 10.8±0.2.

In a more particular embodiment, the invention relates to overhydrated crystal modification 1 having an XRPD pattern, obtained with CuKα1-radiation, with specific peaks at °2θ positions 4.0±0.2, 5.7±0.2, 6.7±0.2, 9.4±0.2, 9.6±0.2, 10.8±0.2 and 12.1±0.2.

In a further embodiment, the invention relates to overhydrated crystal modification 1 having an XRPD pattern, obtained with CuKα1-radiation, with characteristic peaks at °2θ positions 4.0±0.2, 5.7±0.2, 6.7±0.2, 9.4±0.2, 9.6±0.2, 10.8±0.2 and 12.1±0.2, and one or more of 4.7±0.2, 8.0±0.2, 8.6±0.2, 13.3±0.2, 14.1±0.2, 15.3±0.2, 16.5±0.2, 17.3±0.2, 19.3±0.2, 19.7±0.2, 19.9±0.2, 20.1±0.2, 20.8±0.2, 21.7±0.2, 23.6±0.2, 26.2±0.2, 26.5±0.2, 28.3±0.2 and 30.9±0.2.

In a yet further embodiment, the invention relates to overhydrated crystal modification 1 having an XRPD pattern, obtained with CuKα1-radiation, with characteristic peaks at °2θ positions 4.0±0.2, 4.7±0.2, 5.7±0.2, 6.7±0.2, 8.0±0.2, 8.6±0.2, 9.4±0.2, 9.6±0.2, 10.8±0.2, 12.1±0.2, 13.3±0.2, 14.1±0.2, 15.3±0.2, 16.5±0.2, 17.3±0.2, 19.3±0.2, 19.7±0.2, 19.9±0.2, 20.1±0.2, 20.8±0.2, 21.7±0.2, 23.6±0.2, 26.2±0.2, 26.5±0.2, 28.3±0.2 and 30.9±0.2.

Figure 2:
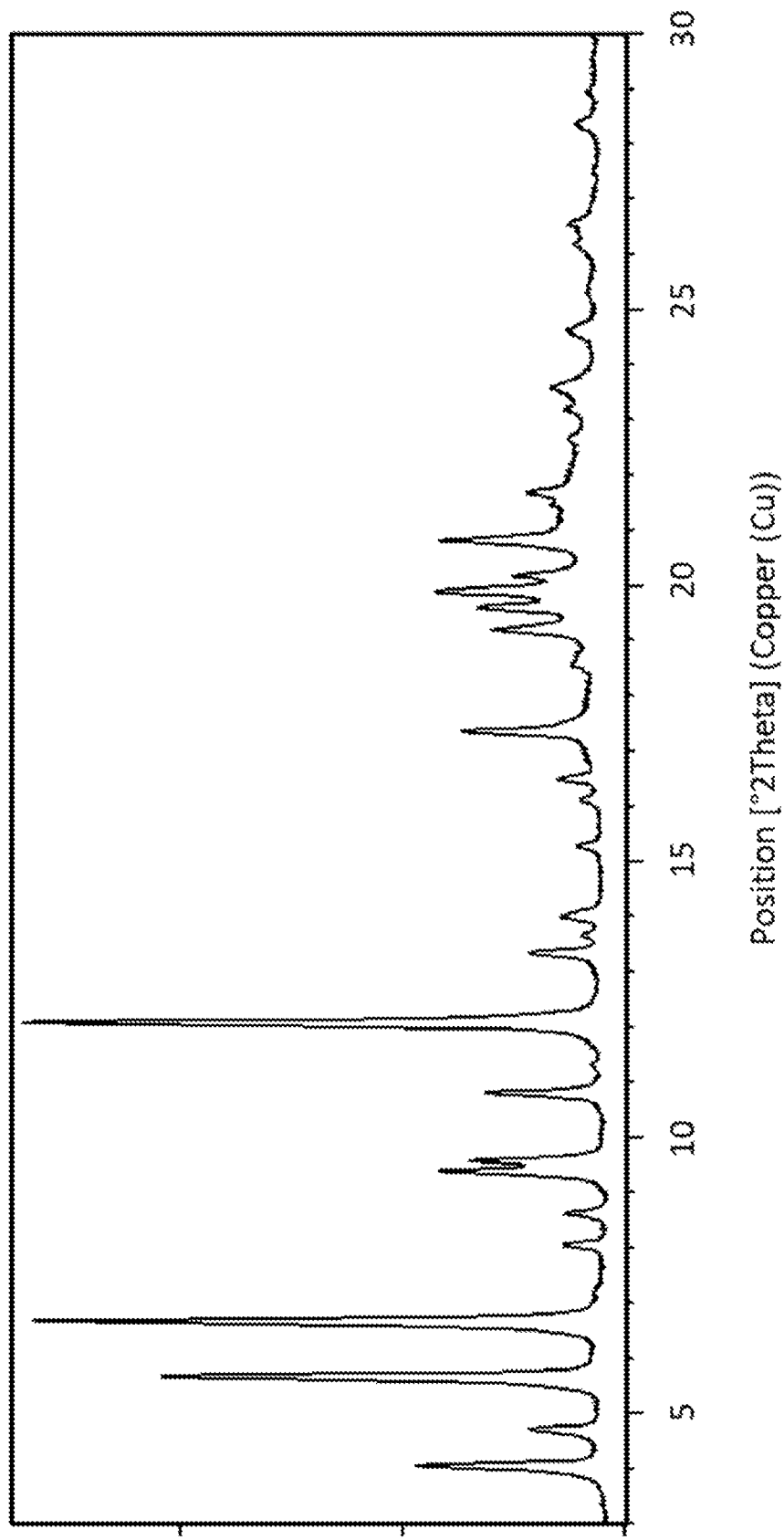
FIG. 2 shows the X-ray powder diffractogram of an overhydrated sample of crystal modification 1.

In yet another embodiment, the invention relates to overhydrated crystal modification 1 of odevixibat having an XRPD pattern, obtained with CuKα1-radiation, substantially as shown in FIG. 2.

In some embodiments, the crystallinity of crystal modification 1 is greater than about 99%. The crystallinity may be measured by Differential Scanning Calorimetry (DSC) methods, e.g. as disclosed in the experimental section.

Crystal modification 1 has several advantages over amorphous odevixibat. The relatively low hygroscopicity of crystal modification 1 at normal humidities, such as 30-70% RH, facilitates the handling and storing of odevixibat. Additionally, crystal modification 1 does not contain high levels of residual solvents. In contrast, it has been observed that batches of crude, amorphous odevixibat can contain residual solvents (such as formic acid) at levels that exceed the regulatory limits by far. Stability experiments have further shown that crystal modification 1 of odevixibat displays a higher chemical stability than amorphous odevixibat.

Crystal modification 1 may possess one or more additional advantages, such as a higher physical and thermodynamic stability than amorphous odevixibat; a more reproducible solubility than amorphous odevixibat; or an improved ability to process into a formulation. Such properties are highly relevant for pharmaceutical formulations of odevixibat.

In a second aspect, the invention relates to crystal modification 2 of odevixibat. It has been discovered that crystal modification 2 may be obtained not only from a mixture of ethanol and water, as described above, but also from methanol and certain other mixtures of solvent and water, including mixtures of methanol and water, 2-propanol and water, acetone and water, acetonitrile and water, 1,4-dioxane and water, DMF and water and DMSO and water. Crystal modification 2 is a mixed solvate, containing about two moles of water and about one to about three moles of organic solvent per mole of odevixibat. In some embodiments, the mixed solvate includes about 1.7 to about 2.3, about 1.8 to about 2.2, about 1.9 to about 2.1 or about 1.95 to about 2.05 moles of water associated with each mole of odevixibat in a crystal (excluding any water that may be adsorbed to the surface of the crystal).

Interestingly, the XRPD patterns for the crystal modifications obtained from these different mixtures are essentially the same (see FIGS. 6-12). It is therefore believed that crystal modification 2 can exist as different isostructural solvates (also known as isomorphic solvates). In these isostructural solvates, crystal modification 2 accommodates different solvents (as a mixture with water). The presence of different solvents causes small volume changes to the unit cell but does not otherwise result in any significant distortion of the crystal structure of crystal modification 2. Nevertheless, the XRPD patterns for the isostructural solvates may be slightly different. Three similar, yet slightly different forms of crystal modification 2 are herein referred to as crystal modifications 2A, 2B and 2C, and collectively as "crystal modification 2". Significantly, it has been found that upon drying, crystal modifications 2A, 2B and 2C can form crystal modification 1, regardless of the solvent mixture from which crystal modification 2 was crystallized.

In a first embodiment, the crystalline mixed solvate is crystal modification 2A, as obtained from a mixture of ethanol and water, acetone and water, 1,4-dioxane and water, DMF and water or 2-propanol and water, having an X-ray powder diffraction (XRPD) pattern, obtained with CuKα1-radiation, with at least specific peaks at °2θ positions 5.0±0.2, 5.1±0.2 and/or 11.8±0.2.

In a specific embodiment thereof, the invention relates to crystal modification 2A, as obtained from a mixture of ethanol and water, acetone and water, 1,4-dioxane and water, DMF and water or 2-propanol and water, having an XRPD pattern, obtained with CuKα1-radiation, with specific peaks at °2θ positions 5.0±0.2, 5.1±0.2 and 11.8±0.2 and one or more of the characteristic peaks: 6.4±0.2, 6.6±0.2 and 9.5±0.2.

In a more specific embodiment thereof, the invention relates to crystal modification 2A, as obtained from a mixture of ethanol and water, acetone and water, 1,4- dioxane and water, DMF and water or 2-propanol and water, having an XRPD pattern, obtained with CuKα1-radiation, with specific peaks at °2θ positions 5.0±0.2, 5.1±0.2, 6.4±0.2, 6.6±0.2, 9.5±0.2 and 11.8±0.2.

In a yet more specific embodiment thereof, the invention relates to crystal modification 2A, as obtained from a mixture of ethanol and water, having an XRPD pattern, obtained with CuKα1-radiation, with characteristic peaks at °2θ 5.0±0.2, 5.1±0.2, 6.4±0.2, 6.6±0.2, 9.5±0.2 and 11.8±0.2, and one or more of 5.9±0.2, 8.8±0.2, 9.8±0.2, 10.1±0.2, 11.0±0.2, 11.2±0.2, 11.4±0.2, 12.7±0.2, 13.9±0.2, 14.7±0.2, 15.1±0.2, 15.8±0.2, 16.3±0.2, 17.2±0.2, 17.9±0.2, 19.7±0.2, 20.2±0.2, 20.7±0.2, 21.3±0.2, 22.1±0.2, 22.5±0.2, 22.9±0.2, 23.2±0.2, 23.6±0.2, 24.0±0.2, 24.1±0.2, 24.7±0.2, 25.3±0.2, 26.7±0.2, 26.9±0.2, 29.8±0.2, 30.4±0.2, 30.8±0.2 and 31.6±0.2.

In a yet even more specific embodiment thereof, the invention relates to crystal modification 2A, as obtained from a mixture of ethanol and water, having an XRPD pattern, obtained with CuKα1-radiation, with characteristic peaks at °2θ positions 5.0±0.2, 5.1±0.2, 5.9±0.2, 6.4±0.2, 6.6±0.2, 8.8±0.2, 9.5±0.2, 9.8±0.2, 10.1±0.2, 11.0±0.2, 11.2±0.2, 11.4±0.2, 11.8±0.2, 12.7±0.2, 13.9±0.2, 14.7±0.2, 15.1±0.2, 15.8±0.2, 16.3±0.2, 17.2±0.2, 17.9±0.2, 19.7±0.2, 20.2±0.2, 20.7±0.2, 21.3±0.2, 22.1±0.2, 22.5±0.2, 22.9±0.2, 23.2±0.2, 23.6±0.2, 24.0±0.2, 24.1±0.2, 24.7±0.2, 25.3±0.2, 26.7±0.2, 26.9±0.2, 29.8±0.2, 30.4±0.2, 30.8±0.2 and 31.6±0.2.

Figure 6:
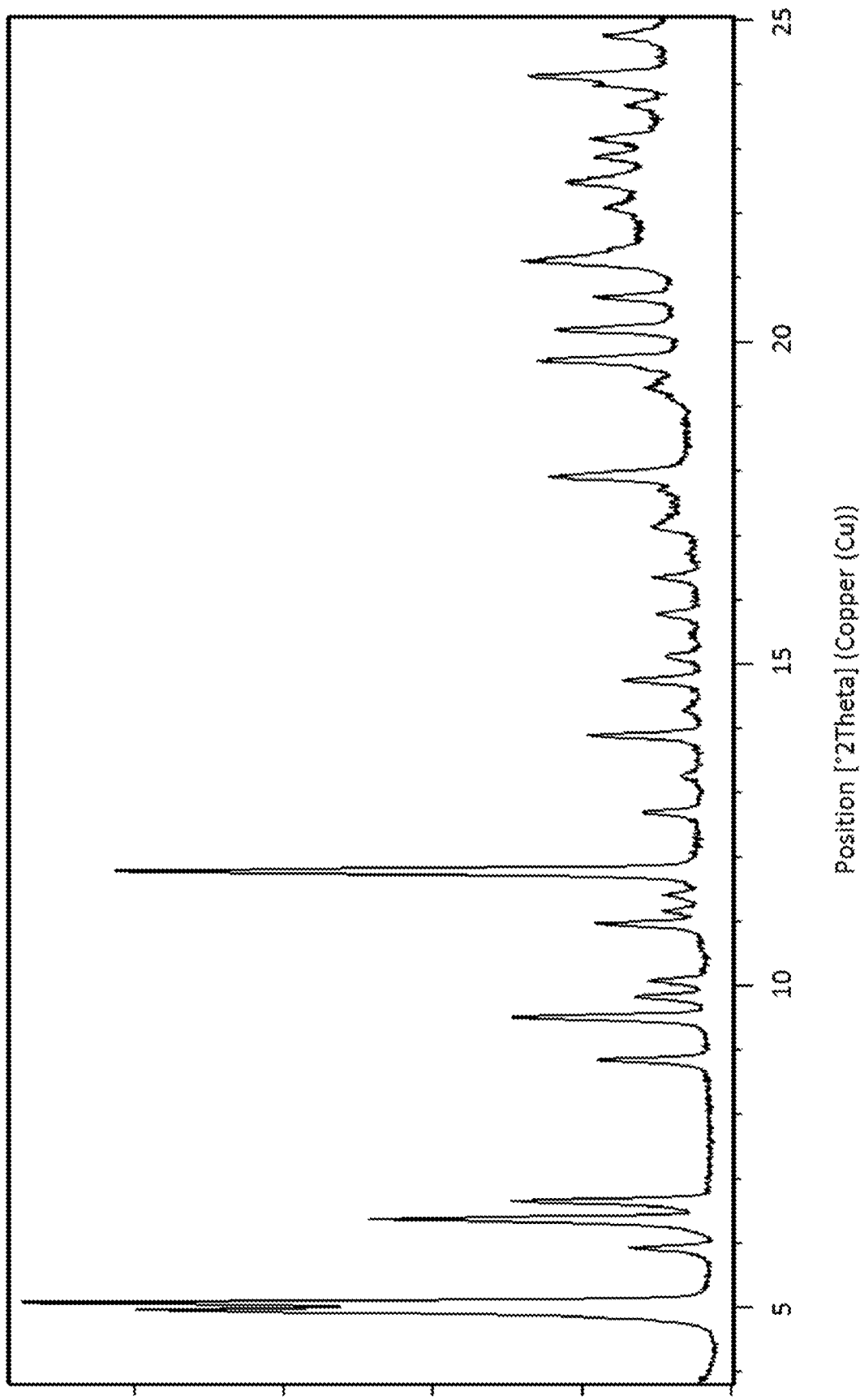
FIG. 6 shows the X-ray powder diffractogram of crystal modification 2A, as obtained from a mixture of ethanol and water (70:30% v/v).

In one particular embodiment, the invention relates to crystal modification 2A, as obtained from a mixture of ethanol and water, having an XRPD pattern, obtained with CuKα1-radiation, substantially as shown in FIG. 6.

Figure 7:
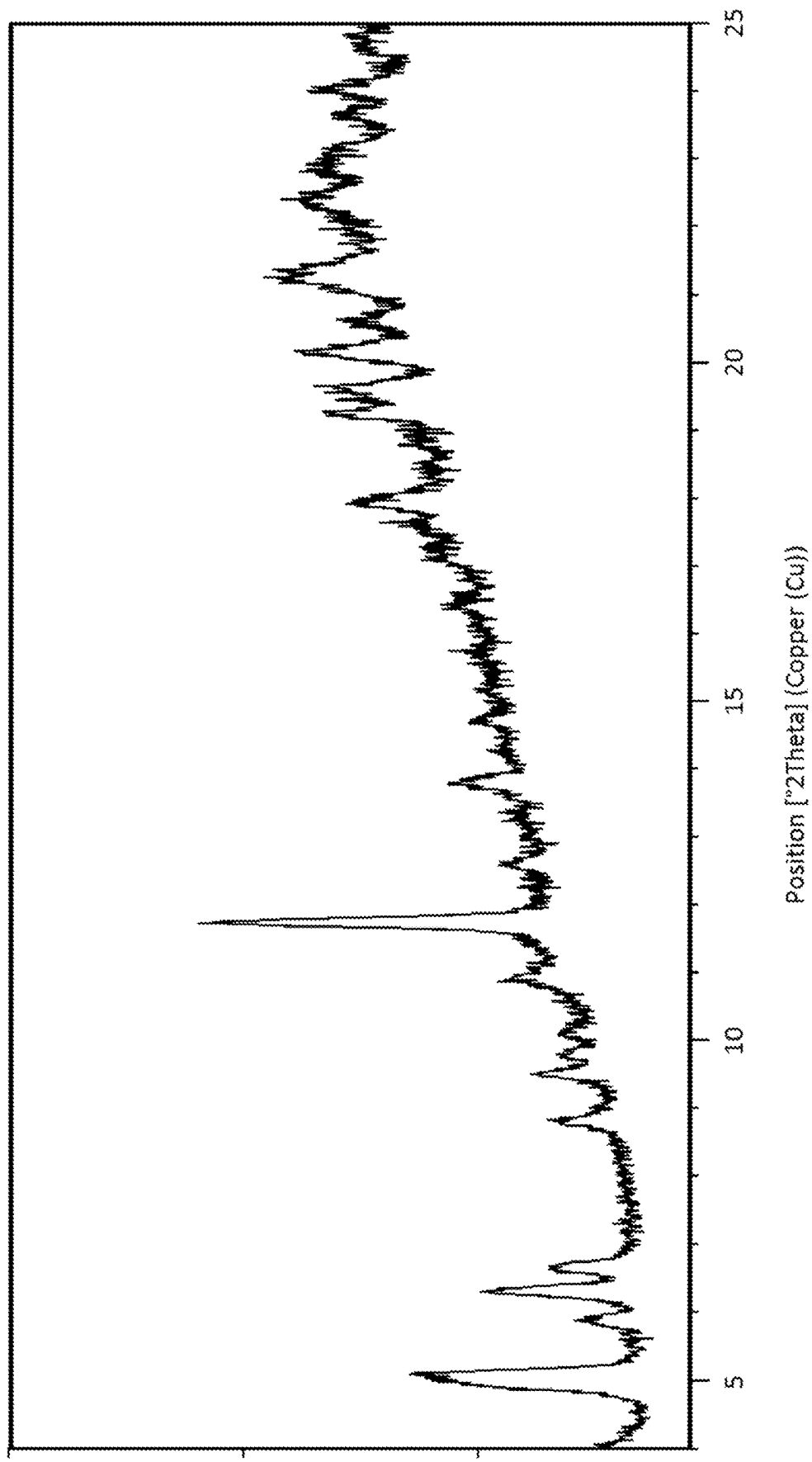
FIG. 7 shows the X-ray powder diffractogram of crystal modification 2A, as obtained from a mixture of acetone and water (50:50% v/v).

In another particular embodiment, the invention relates to crystal modification 2A, as obtained from a mixture of acetone and water, having an XRPD pattern, obtained with CuKα1-radiation, substantially as shown in FIG. 7.

Figure 8:
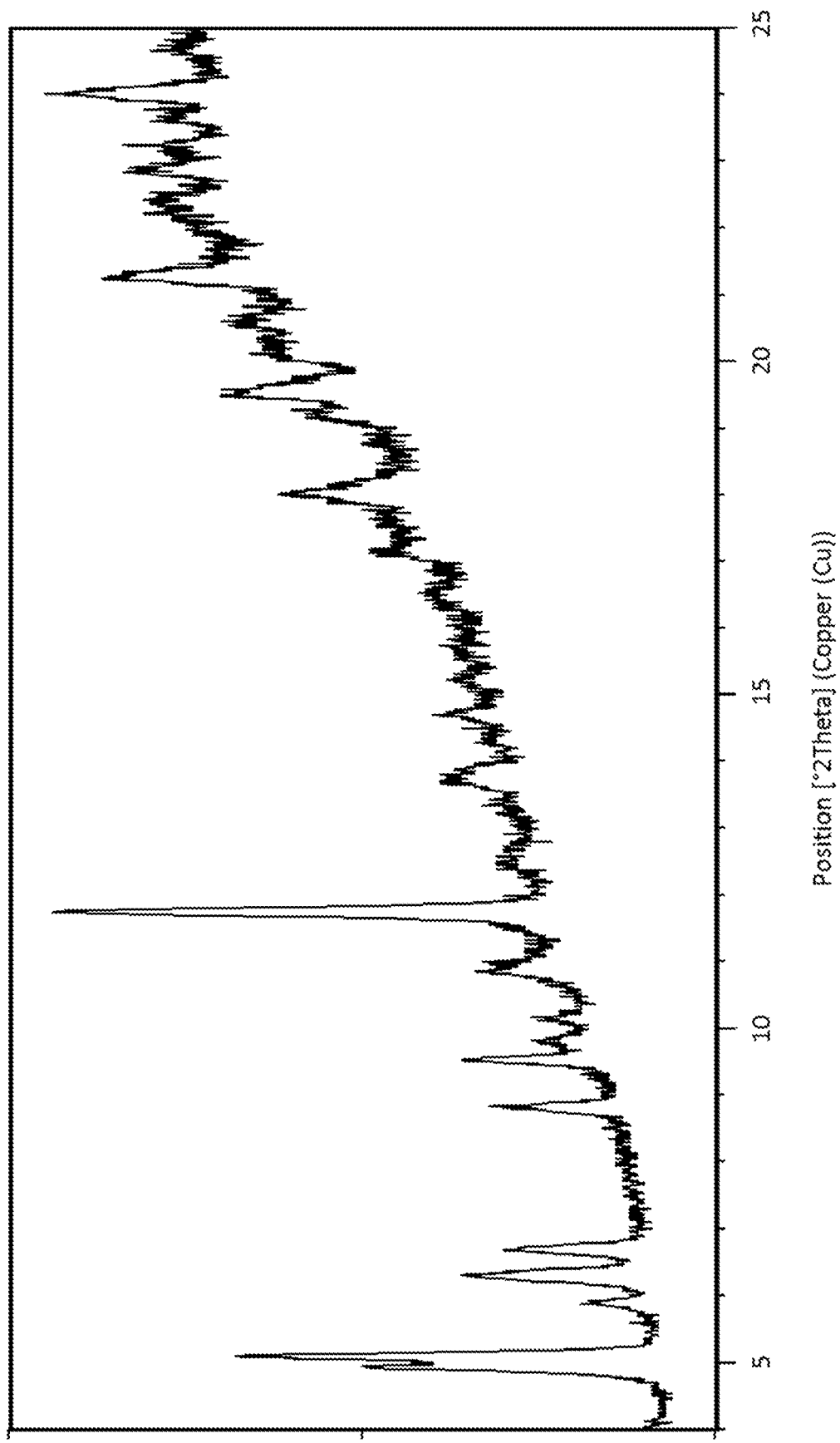
FIG. 8 shows the X-ray powder diffractogram of crystal modification 2A, as obtained from a mixture of 2-propanol and water (50:50% v/v).

In yet another particular embodiment, the invention relates to crystal modification 2A, as obtained from a mixture of 2-propanol and water, having an XRPD pattern, obtained with CuKα1-radiation, substantially as shown in FIG. 8.

Figure 9:
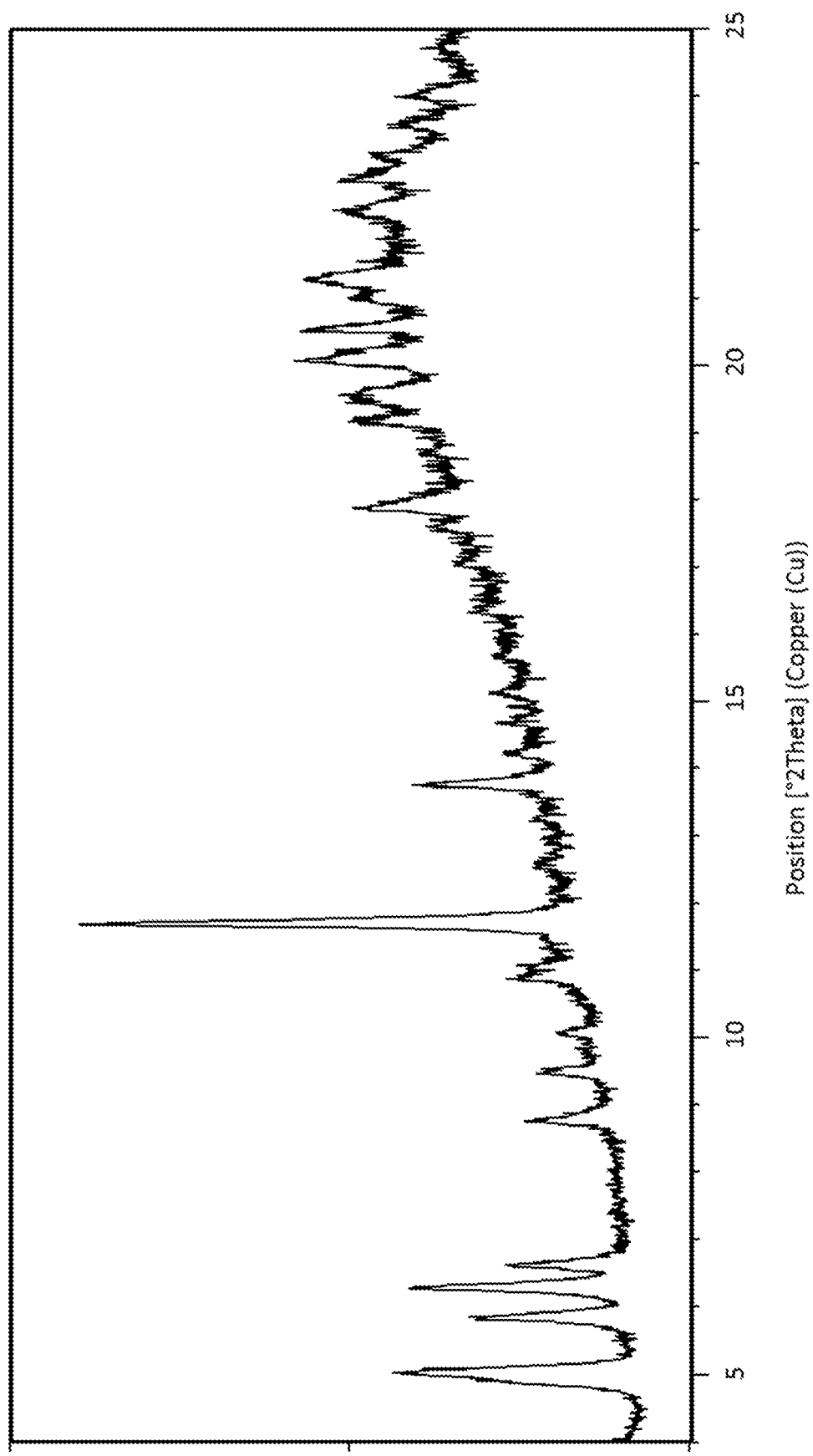
FIG. 9 shows the X-ray powder diffractogram of crystal modification 2A, as obtained from a mixture of 1,4-dioxane and water (50:50% v/v).

In yet another particular embodiment, the invention relates to crystal modification 2A, as obtained from a mixture of 1,4-dioxane and water, having an XRPD pattern, obtained with CuKα1-radiation, substantially as shown in FIG. 9.

In a second embodiment, the crystalline mixed solvate is crystal modification 2B, as obtained from methanol or from a mixture of methanol and water or acetonitrile and water, having an X-ray powder diffraction (XRPD) pattern, obtained with CuKα1-radiation, with at least specific peaks at °2θ positions 4.8±0.2, 5.1±0.2 and/or 11.6±0.2.

In a specific embodiment, the invention relates to crystal modification 2B, as obtained from methanol or from a mixture of methanol and water or acetonitrile and water, having an XRPD pattern, obtained with CuKα1-radiation, with specific peaks at °2θ positions 4.8±0.2, 5.1±0.2 and 11.6±0.2 and one or more of the characteristic peaks: 6.2±0.2, 6.7±0.2, 9.5±0.2 and 20.3±0.2.

In a more specific embodiment thereof, the invention relates to crystal modification 2B, as obtained from methanol or from a mixture of methanol and water or acetonitrile and water, having an XRPD pattern, obtained with CuKα1-radiation, with specific peaks at °2θ positions 4.8±0.2, 5.1±0.2, 6.2±0.2, 6.7±0.2, 9.5±0.2, 11.6±0.2 and 20.3±0.2.

In a yet more specific embodiment thereof, the invention relates to crystal modification 2B, obtained from methanol and water, having an XRPD pattern, obtained with CuKα1-radiation, with characteristic peaks at °2θ positions 4.8±0.2, 5.1±0.2, 6.2±0.2, 6.7±0.2, 9.5±0.2, 11.6±0.2 and 20.3±0.2, and one or more of 5.8±0.2, 8.7±0.2, 9.7±0.2, 10.1±0.2, 10.7±0.2, 11.5±0.2, 13.4±0.2, 13.5±0.2, 14.4±0.2, 14.5±0.2, 15.2±0.2, 16.5±0.2, 16.8±0.2, 19.4±0.2, 20.6±0.2, 21.2±0.2, 21.5±0.2, 23.8±0.2, 23.9±0.2, 25.4±0.2, 26.3±0.2, 26.7±0.2, 30.1±0.2 and 30.6±0.2.

In a yet even more specific embodiment thereof, the invention relates to crystal modification 2B, obtained from methanol and water, having an XRPD pattern, obtained with CuKα1-radiation, with characteristic peaks at °2θ positions 4.8±0.2, 5.1±0.2, 5.8±0.2, 6.2±0.2, 6.7±0.2, 8.7±0.2, 9.5±0.2, 9.7±0.2, 10.1±0.2, 10.7±0.2, 11.5±0.2, 11.6±0.2, 13.4±0.2, 13.5±0.2, 14.4±0.2, 14.5±0.2, 15.2±0.2, 16.5±0.2, 16.8±0.2, 19.4±0.2, 20.3±0.2, 20.6±0.2, 21.2±0.2, 21.5±0.2, 23.8±0.2, 23.9±0.2, 25.4±0.2, 26.3±0.2, 26.7±0.2, 30.1±0.2 and 30.6±0.2.

Figure 10:
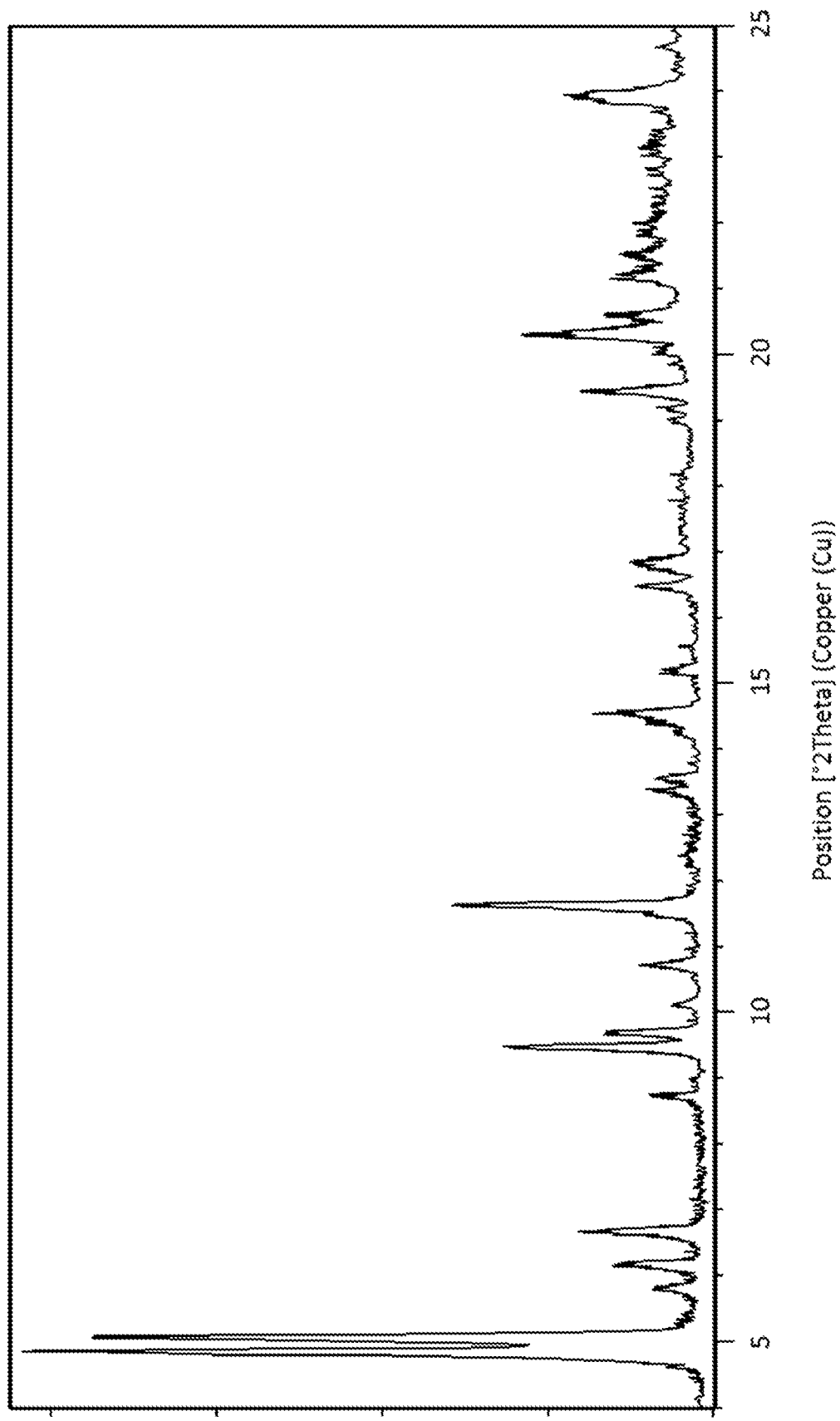
FIG. 10 shows the X-ray powder diffractogram of crystal modification 2B, as obtained from methanol. The water that is necessary for form 2 to crystallize was obtained from the air, as a result of the hygroscopicity of methanol.

In one particular embodiment, the invention relates to crystal modification 2B, as obtained from methanol, having an XRPD pattern, obtained with CuKα1-radiation, substantially as shown in FIG. 10.

Figure 11:
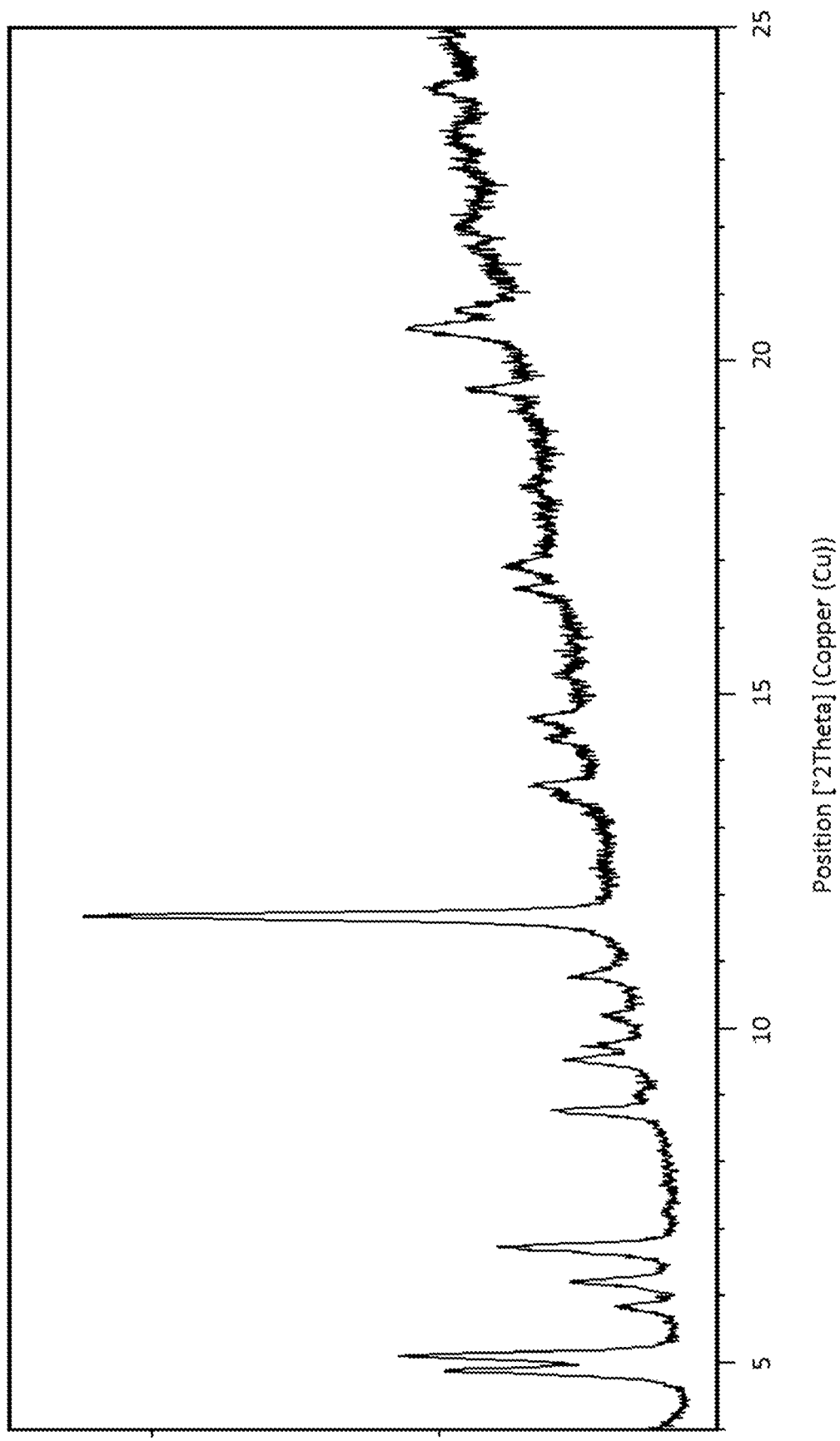
FIG. 11 shows the X-ray powder diffractogram of crystal modification 2B, as obtained from a mixture of acetonitrile and water (40:60% v/v).

In another particular embodiment, the invention relates to crystal modification 2B, as obtained from a mixture of acetonitrile and water, having an XRPD pattern, obtained with CuKα1-radiation, substantially as shown in FIG. 11.

In a third embodiment, the invention relates to crystal modification 2C, as obtained from a mixture of DMSO and water, having an X-ray powder diffraction (XRPD) pattern, obtained with CuKα1-radiation, with at least specific peaks at °2θ positions 5.0±0.2, 6.2±0.2, 9.4±0.2 and/or 23.9±0.2.

In a specific embodiment thereof, the invention relates to crystal modification 2C, as obtained from a mixture of DMSO and water, having an XRPD pattern, obtained with CuKα1-radiation, with specific peaks at °2θ positions 5.0±0.2, 6.2±0.2, 9.4±0.2 and 23.9±0.2 and one or more of the characteristic peaks: 11.5±0.2, 19.5±0.2 and 20.2±0.2.

In a more specific embodiment thereof, the invention relates to crystal modification 2C, as obtained from a mixture of DMSO and water, having an XRPD pattern, obtained with CuKα1-radiation, with specific peaks at °2θ positions 5.0±0.2, 6.2±0.2, 9.4±0.2, 11.5±0.2, 19.5±0.2, 20.2±0.2 and 23.9±0.2.

In a yet more specific embodiment thereof, the invention relates to crystal modification 2C, as obtained from a mixture of DMSO and water, having an XRPD pattern, obtained with CuKα1-radiation, with characteristic peaks at °2θ positions 5.0±0.2, 6.2±0.2, 9.4±0.2, 11.5±0.2, 19.5±0.2, 20.2±0.2 and 23.9±0.2, and one or more of 4.9±0.2, 5.8±0.2, 6.6±0.2, 8.6±0.2, 9.7±0.2, 10.0±0.2, 10.8±0.2, 13.5±0.2, 15.1±0.2, 17.7±0.2, 17.9±0.2, 19.0±0.2, 19.3±0.2, 20.7±0.2, 21.1±0.2, 21.2±0.2, 21.2±0.2, 22.8±0.2, 25.3±0.2, 26.6±0.2, 27.3±0.2, 27.4±0.2, 28.6±0.2, 30.1±0.2 and 30.2±0.2.

In a yet even more specific embodiment thereof, the invention relates to crystal modification 2C, as obtained from a mixture of DMSO and water, having an XRPD pattern, obtained with CuKα1-radiation, with characteristic peaks at °2θ positions 4.9±0.2, 5.0±0.2, 5.8±0.2, 6.2±0.2, 6.6±0.2, 8.6±0.2, 9.4±0.2, 9.7±0.2, 10.0_0.2, 10.8±0.2, 11.5±0.2, 13.5±0.2, 15.1±0.2, 17.7±0.2, 17.9±0.2, 19.0±0.2, 19.3±0.2, 19.5±0.2, 20.2±0.2, 20.7±0.2, 21.1±0.2, 21.2±0.2, 21.3±0.2, 22.8±0.2, 23.9±0.2, 25.3±0.2, 26.6±0.2, 27.3±0.2, 27.4±0.2, 28.6±0.2, 30.1±0.2 and 30.2±0.2.

Figure 12:
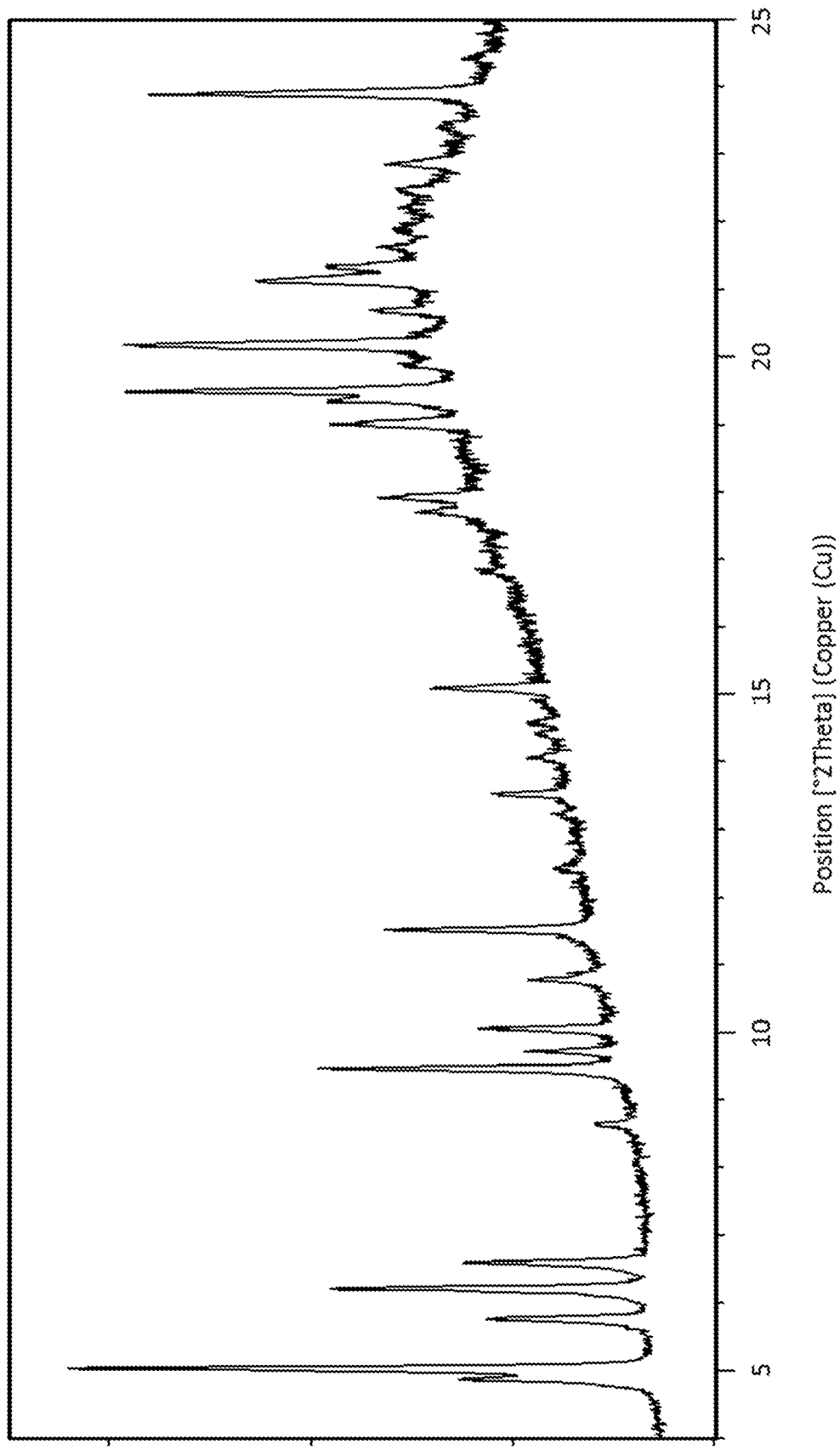
FIG. 12 shows the X-ray powder diffractogram of crystal modification 2C, as obtained from a mixture of DMSO and water (50:50% v/v).

In one particular embodiment, the invention relates to crystal modification 2C, as obtained from a mixture of DMSO and water, having an XRPD pattern, obtained with CuKα1-radiation, substantially as shown in FIG. 12.

Figure 5:
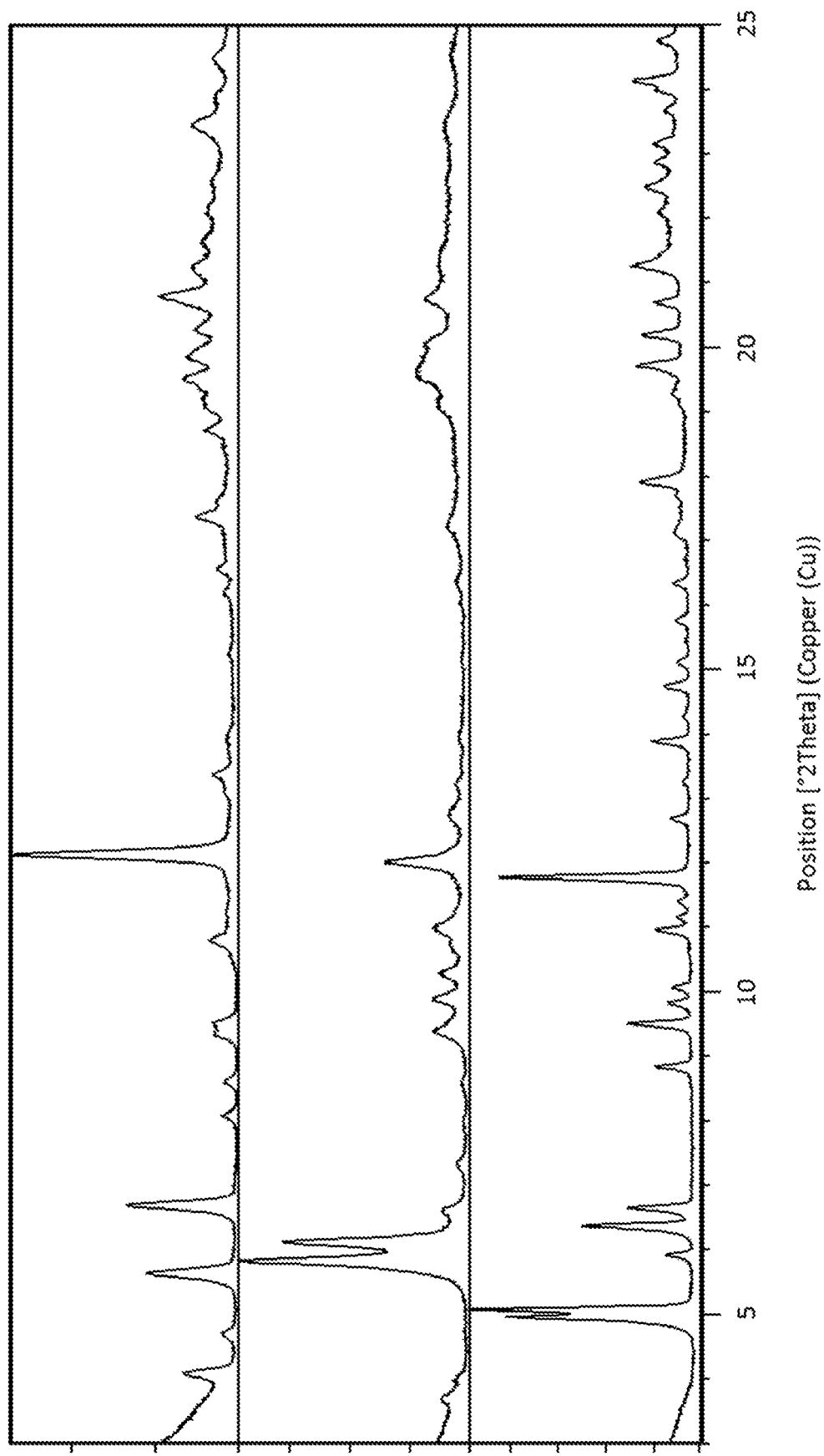
FIG. 5 shows the transformation from crystal modification 2 (bottom), as obtained from a mixture of ethanol (60-80% v/v) and water (20-40% v/v), to crystal modification 1 (top) via crystal modification 12 (middle).

As will be understood from the above, the isolation and characterization of stable crystal modification 1 was not straightforward. Even though it is a hydrate, crystal modification 1 cannot be obtained directly by crystallization from water. In some embodiments, crystal modification 1 is obtained indirectly, e.g. by isolating and drying crystal modification 2, which is formed by crystallization of odevixibat from mixtures of water and certain organic solvents. In some embodiments, crystal modification 1 is obtained from crystal modification 2 after evaporation of the solvent molecules. In some embodiments, the transformation of crystal modification 2 to crystal modification 1 proceeds via a crystalline intermediate, namely modification 12 (see FIG. 5). In some embodiments, the solvent molecules are removed from modification 2 without dissolution and recrystallization of the crystals.

In another aspect, the invention relates to the use of crystal modification 2 (2A, 2B or 2C) of odevixibat as described herein in a process for the preparation of crystal modification 1 of odevixibat.

In yet another aspect, the invention relates to a process for the preparation of crystal modification 1 of odevixibat. In some embodiments, this process involves isolating crystal modification 2 of odevixibat from a solution of odevixibat in a solvent mixture comprising water and an organic solvent selected from the group consisting of methanol, ethanol, 2-propanol, acetone, acetonitrile, 1,4-dioxane, DMF and DMSO, and mixtures thereof. In some embodiments, the process involves isolating crystal modification 2 of odevixibat from a solution of odevixibat in a solvent mixture comprising water and an organic solvent selected from the group consisting of methanol, ethanol, 2-propanol, acetone, acetonitrile, 1,4-dioxane, DMF and DMSO.

In some embodiments, the crystallinity of crystal modification 1 is dependent on the drying process. As is shown in the experimental section, it has been observed that superior crystallinity of crystal modification 1 can be obtained when crystal modification 2 is dried under vacuum (e.g., less than 5 mbar) or under a nitrogen flow. It is believed that drying of crystal modification 2 under these conditions results in a dehydrated form, which then quickly takes up water from the air.

In some embodiments, therefore, the process for the preparation of crystal modification 1 of odevixibat comprises the steps of:
a) isolating crystal modification 2 of odevixibat from a solution of odevixibat in a solvent mixture comprising water and an organic solvent selected from the group consisting of methanol, ethanol, 2-propanol, acetone, acetonitrile, 1,4-dioxane, DMF and DMSO; and
b) drying the solid under vacuum or under a nitrogen flow.

In a preferred embodiment, crystal modification 2 of odevixibat is crystal modification 2A of odevixibat. In a more preferred embodiment, crystal modification 2A of odevixibat is obtained from a mixture of water and ethanol.

In some embodiments, the process for the preparation of crystal modification 1 of odevixibat comprises the steps of:
a) isolating crystal modification 2A of odevixibat from a solution of odevixibat in a mixture of water and ethanol; and
b) drying the solid under vacuum or under a nitrogen flow.

In some embodiments, the crystallinity of crystal modification 1 is dependent on the composition of the mixture of water and the organic solvent. For example, superior crystallinity of crystal modification 1 can be obtained from samples of crystal modification 2A that are obtained from a slurry of odevixibat in a 60:40 (% v/v) mixture of ethanol and water at 22° C. In a preferred embodiment, the ethanol content in the solvent mixture is about 55 to about 75% (v/v), such as about 60 to about 70% (v/v). In some embodiments, the ethanol content in the solvent mixture is about 60% (v/v). In some embodiments, the ethanol content in the solvent mixture is about 65% (v/v). In some embodiments, the ethanol content in the solvent mixture is about 70% (v/v).

In some embodiments, the crystallinity of crystal modification 2A is increased when the isolated crystals are exposed to an ethanol/water atmosphere containing 40 to 60% (v/v) ethanol for a period of at least 24 hours.

In some embodiments, the process comprises the steps of:
a) preparing a saturated solution of odevixibat in a mixture of water and an organic solvent selected from the group consisting of methanol, ethanol, 2-propanol, acetone, acetonitrile, 1,4-dioxane, DMF and DMSO;
b) adding an excess of odevixibat to the saturated solution of step a) so as to obtain a slurry;
c) maintaining stirring of the slurry at a temperature of about 0 to about 25° C., for a period of at least 24 hours;
d) recovering the solid obtained in step c);
e) drying the solid under vacuum or under a nitrogen flow.

In some embodiments, the process comprises the steps of:
a) preparing a saturated solution of odevixibat in a mixture of water and ethanol;
b) adding an excess of odevixibat to the saturated solution of step a) so as to obtain a slurry;
c) maintaining stirring of the slurry at a temperature of about 20 to about 25° C., preferably about 22° C., for a period of at least 24 hours;
d) recovering the solid obtained in step c);
e) optionally exposing the crystals of step d) to an ethanol/water atmosphere; and
f) drying the solid under vacuum or under a nitrogen flow.

Alternatively, crystal modification 1 can be obtained by adding seed crystals to a saturated solution of odevixibat in a mixture of water and a suitable organic solvent. Thus, in another embodiment, the process comprises the steps of:
a) preparing a saturated solution of odevixibat in a mixture of water and an organic solvent selected from the group consisting of methanol, ethanol, 2-propanol, acetone, acetonitrile, 1,4-dioxane, DMF and DMSO;
b) adding seed crystals to the saturated solution of step a);
c) maintaining stirring of the slurry at a temperature of about 0 to about 25° C., for a period of at least 24 hours;
d) recovering the solid obtained in step c);
e) drying the solid under vacuum or under a nitrogen flow.

In some embodiments, the process comprises the steps of:
a) preparing a saturated solution of odevixibat in a mixture of water and ethanol;
b) adding seed crystals to the saturated solution of step a);
c) maintaining stirring of the slurry at a temperature of about 20 to about 25° C., preferably 22° C., for a period of at least 24 hours;
d) recovering the solid obtained in step c);
e) optionally exposing the crystals of step d) to an ethanol/water atmosphere; and
f) drying the solid under vacuum or under a nitrogen flow.

A slurry sample of crystal modification 2 may be used as the seed crystals. Alternatively, crystal modification 1 may be used. It is believed that this form quickly transforms into crystal modification 2 when added to the solvent mixture of the crystallization process.

In a further aspect, the invention relates to crystalline modification 1 of odevixibat, prepared by a process comprising the steps of:

a) isolating crystal modification 2 of odevixibat from a solution of odevixibat in a solvent mixture comprising water and an organic solvent selected from the group consisting of methanol, ethanol, 2-propanol, acetone, acetonitrile, 1,4-dioxane, DMF and DMSO; and b) drying the solid under vacuum or under a nitrogen flow.

In a further aspect, the invention also relates to crystal modification 1 of odevixibat as described herein for use in therapy.

Odevixibat is an ileal bile acid transporter (IBAT) inhibitor. The ileal bile acid transporter (IBAT) is the main mechanism for re-absorption of bile acids from the GI tract. Partial or full blockade of that odevixibat mechanism will result in lower concentration of bile acids in the small bowel wall, portal vein, liver parenchyma, intrahepatic biliary tree, and extrahepatic biliary tree, including the gall bladder. Diseases which may benefit from partial or full blockade of the IBAT mechanism may be those having, as a primary pathophysiological defect, symptoms of excessive concentration of bile acids in serum and in the above organs. Crystal modification 1 of odevixibat, as described herein, is therefore useful in the treatment or prevention of conditions, disorders and diseases wherein inhibition of the bile acid circulation is desirable, such as cardiovascular diseases, fatty acid metabolism and glucose utilization disorders, gastrointestinal diseases and disorders, liver diseases and disorders.

Cardiovascular diseases and disorders of fatty acid metabolism and glucose utilization include, but are not limited to, hypercholesterolemia; disorders of fatty acid metabolism; type 1 and type 2 diabetes mellitus; complications of diabetes, including cataracts, micro- and macrovascular diseases, retinopathy, neuropathy, nephropathy and delayed wound healing, tissue ischaemia, diabetic foot, arteriosclerosis, myocardial infarction, acute coronary syndrome, unstable angina pectoris, stable angina pectoris, stroke, peripheral arterial occlusive disease, cardiomyopathy, heart failure, heart rhythm disorders and vascular restenosis; diabetes-related diseases such as insulin resistance (impaired glucose homeostasis), hyperglycemia, hyperinsulinemia, elevated blood levels of fatty acids or glycerol, obesity, dyslipidemia, hyperlipidemia including hypertriglyceridemia, metabolic syndrome (syndrome X), atherosclerosis and hypertension; and for increasing high density lipoprotein levels.

Gastrointestinal diseases and disorders include constipation (including chronic constipation, functional constipation, chronic idiopathic constipation (CIC), intermittent/sporadic constipation, constipation secondary to diabetes mellitus, constipation secondary to stroke, constipation secondary to chronic kidney disease, constipation secondary to multiple sclerosis, constipation secondary to Parkinson's disease, constipation secondary to systemic sclerosis, drug induced constipation, irritable bowel syndrome with constipation (IBS-C), irritable bowel syndrome mixed (IBS-M), pediatric functional constipation and opioid induced constipation); Crohn's disease; primary bile acid malabsorption; irritable bowel syndrome (IBS); inflammatory bowel disease (IBD); ileal inflammation; and reflux disease and complications thereof, such as Barrett's esophagus, bile reflux esophagitis and bile reflux gastritis. The treatment and prevention of constipation has also been disclosed in WO 2004/089350, which is incorporated by reference in its entirety herein.

A liver disease as defined herein is any disease in the liver and in organs connected therewith, such as the pancreas, portal vein, the liver parenchyma, the intrahepatic biliary tree, the extrahepatic biliary tree, and the gall bladder. In some embodiments, a liver disease a bile acid-dependent liver disease. In some embodiments, a liver disease involves elevated levels of bile acids in the serum and/or in the liver. In some embodiments, a liver disease is a cholestatic liver disease. Liver diseases and disorders include, but are not limited to an inherited metabolic disorder of the liver; inborn errors of bile acid synthesis; congenital bile duct anomalies; biliary atresia; post-Kasai biliary atresia; post-liver transplantation biliary atresia; neonatal hepatitis; neonatal cholestasis; hereditary forms of cholestasis; cerebrotendinous xanthomatosis; a secondary defect of BA synthesis; Zellweger's syndrome; cystic fibrosis-associated liver disease; alpha1-antitrypsin deficiency; Alagilles syndrome (ALGS); Byler syndrome; a primary defect of bile acid (BA) synthesis; progressive familial intrahepatic cholestasis (PFIC) including PFIC-1, PFIC-2, PFIC-3 and non-specified PFIC, post-biliary diversion PFIC and post-liver transplant PFIC; benign recurrent intrahepatic cholestasis (BRIC) including BRIC1, BRIC2 and non-specified BRIC, post-biliary diversion BRIC and post-liver transplant BRIC; autoimmune hepatitis; primary biliary cirrhosis (PBC); liver fibrosis; non-alcoholic fatty liver disease (NAFLD); non-alcoholic steatohepatitis (NASH); portal hypertension; cholestasis; Down syndrome cholestasis; drug-induced cholestasis; intrahepatic cholestasis of pregnancy (jaundice during pregnancy); intrahepatic cholestasis; extrahepatic cholestasis; parenteral nutrition associated cholestasis (PNAC); low phospholipid-associated cholestasis; lymphedema cholestasis syndrome 1 (LSC1); primary sclerosing cholangitis (PSC); immunoglobulin G4 associated cholangitis; primary biliary cholangitis; cholelithiasis (gall stones); biliary lithiasis; choledocholithiasis; gallstone pancreatitis; Caroli disease; malignancy of bile ducts; malignancy causing obstruction of the biliary tree; biliary strictures; AIDS cholangiopathy; ischemic cholangiopathy; pruritus due to cholestasis or jaundice; pancreatitis; chronic autoimmune liver disease leading to progressive cholestasis; hepatic steatosis; alcoholic hepatitis; acute fatty liver; fatty liver of pregnancy; drug-induced hepatitis; iron overload disorders; congenital bile acid synthesis defect type 1 (BAS type 1); drug-induced liver injury (DILI); hepatic fibrosis; congenital hepatic fibrosis; hepatic cirrhosis; Langerhans cell histiocytosis (LCH); neonatal ichthyosis sclerosing cholangitis (NISCH); erythropoietic protoporphyria (EPP); idiopathic adulthood ductopenia (IAD); idiopathic neonatal hepatitis (INH); non syndromic paucity of interlobular bile ducts (NS PILBD); North American Indian childhood cirrhosis (NAIC); hepatic sarcoidosis; amyloidosis; necrotizing enterocolitis; serum bile acid-caused toxicities, including cardiac rhythm disturbances (e.g., atrial fibrillation) in setting of abnormal serum bile acid profile, cardiomyopathy associated with liver cirrhosis ("cholecardia"), and skeletal muscle wasting associated with cholestatic liver disease; viral hepatitis (including hepatitis A, hepatitis B, hepatitis C, hepatitis D and hepatitis E); hepatocellular carcinoma (hepatoma); cholangiocarcinoma; bile acid-related gastrointestinal cancers; and cholestasis caused by tumours and neoplasms of the liver, of the biliary tract and of the pancreas. The treatment and prevention of liver diseases has also been disclosed in WO 2012/064266, which is incorporated by reference in its entirety herein.

Other diseases that may be treated or prevented by crystal modification 1 of odevixibat include hyperabsorption syndromes (including abetalipoproteinemia, familial hypobetalipoproteinemia (FHBL), chylomicron retention disease (CRD) and sitosterolemia); hypervitaminosis and osteopetrosis; hypertension; glomerular hyperfiltration; and pruritus of renal failure.

Biliary atresia is a rare pediatric liver disease that involves a partial or total blockage (or even absence) of large bile ducts. This blockage or absence causes cholestasis that leads to the accumulation of bile acids that damages the liver. In some embodiments, the accumulation of bile acids occurs in the extrahepatic biliary tree. In some embodiments, the accumulation of bile acids occurs in the intrahepatic biliary tree. The current standard of care is the Kasai procedure, which is a surgery that removes the blocked bile ducts and directly connects a portion of the small intestine to the liver. There are currently no approved drug therapies for this disorder.

Provided herein are methods for treating biliary atresia in a subject in need thereof, the methods comprising administration of a therapeutically effective amount of crystal modification I of odevixibat. In some embodiments, the subject has undergone the Kasai procedure prior to administration of a crystal modification I of odevixibat. In some embodiments, the subject is administered crystal modification I of odevixibat prior to undergoing the Kasai procedure. In some embodiments, the treatment of biliary atresia decreases the level of serum bile acids in the subject.

In some embodiments, the level of serum bile acids is determined by, for example, an ELISA enzymatic assay or the assays for the measurement of total bile acids as described in Danese et al., PLoS One. 2017, vol. 12(6): e0179200, which is incorporated by reference herein in its entirety. In some embodiments, the level of serum bile acids can decrease by, for example, 10% to 40%, 20% to 50%, 30% to 60%, 40% to 70%, 50% to 80%, or by more than 90% of the level of serum bile acids prior to administration of crystal modification I of odevixibat. In some embodiments, the treatment of biliary atresia includes treatment of pruritus.

PFIC is a rare genetic disorder that is estimated to affect between one in every 50,000 to 100,000 children born worldwide and causes progressive, life-threatening liver disease.

One manifestation of PFIC is pruritus, which often results in a severely diminished quality of life. In some cases, PFIC leads to cirrhosis and liver failure. Current therapies include Partial External Biliary Diversion (PEBD) and liver transplantation, however, these options can carry substantial risk of post-surgical complications, as well as psychological and social issues.

Three alternative gene defects have been identified that correlate to three separate PFIC subtypes known as types 1, 2 and 3.

PFIC, type 1, which is sometimes referred to as "Byler disease," is caused by impaired bile secretion due to mutations in the ATP8B1 gene, which codes for a protein that helps to maintain an appropriate balance of fats known as phospholipids in cell membranes in the bile ducts. An imbalance in these phospholipids is associated with cholestasis and elevated bile acids in the liver. Subjects affected by PFIC, type 1 usually develop cholestasis in the first months of life and, in the absence of surgical treatment, progress to cirrhosis and end-stage liver disease before the end of the first decade of life.

PFIC, type 2, which is sometimes referred to as "Byler syndrome," is caused by impaired bile salt secretion due to mutations in the ABCB11 gene, which codes for a protein, known as the bile salt export pump, that moves bile acids out of the liver. Subjects with PFIC, type 2 often develop liver failure within the first few years of life and are at increased risk of developing a type of liver cancer known as hepatocellular carcinoma.

PFIC, type 3, which typically presents in the first years of childhood with progressive cholestasis, is caused by mutations in the ABCB4 gene, which codes for a transporter that moves phospholipids across cell membranes.

In addition, TJP2 gene, NR1H4 gene or Myo5b gene mutations have been proposed to be causes of PFIC. In addition, some subjects with PFIC do not have a mutation in any of the ATP8B1, ABCB11, ABCB4, TJP2, NR1H4 or Myo5b genes. In these cases, the cause of the condition is unknown.

Exemplary mutations of the ATP8B1 gene or the resulting protein are listed in Tables 1 and 2, with numbering based on the human wild type ATP8B1 protein (e.g., SEQ ID NO: 1) or gene (e.g., SEQ ID NO: 2). Exemplary mutations of the ABCB11 gene or the resulting protein are listed in Tables 3 and 4, with numbering based on the human wild type ABCB11 protein (e.g., SEQ ID NO: 3) or gene (e.g., SEQ ID NO: 4).

As can be appreciated by those skilled in the art, an amino acid position in a reference protein sequence that corresponds to a specific amino acid position in SEQ ID NO: 1 or 3 can be determined by aligning the reference protein sequence with SEQ ID NO: 1 or 3 (e.g., using a software program, such as ClustalW2). Changes to these residues (referred to herein as "mutations") may include single or multiple amino acid substitutions, insertions within or flanking the sequences, and deletions within or flanking the sequences. As can be appreciated by those skilled in the art, an nucleotide position in a reference gene sequence that corresponds to a specific nucleotide position in SEQ ID NO: 2 or 4 can be determined by aligning the reference gene sequence with SEQ ID NO: 2 or 4 (e.g., using a software program, such as ClustalW2). Changes to these residues (referred to herein as "mutations") may include single or multiple nucleotide substitutions, insertions within or flanking the sequences, and deletions within or flanking the sequences. See also Kooistra, et al., "KLIFS: A structural kinase-ligand interaction database," Nucleic Acids Res. 2016, vol. 44, no. D1, pp. D365-D371, which is incorporated by reference in its entirety herein.

TABLE 1

Exemplary ATP8B1 Mutations

Amino acid position 3 (e.g., T3K)[27]
Amino acid position 23 (e.g., P23L)[5]
Amino acid position 45 (e.g., N45T)[5,8,9]
Amino acid position 46 (e.g., R46X)[4,25]
Amino acid position 62 (e.g., C62R)[28]
Amino acid position 63 (e.g., T63T)[41]
Amino acid position 70 (e.g., D70N)[1,6]
Amino acid position 71 (e.g., R71H)[43]
Amino acid position 78 (e.g., H78Q)[19]
Amino acid position 82 (e.g., T82T)[41]
Amino acid position 92 (e.g., Y92Y)[41]
Amino acid position 93 (e.g., A93A)[6]
Amino acid position 96 (e.g., A96G)[27]
Amino acid position 114 (e.g., E114Q)[8]
Amino acid position 127 (e.g., L127P[6], L127V[36])
Amino acid position 177 (e.g., T177T)[6]
Amino acid position 179 (e.g., E179X)[29]
Δ Amino acid positions 185-282[44]
Amino acid position 197 (e.g., G197Lfs*10)[22]

TABLE 1-continued

Exemplary ATP8B1 Mutations

Amino acid position 201 (e.g., R201S[27], R201H[35])
Amino acid position 203 (e.g., K203E[5,8], K203R[9], K203fs[25])
Amino acid position 205 (e.g., N205fs[6], N205Kfs*2[35])
Amino acid position 209 (e.g., P209T)[4]
Amino acid position 217 (e.g., S217N)[43]
Amino acid position 232 (e.g., D232D)[30]
Amino acid position 233 (e.g., G233R)[38]
Amino acid position 243 (e.g., L243fs*28)[33]
Amino acid position 265 (e.g., C265R)[25]
Amino acid position 271 (e.g., R271X[13], R271R[30])
Amino acid position 288 (e.g., L288S)[6]
Amino acid position 294 (e.g., L294S)[43]
Amino acid position 296 (e.g., R296C)[11]
Amino acid position 305 (e.g., F305I)[28]
Amino acid position 306 (e.g., C306R)[23]
Amino acid position 307 (e.g., H307L)[35]
Amino acid position 308 (e.g., G308V[1], G308D[6], G308S[35])
Amino acid position 314 (e.g., G314S)[13]
Amino acid position 320 (e.g., M320Vfs*13)[11]
Amino acid position 337 (e.g., M337R)[18]
Amino acid position 338 (e.g., N338K)[18]
Amino acid position 340 (e.g., M340V)[18]
Amino acid position 344 (e.g., I344F)[6,20]
Amino acid position 349 (e.g., I349T)[41]
Amino acid position 358 (e.g., G358R)[28]
Amino acid position 367 (e.g., G367G)[41]
Amino acid position 368 (e.g., N368D)[41]
Amino acid position 393 (e.g., I393V)[27]
Amino acid position 403 (e.g., S403Y)[6]
Amino acid position 407 (e.g., S407N)[40]
Amino acid position 412 (e.g., R412P)[6]
Amino acid position 415 (e.g., Q415R)[27]
Amino acid position 422 (e.g., D422H)[35]
Amino acid position 429 (e.g., E429A)[6]
Amino acid position 446 (e.g., G446R)[4,11]
Amino acid position 453 (e.g., S453Y)[6]
Amino acid position 454 (e.g., D454G)[6]
Amino acid position 455 (e.g., K455N)[43]
Amino acid position 456 (e.g., T456M[3,6], T456K[35])
Amino acid position 457 (e.g., G457G[6], G457fs*6[33])
Amino acid position 469 (e.g., C469G)[41]
Amino acid position 478 (e.g., H478H)[41]
Amino acid position 500 (e.g., Y500H)[6]
Amino acid position 525 (e.g., R525X)[4]
Δ Amino acid position 529[6]
Amino acid position 535 (e.g., H535L[6], H535N[41])
Amino acid position 553 (e.g., P553P)[43]
Amino acid position 554 (e.g., D554N[1,6], D554A[35])
Δ Amino acid positions 556-628[44]
Δ Amino acid positions 559-563[35]
Amino acid position 570 (e.g., L570L)[41]
Amino acid position 577 (e.g., I577V)[19]
Amino acid position 581 (e.g., E581K)[35]
Amino acid positions 554 and 581 (e.g., D554A + E581K)[35]
Amino acid position 585 (e.g., E585X)[21]
Amino acid position 600 (e.g., R600W[2,4], R600Q[6])
Amino acid position 602 (e.g., R602X)[3,6]
Amino acid position 628 (e.g., R628W)[6]
Amino acid position 631 (e.g., R631Q)[28]
Δ Amino acid positions 645-699[4]
Amino acid position 661 (e.g., I661T)[1,4,6]
Amino acid position 665 (e.g., E665X)[4,6]
Amino acid position 672 (e.g., K672fs[6], K672Vfs*1[35])
Amino acid position 674 (e.g., M674T)[19]
Amino acid positions 78 and 674 (e.g., H78Q/M674T)[19]
Amino acid position 684 (e.g., D684D)[41]
Amino acid position 688 (e.g., D688G)[6]
Amino acid position 694 (e.g., I694T[6], I694N[17])
Amino acid position 695 (e.g., E695K)[27]
Amino acid position 709 (e.g., K709fs[6], K709Qfs*41[13])
Amino acid position 717 (e.g., T717N)[4]
Amino acid position 733 (e.g., G733R)[6]
Amino acid position 757 (e.g., Y757X)[4]
Amino acid position 749 (e.g., L749P)[21]
Amino acid position 792 (e.g., P792fs)[6]
Δ Amino acid position 795-797[6]
Amino acid position 809 (e.g., I809L)[27]
Amino acid position 814 (e.g., K814N)[28]
Amino acid position 833 (e.g., R833Q[27], R833W[41])
Amino acid position 835 (e.g., K835Rfs*36)[35]
Amino acid position 845 (e.g., K845fs)[25]
Amino acid position 849 (e.g., R849Q)[24]
Amino acid position 853 (e.g., F853S, F853fs)[6]
Amino acid position 867 (e.g., R867C[1], R867fs[6], R867H[23])
Amino acid position 885 (e.g., K885T)[41]
Amino acid position 888 (e.g., T888T)[41]
Amino acid position 892 (e.g., G892R)[6]
Amino acid position 912 (e.g., G912R)[35]
Amino acid position 921 (e.g., S921S)[41]
Amino acid position 924 (e.g., Y924C)[28]
Amino acid position 930 (e.g., R930X[6], R930Q[28])
Amino acid position 941 (e.g., R941X)[35]
Amino acid position 946 (e.g., R946T)[41]
Amino acid position 952 (e.g., R952Q[5,9,15], R952X[6])
Amino acid position 958 (e.g., N958fs)[6]
Amino acid position 960 (e.g., A960A)[41]
Δ Amino acid position 971[43]
Amino acid position 976 (e.g., A976E[41], A976A[43])
Amino acid position 981 (e.g., E981K)[20]
Amino acid position 994 (e.g., S994R)[4]
Amino acid position 1011 (e.g., L1011fs*18)[33]
Amino acid position 1012 (e.g., S1012I)[10]
Amino acid position 1014 (e.g., R1014X)[6,11]
Amino acid position 1015 (e.g., F1015L)[27]
Amino acid position 1023 (e.g., Q1023fs)[6]
Amino acid position 1040 (e.g., G1040R)[1,6]
Amino acid position 1044 (e.g., S0144L)[34]
Amino acid position 1047 (e.g., L1047fs)[6]
Amino acid position 1050 (e.g., I1050K)[31]
Amino acid position 1052 (e.g., L1052R)[28]
Amino acid position 1095 (e.g., W1095X)[11]
Amino acid position 1098 (e.g., V1098X)[35]
Amino acid position 1131 (e.g., Q1131X)[44]
Amino acid position 1142 (e.g., A1142Tfs*35)[43]
Amino acid position 1144 (e.g., Y1144Y)[43]
Amino acid position 1150 (e.g., I1150T)[41]
Amino acid position 1152 (e.g., A1152T)[30]
Amino acid position 1159 (e.g., P1159P)[25,43]
Amino acid position 1164 (e.g., R1164X)[6]
Amino acid position 1193 (e.g., R1193fs*39)[33]
Amino acid position 1197 (e.g., V1197L)[41]
Amino acid position 1208 (e.g., A1208fs)[6]
Amino acid position 1209 (e.g., Y1209Lfs*28)[4]
Amino acid position 1211 (e.g., F1211L)[27]
Amino acid position 1219 (e.g., D1219H[5], D1219G[27])
Amino acid position 1223 (e.g., S1223S)[41]
Amino acid position 1233 (e.g., P1233P)[41]
Amino acid position 1241 (e.g., G1241fs)[6]
Amino acid position 1248 (e.g., T1248T)[43]
Splice site mutation IVS3 + 1__+3delGTG[6]
Splice site mutation IVS3 − 2A > G[6]
IVS6 + 5T > G[17,25]
Splice site mutation IVS8 + 1G > T[6]
IVS9 − G > A[26]
IVS12 + 1G > A[25]
Splice site mutation IVS17 − 1G > A[6]
Splice site mutation IVS18 + 2T > C[6]
Splice site mutation IVS20 − 4CT > AA
Splice site mutation IVS21 + 5G > A[6]
Splice site mutation IVS23 − 3C > A[6]
Splice site mutation IVS26 + 2T > A[6]
g.24774-42062del[4]
c.-4C > G[41]
c.145C > T[12]
c.181 − 72G > A[9]
c.182 − 5T > A[41]
c.182 − 72G > A[41]
c.246A > G[9]
c.239G > A[39]
c.279 + 1__279 + 3delGTG[46]
c.280 − 2A > G[46]
c.625__62715delinsACAGTAAT[46]
c.554 + 122C > T[9]
c.555 − 3T > C[27]
c.625 + 5 G > T[4]
Amino acid position 209 (e.g., P209T) and c.625 + 5 G > T[4]

TABLE 1-continued

Exemplary ATP8B1 Mutations c.628 − 30G > A[41]
c.628 − 31C > T[41]
c.698 + 1G > T[46]
c.698 + 20C > T[41]
c.782 − 1G > A[46]
c.782 − 34G > A[41]
Δ795-797[14]
c.782 − 1G > A[4]
c.852A > C[27]
c.941 − 1G > A[46]
c.1014C > T[9]
c.1029 + 35G > A[9]
c.1221-8C.G[41]
1226delA[16]
c.1429 + 1G > A[46]
c.1429 + 2T > G[13]
c.1429 + 49G > A[41]
c.1430 − 42A > G[41]
c.1493T > C[12]
c.1587_1589delCTT[46]
c.1630 + 2T > G[27]
c.1631 − 10T > A[41]
c.1637 − 37T > C[41]
1660 G > A[14]
1798 C > T[14]
1799 G > A[14]
c.1819 − 39_41delAA[9]
c.1819 + 1G > A[31]
c.1820 − 27G > A[41]
c.1918 + 8C > T[27]
c.1933 − 1G > AK46
c.2097 + 2T > C[32]
c.2097 + 60T > G[41]
c.2097 + 89T > C[41]
c.2097 + 97T > G[41]
c.2210 − 114T > C[9]
2210delA[16]
c.2210 − 45_50dupATAAAA[9]
c.2285 + 29C · T[41]
c.2285 + 32A > G[41]
c.2286 − 4_2286-3delinsAA[46]
c.2418 + 5G > A[46]
c.2707 + 3G > C[27]
c.2707 + 9T > G[41]
c.2707 + 43A > G[41]
c.2709 − 59T > C[41]
c.2931 + 9A > G[41]
c.2931 + 59T > A[41]
C.2932 − 3C > A[46]
c.2932 + 59T > A[9]
c.2937A > C[27]
c.3016 − 9C > A[31]
c.3033-3034del[19]
3122delTCCTA/insACATCGATGTTGATGTTAGG[45]
3318 G > A[14]
c.3400 + 2T > A[46]
c.3401 − 175C > T[9]
c.3401 − 167C > T[9]
c.3401 − 108C > T[9]
c.3531 + 8G > T[9,15]
c.3532 − 15C > T[9]
Δ Phe ex 15[4]
Ex1_Ex13del[6]
Ex2_Ex6del[33]
Ex12_Ex14del[27]
Skipped Exon 24[45]
del5′UTR-ex18[11]
c.*11C > T[41]
c.*1101 + 366G > A[7]
g.92918del565[31]
GC preceding exon 16 (e.g., resulting in a 4 bp deletion)[42]
Frameshift from the 5′ end of exon 16[42]
5′ 1.4 kb deletion[46]

TABLE 2

Selected ATP8B1 Mutations Associated with PFIC-1

Amino acid position 23 (e.g., P23L)[5]
Amino acid position 78 (e.g., H78Q)[19]
Amino acid position 93 (e.g., A93A)[6]
Amino acid position 96 (e.g., A96G)[27]
Amino acid position 127 (e.g., L127P)[6]
Amino acid position 197 (e.g., G197Lfs*10)[22]
Amino acid position 205 (e.g., N205fs)[6]
Amino acid position 209 (e.g., P209T)[4]
Amino acid position 233 (e.g., G233R)[38]
Amino acid position 243 (e.g., L243fs*28)[33]
Amino acid position 288 (e.g., L288S)[6]
Amino acid position 296 (e.g., R296C)[11]
Amino acid position 308 (e.g., G308V[1,6])
Amino acid position 320 (e.g., M320Vfs*13)[11]
Amino acid position 403 (e.g., S403Y)[6]
Amino acid position 407 (e.g., S407N)[40]
Amino acid position 412 (e.g., R412P)[6]
Amino acid position 415 (e.g., Q415R)[27]
Amino acid position 429 (e.g., E429A)[6]
Amino acid position 446 (e.g., G446R)[4]
Amino acid position 456 (e.g., T456M)[3,6]
Amino acid position 457 (e.g., G457G[6], G457fs*6[33])
Amino acid position 500 (e.g., Y500H)[6]
Amino acid position 525 (e.g., R525X)[4]
Δ Amino acid position 529[6]
Amino acid position 535 (e.g., H535L)[6]
Amino acid position 554 (e.g., D554N)[1,6]
Amino acid position 577 (e.g., I577V)[19]
Amino acid position 585 (e.g., E585X)[21]
Amino acid position 600 (e.g., R600W)[4]
Amino acid position 602 (e.g., R602X)[3,6]
Amino acid position 661 (e.g., I661T)[4,6]
Amino acid position 665 (e.g., E665X)[4,6]
Δ Amino acid positions 645-699[4]
Amino acid position 672 (e.g., K672fs)[6]
Amino acid position 674 (e.g., M674T)[19]
Amino acid positions 78 and 674 (e.g., H78Q/M674T)[19]
Amino acid position 688 (e.g., D688G)[6]
Amino acid position 694 (e.g., I694N)[17]
Amino acid position 695 (e.g., E695K)[27]
Amino acid position 709 (e.g., K709fs)[6]
Amino acid position 717 (e.g., T717N)[4]
Amino acid position 733 (e.g., G733R)[6]
Amino acid position 749 (e.g., L749P)[21]
Amino acid position 757 (e.g., Y757X)[4]
Amino acid position 792 (e.g., P792fs)[6]
Amino acid position 809 (e.g., I809L)[27]
Amino acid position 853 (e.g., F853S, F853fs)[6]
Amino acid position 867 (e.g., R867fs)[6]
Amino acid position 892 (e.g., G892R)[6]
Amino acid position 930 (e.g., R930X[6], R952Q[15])
Amino acid position 952 (e.g., R952X)[6]
Amino acid position 958 (e.g., N958fs)[6]
Amino acid position 981 (e.g., E981K)[20]
Amino acid position 994 (e.g., S994R)[4]
Amino acid position 1014 (e.g., R1014X)[6,11]
Amino acid position 1015 (e.g., F1015L)[27]
Amino acid position 1023 (e.g., Q1023fs)[6]
Amino acid position 1040 (e.g., G1040R)[1,6]
Amino acid position 1047 (e.g., L1047fs)[6]
Amino acid position 1095 (e.g., W1095X)[11]
Amino acid position 1208 (e.g., A1208fs)[6]
Amino acid position 1209 (e.g., Y1209Lfs*28)[4]
Amino acid position 1211 (e.g., F1211L)[27]
Amino acid position 1219 (e.g., D1219H[5], D1219G[27])
Splice site mutation IVS3 + 1_+3delGTG[6]
Splice site mutation IVS3 − 2A > G[6]
IVS6 + 5T > G[17]
Splice site mutation IVS8 + 1G > T[6]
IVS9 − G > A[26]
Splice site mutation IVS17 − 1G > A[6]
Splice site mutation IVS18 + 2T > C[6]
Splice site mutation IVS21 + 5G > A[6]
g.24774-42062del[4]
c.145C > T[12]
c.239G > A[39]
c.625 + 5 G > T[4]
Amino acid position 209 (e.g., P209T) and c.625 + 5 G > T[4]

TABLE 2-continued

Selected ATP8B1 Mutations Associated with PFIC-1 c.782 − 1G > A[4]
c.1493T > C[12]
c.1630 + 2T > G[27]
1660 G > A[14]
c.2707 + 3G > C[27]
c.2097 + 2T > C[32]
c.3033-3034del[19]
3318 G > A[14]
c.3158 + 8G > T[15]
Δ Phe ex 15[4]
Ex1__Ex13del[6]
Ex2__Ex6del[33]
Ex12__Ex14del[27]
del5'UTR-ex18[11]
c.*1101 + 366G > A[7]
GC preceding exon 16 (e.g., resulting in a 4 bp deletion)[42]
Frameshift from the 5' end of exon 16[42]

[A] A mutation to 'X' denotes an early stop codon

REFERENCES FOR TABLES 1 AND 2

[1] Folmer et al., Hepatology. 2009, vol. 50(5), p. 1597-1605.
[2] Hsu et al., Hepatol Res. 2009, vol. 39(6), p. 625-631.
[3] Alvarez et al., Hum Mol Genet. 2004, vol. 13(20), p. 2451-2460.
[4] Davit-Spraul et al., Hepatology 2010, vol. 51(5), p. 1645-1655.
[5] Vitale et al., J Gastroenterol. 2018, vol. 53(8), p. 945-958.
[6] Klomp et al., Hepatology 2004, vol. 40(1), p. 27-38.
[7] Zarenezhad et al., Hepatitis Monthly: 2017, vol. 17(2); e43500.
[8] Dixon et al., Scientific Reports 2017, vol. 7, 11823.
[9] Painter et al., Eur J Hum Genet. 2005, vol. 13(4), p. 435-439.
[10] Deng et al., World J Gastroenterol. 2012, vol. 18(44), p. 6504-6509.
[11] Giovannoni et al., PLoS One. 2015, vol. 10(12): e0145021.
[12] Li et al., Hepatology International 2017, vol. 11, No. 1, Supp. Supplement 1, pp. S180. Abstract Number: OP284.
[13] Togawa et al., Journal of Pediatric Gastroenterology and Nutrition 2018, vol. 67, Supp. Supplement 1, pp. S363. Abstract Number: 615.
[14] Miloh et al., Gastroenterology 2006, vol. 130, No. 4, Suppl. 2, pp. A759-A760. Meeting Info.: Digestive Disease Week Meeting/107th Annual Meeting of the American-Gastroenterological-Association. Los Angeles, Calif., USA. May 19.
[15] Dröge et al., Zeitschrift fur Gastroenterologie 2015, vol. 53, No. 12. Abstract Number: A3-27. Meeting Info: 32. Jahrestagung der Deutschen Arbeitsgemeinschaft zum Studium der Leber. Dusseldorf, Germany. 22 Jan. 2016-23 Jan. 2016
[16] Mizuochi et al., Clin Chim Acta. 2012, vol. 413(15-16), p. 1301-1304.
[17] Liu et al., Hepatology International 2009, vol. 3, No. 1, p. 184-185. Abstract Number: PE405. Meeting Info: 19th Conference of the Asian Pacific Association for the Study of the Liver. Hong Kong, China. 13 Feb. 2009-16 Feb. 2009
[18] McKay et al., Version 2. F1000Res. 2013; 2: 32. DOI: 10.12688/f1000research.2-32.v2
[19] Hasegawa et al., Orphanet J Rare Dis. 2014, vol. 9:89.
[20] Stone et al., J Biol Chem. 2012, vol. 287(49), p. 41139-51.
[21] Kang et al., J Pathol Transl Med. 2019 May 16. doi: 10.4132/jptm.2019.05.03. [Epub ahead of print]
[22] Sharma et al., BMC Gastroenterol. 2018, vol. 18(1), p. 107.
[23] Uegaki et al., Intern Med. 2008, vol. 47(7), p. 599-602.
[24] Goldschmidt et al., Hepatol Res. 2016, vol. 46(4), p. 306-311.
[25] Liu et al., J Pediatr Gastroenterol Nutr. 2010, vol. 50(2), p. 179-183.
[26] Jung et al., J Pediatr Gastroenterol Nutr. 2007, vol. 44(4), p. 453-458.
[27] Bounford. University of Birmingham. Dissertation Abstracts International, (2016) Vol. 75, No. 1C. Order No.: AA110588329. ProQuest Dissertations & Theses.
[28] Stolz et al., Aliment Pharmacol Ther. 2019, vol. 49(9), p. 1195-1204.
[29] Ivashkin et al., Hepatology International 2016, vol. 10, No. 1, Supp. SUPPL. 1, pp. S461. Abstract Number: LBO-38. Meeting Info: 25th Annual Conference of the Asian Pacific Association for the Study of the Liver, APASL 2016. Tokyo, Japan. 20 Feb. 2016-24 Feb. 2016
[30] Blackmore et al., J Clin Exp Hepatol. 2013, vol. 3(2), p. 159-161.
[31] Matte et al., J Pediatr Gastroenterol Nutr. 2010, vol. 51(4), p. 488-493.
[32] Squires et al., J Pediatr Gastroenterol Nutr. 2017, vol. 64(3), p. 425-430.
[33] Hayshi et al., EBioMedicine. 2018, vol. 27, p. 187-199.
[34] Nagasaka et al., J Pediatr Gastroenterol Nutr. 2007, vol. 45(1), p. 96-105.
[35] Wang et al., PLoS One. 2016; vol. 11(4): e0153114.
[36] Narchi et al., Saudi J Gastroenterol. 2017, vol. 23(5), p. 303-305.
[37] Alashkar et al., Blood 2015, vol. 126, No. 23. Meeting Info.: 57th Annual Meeting of the American-Society-of-Hematology. Orlando, Fla., USA. Dec. 5-8, 2015. Amer Soc Hematol.
[38] Ferreira et al., Pediatric Transplantation 2013, vol. 17, Supp. SUPPL. 1, pp. 99. Abstract Number: 239. Meeting Info: IPTA 7th Congress on Pediatric Transplantation. Warsaw, Poland. 13 Jul. 2013-16 Jul. 2013.
[39] Pauli-Magnus et al., J Hepatol. 2005, vol. 43(2), p. 342-357.
[40] Jericho et al., Journal of Pediatric Gastroenterology and Nutrition 2015, vol. 60(3), p. 368-374.
[41] van der Woerd et al., PLoS One. 2013, vol. 8(11): e80553.
[42] Copeland et al., J Gastroenterol Hepatol. 2013, vol. 28(3), p. 560-564.
[43] Dröge et al., J Hepatol. 2017, vol. 67(6), p. 1253-1264.
[44] Chen et al., Journal of Pediatrics 2002, vol. 140(1), p. 119-124.
[45] Jirsa et al., Hepatol Res. 2004, vol. 30(1), p. 1-3.
[46] van der Woerd et al., Hepatology 2015, vol. 61(4), p. 1382-1391.

In some embodiments, the mutation in ATP8B1 is selected from L127P, G308V, T456M, D554N, F529del, I661T, E665X, R930X, R952X, R1014X, and G1040R.

TABLE 3

Exemplary ABCB11 Mutations

Amino acid position 1 (e.g., M1V)[9]
Amino acid position 4 (e.g., S4X)[4,64]
Amino acid position 8 (e.g., R8X)[88]
Amino acid position 19 (e.g., G19R)[56]
Amino acid position 24 (e.g., K24X)[35]

TABLE 3-continued

Exemplary ABCB11 Mutations

Amino acid position 25 (e.g., S25X)[5,14]
Amino acid position 26 (e.g., Y26Ifs*7)[38]
Amino acid position 36 (e.g., D36D)[27]
Amino acid position 38 (e.g., K38Rfs*24)[73]
Amino acid position 43 (e.g., V43I)[57]
Amino acid position 49 (e.g., Q49X)[73]
Amino acid position 50 (e.g., L50S, L50W)[57]
Amino acid position 52 (e.g., R52W[26], R52R[28])
Amino acid position 56 (e.g., S56L)[58]
Amino acid position 58 (e.g., D58N)[62]
Amino acid position 62 (e.g., M62K)[9]
Amino acid position 66 (e.g., S66N)[17]
Amino acid position 68 (e.g., C68Y)[41]
Amino acid position 50 (e.g., L50S)[5,7]
Amino acid position 71 (e.g., L71H)[73]
Amino acid position 74 (e.g., I74R)[71]
Amino acid position 77 (e.g., P77A)[73]
Amino acid position 87 (e.g., T87R)[67]
Amino acid position 90 (e.g., F90F)[7,27]
Amino acid position 93 (e.g., Y93S[13], Y93X[88])
Amino acid position 96 (e.g., E96X)[88]
Amino acid position 97 (e.g., L97X)[39]
Amino acid position 101 (e.g., Q101Dfs*8)[9]
Amino acid position 107 (e.g., C107R)[36]
Amino acid position 112 (e.g., I112T)[9]
Amino acid position 114 (e.g., W114R)[2,9]
Amino acid position 123 (e.g., M123T)[67]
Amino acid position 127 (e.g., T127Hfs*6)[5]
Amino acid position 129 (e.g., C129Y)[25]
Amino acid position 130 (e.g., G130G)[77]
Amino acid position 134 (e.g., I134I)[28]
Amino acid position 135 (e.g., E135K[7,13], E135L[17])
Amino acid position 137 (e.g., E137K)[7]
Amino acid position 157 (e.g., Y157C)[5]
Amino acid position 161 (e.g., C161X)[39]
Amino acid position 164 (e.g., V164Gfs*7[30], V164I[85])
Amino acid position 167 (e.g., A167S[4], A167V[7], A167T[9,17])
Amino acid position 181 (e.g., R181I)[35]
Amino acid position 182 (e.g., I182K)[9]
Amino acid position 183 (e.g., M183V[8], M183T[9])
Amino acid position 185 (e.g., M185I)[73]
Amino acid position 186 (e.g., E186G)[2,7,22]
Amino acid position 188 (e.g., G188W)[73]
Amino acid position 194 (e.g., S194P)[7]
Amino acid position 198 (e.g., L198P)[7]
Amino acid position 199 (e.g., N199Ifs*15X)[88]
Amino acid position 206 (e.g., I206V)[28]
Amino acid position 212 (e.g., A212T)[73]
Amino acid position 217 (e.g., M217R)[88]
Amino acid position 225 (e.g., T225P)[57]
Amino acid position 226 (e.g., S226L)[9]
Amino acid position 232 (e.g., L232Cfs*9)[9]
Amino acid position 233 (e.g., L233S)[86]
Amino acid position 238 (e.g., G238V)[2,7]
Amino acid position 242 (e.g., T242I)[5,7]
Amino acid position 245 (e.g., I245Tfs*26)[57]
Amino acid position 256 (e.g., A256G)[9]
Amino acid position 260 (e.g., G260D)[7]
Amino acid position 269 (e.g., Y269Y)[27]
Amino acid position 277 (e.g., A277E)[77]
Amino acid position 283 (e.g., E283D)[73]
Amino acid positions 212 and 283 (e.g., A212T + E283D)[73]
Amino acid position 284 (e.g., V284L[7,39], V284V[7], V284D[23])
Amino acid position 297 (e.g., E297G[1,2,5,7], E297K[7])
Amino acid position 299 (e.g., R299K)[28]
Amino acid position 303 (e.g., R303K[8], R303M[63] R303fsX321[83])
Amino acid position 304 (e.g., Y304X)[26]
Amino acid position 312 (e.g., Q312H)[7]
Amino acid position 313 (e.g., R313S)[5,7]
Amino acid position 314 (e.g., W314X)[57]
Amino acid position 318 (e.g., K318Rfs*26)[29]
Amino acid position 319 (e.g., G319G)[7]
Amino acid position 327 (e.g., G327E)[5,7]
Amino acid position 330 (e.g., W330X)[24]
Amino acid position 336 (e.g., C336S)[2,7]
Amino acid position 337 (e.g., Y337H)[21,27]
Amino acid position 342 (e.g., W342G)[50]
Amino acid position 354 (e.g., R354X)[9]
Amino acid position 361 (e.g., Q361X[57], Q361R[74])
Amino acid position 366 (e.g., V366V[28], V366D[57])
Amino acid position 368 (e.g., V368Rfs*27)[5]
Amino acid position 374 (e.g., G374S)[3]
Amino acid position 380 (e.g., L380Wfs*18)[5]
Amino acid position 382 (e.g., A382G)[88]
Δ Amino acid positions 382-388[5]
Δ Amino acid positions 383-389[57]
Amino acid position 387 (e.g., R387H)[9]
Amino acid position 390 (e.g., A390P)[5,7]
Amino acid position 395 (e.g., E395E)[28]
Amino acid position 404 (e.g., D404G)[9]
Amino acid position 410 (e.g., G410D)[5,7]
Amino acid position 413 (e.g., L413W)[5,7]
Amino acid position 415 (e.g., R415X)[42]
Amino acid position 416 (e.g., I416I)[27]
Amino acid position 420 (e.g., I420T)[9]
Amino acid position 423 (e.g., H423R)[13]
Amino acid position 432 (e.g., R432T)[1,2,7]
Amino acid position 436 (e.g., K436N)[40]
Amino acid position 440 (e.g., D440E)[88]
Amino acid position 444 (e.g., V444A)[2]
Amino acid position 454 (e.g., V454X)[49]
Amino acid position 455 (e.g., G455E)[9]
Amino acid position 457 (e.g., S457Vfs*23)[88]
Amino acid position 461 (e.g., K461E)[2,7]
Amino acid position 462 (e.g., S462R)[88]
Amino acid position 463 (e.g., T463I)[5,7]
Amino acid position 466 (e.g., Q466K)[5,7]
Amino acid position 470 (e.g., R470Q[5,7], R470X[9])
Amino acid position 471 (e.g., Y472X)[5]
Amino acid position 472 (e.g., Y472C[5,27], Y472X[14])
Amino acid position 473 (e.g., D473Q[35], D473V[88])
Amino acid position 475 (e.g., C475X)[29]
Amino acid position 481 (e.g., V481E)[5,7]
Amino acid position 482 (e.g., D482G)[2,5,7]
Amino acid position 484 (e.g., H484Rfs*5)[9]
Amino acid position 487 (e.g., R487H[2], R487P[5])
Amino acid position 490 (e.g., N490D)[5,7]
Amino acid position 493 (e.g., W493X)[8]
Amino acid positon 496 (e.g., D496V)[88]
Amino acid position 498 (e.g., I498T)[2,7]
Amino acid position 499 (e.g., G499E)[73]
Amino acid position 501 (e.g., V501G)[68]
Amino acid position 504 (e.g., E504K)[79]
Amino acid position 510 (e.g., T510T)[7]
Amino acid position 512 (e.g., I512T)[5,7]
Amino acid position 515 (e.g., N515T[5,7], N515D[64])
Amino acid position 516 (e.g., I516M)[17]
Amino acid position 517 (e.g., R517H)[5,7]
Amino acid position 520 (e.g., R520X)[5]
Amino acid position 523 (e.g., A523G)[13]
Amino acid position 528 (e.g., I528Sfs*21[5], I528X[9], I528T[73])
Amino acid position 535 (e.g., A535A[7], A535X[89])
Amino acid position 540 (e.g., F540L)[46]
Amino acid position 541 (e.g., I541L[5,7], I541T[5,17])
Amino acid position 546 (e.g., Q546K[39], Q546H[73])
Amino acid position 548 (e.g., F548Y)[5,7]
Amino acid position 549 (e.g., D549V)[9]
Amino acid position 554 (e.g., E554K)[21]
Amino acid position 556 (e.g., G556R)[67]
Amino acid position 558 (e.g., Q558H)[23]
Amino acid position 559 (e.g., M559T)[57]
Amino acid position 562 (e.g., G562D[5,7], G562S[73])
Amino acid position 570 (e.g., A570T[2,5,7], A570V[26])
Amino acid position 575 (e.g., R575X[2,5], R575Q[21])
Amino acid position 580 (e.g., L580P)[57]
Amino acid position 586 (e.g., T586I)[7]
Amino acid position 587 (e.g., S587X)[73]
Amino acid position 588 (e.g., A588V[5,7], A588P[73])
Amino acid position 591 (e.g., N591S)[2,7]
Amino acid position 593 (e.g., S593R)[2,7]
Amino acid position 597 (e.g., V597V[9], V597L[13])
Amino acid position 603 (e.g., K603K)[55]
Amino acid position 609 (e.g., H609Hfs*46)[26]
Amino acid position 610 (e.g., I610Gfs*45[9], I610T[57])[9]
Amino acid position 615 (e.g., H615R)[26]
Amino acid position 616 (e.g., R616G[28], R616H[73])

TABLE 3-continued

Exemplary ABCB11 Mutations

Amino acid position 619 (e.g., T619A)[28]
Amino acid position 623 (e.g., A623A)[28]
Amino acid position 625 (e.g., T625Nfs*5)[26]
Amino acid position 627 (e.g., I627T)[7]
Amino acid position 628 (e.g., G628Wfs*3)[70]
Amino acid position 636 (e.g., E636G)[2]
Amino acid position 648 (e.g., G648Vfs*6[5], G648V[50])
Amino acid position 655 (e.g., T655I)[7]
Amino acid position 669 (e.g., I669V)[26]
Amino acid position 676 (e.g., D676Y)[11]
Amino acid position 677 (e.g., M677V)[7,13]
Amino acid position 679 (e.g., A679V)[58]
Amino acid position 685 (e.g., G685W)[60]
Amino acid position 696 (e.g., R696W[27], R696Q[58])
Amino acid position 698 (e.g., R698H[7,9], R698K[61], R698C[88])
Amino acid position 699 (e.g., S699P)[9]
Amino acid position 701 (e.g., S701P)[58]
Amino acid position 702 (e.g., Q702X)[89]
Amino acid position 709 (e.g., E709K)[7]
Amino acid position 710 (e.g., P710P)[7]
Amino acid position 712 (e.g., L712L)[28]
Amino acid position 721 (e.g., Y721C)[88]
Amino acid position 729 (e.g., D724N)[39]
Amino acid position 731 (e.g., P731S)[23]
Amino acid position 740 (e.g., P740Qfs*6)[73]
Amino acid position 758 (e.g., G758R)[5]
Amino acid position 766 (e.g., G766R)[5,24]
Amino acid position 772 (e.g., Y772X)[5]
Amino acid position 804 (e.g., A804A)[7]
Amino acid position 806 (e.g., G806D[44], G806G[55])
Amino acid position 809 (e.g., S809F)[81]
Amino acid position 817 (e.g., G817G)[88]
Amino acid position 818 (e.g., Y818F)[7]
Amino acid position 824 (e.g., G824E)[42]
Amino acid position 825 (e.g., G825G)[73]
Amino acid position 830 (e.g., R830Gfs*28)[73]
Amino acid position 832 (e.g., R832C[7,26], R832H[41])
Amino acid position 842 (e.g., D842G)[2]
Amino acid position 848 (e.g., D848N)[73]
Amino acid position 855 (e.g., G855R)[11]
Amino acid position 859 (e.g., T859R)[5,7]
Amino acid position 865 (e.g., A865V)[27]
Amino acid position 866 (e.g., S866A)[57]
Amino acid position 868 (e.g., V868D)[73]
Amino acid position 869 (e.g., Q869P)[73]
Amino acid position 875 (e.g., Q875X)[73]
Amino acid position 877 (e.g., G877R)[56]
Amino acid position 879 (e.g., I879R)[88]
Amino acid position 893 (e.g., A893V)[57]
Amino acid position 901 (e.g., S901R[17], S901I[73])
Amino acid position 903 (e.g., V903G)[57]
Δ Amino acid position 919[12]
Amino acid position 923 (e.g., T923P)[2,7]
Amino acid position 926 (e.g., A926P)[2,7]
Amino acid position 928 (e.g., R928X[15], R928Q[40])
Amino acid position 930 (e.g., K930X[5], K930Efs*79[5,10], K930Efs*49[26])
Amino acid position 931 (e.g., Q931P)[27]
Amino acid position 945 (e.g., S945N)[57]
Amino acid position 948 (e.g., R948C)[5,7,26]
Amino acid position 958 (e.g., R958Q)[28]
Amino acid position 969 (e.g., K969R)[88]
Δ Amino acid positions 969-972[5]
Amino acid position 973 (e.g., T973I)[57]
Amino acid position 976 (e.g., Q976R[58], Q976X[88])
Amino acid position 979 (e.g., N979D)[5,7]
Amino acid position 981 (e.g., Y981Y)[28]
Amino acid position 982 (e.g., G982R)[2,5,7]
Amino acid positions 444 and 982 (e.g., V444A + G982R)[38]
Amino acid position 995 (e.g., A995A)[28]
Amino acid position 1001 (e.g., R1001R)[9]
Amino acid position 1003 (e.g., G1003R)[24]
Amino acid position 1004 (e.g., G1004D)[2,7]
Amino acid position 1027 (e.g., S1027R)[26]
Amino acid position 1028 (e.g., A1028A[7,10,88], A1028E[88])
Amino acid position 1029 (e.g., T1029K)[5]
Amino acid position 1032 (e.g., G1032R)[12]
Amino acid position 1041 (e.g., Y1041X)[9]
Amino acid position 1044 (e.g., A1044P)[88]
Amino acid position 1050 (e.g., R1050C)[2,7,57]
Amino acid position 1053 (e.g., Q1053X)[57]
Amino acid position 1055 (e.g., L1055P)[36]
Amino acid position 1057 (e.g., R1057X[2], R1057Q[58])
Amino acid position 1058 (e.g., Q1058Hfs*38[9], Q1058fs*38[17], Q1058X[73])
Amino acid position 1061 (e.g., I1061Vfs*34)[9]
Amino acid position 1083 (e.g., C1083Y)[47]
Amino acid position 1086 (e.g., T1086T)[28]
Amino acid position 1090 (e.g., R1090X)[2,5]
Amino acid position 1099 (e.g., L1099Lfs*38)[26]
Amino acid position 1100 (e.g., S1100Qfs*38)[13]
Amino acid position 1110 (e.g., A1110E)[5,7]
Amino acid position 1112 (e.g., V1112F)[70]
Amino acid position 1116 (e.g., G1116R[7], G1116F[9,17], G1116E[36])
Amino acid position 1120 (e.g., S1120N)[88]
Amino acid position 1128 (e.g., R1128H[2,7], R1128C[5,7,13])
Amino acid position 1131 (e.g., D1131V)[27]
Amino acid position 1144 (e.g., S1144R)[7]
Amino acid position 1147 (e.g., V1147X)[5]
Amino acid position 1153 (e.g., R1153C[2,5,7], R1153H[5])
Amino acid position 1154 (e.g., S1154P)[5,7]
Amino acid position 1162 (e.g., E1162X)[39]
Δ Amino acid position 1165[88]
Amino acid position 1164 (e.g., V1164Gfs*7)
Amino acid position 1173 (e.g., N1173D)[57]
Amino acid position 1175 (e.g., K1175T)[58]
Amino acid position 1186 (e.g., E1186K)[7]
Amino acid position 1192 (e.g., A1192Efs*50)[9]
Amino acid position 1196 (e.g., Q1196X)[88]
Amino acid position 1197 (e.g., L1197G)[7]
Amino acid position 1198 (e.g., H1198R)[27]
Amino acid position 1204 (e.g., L1204P)[88]
Amino acid position 1208 (e.g. Y1208C)[73]
Amino acid position 1210 (e.g., T1210P[5,7], T1210F[57])
Amino acid position 1211 (e.g., N1211D)[7]
Amino acid position 1212 (e.g., V1212F)[36]
Amino acid position 1215 (e.g., Q1215X)[5]
Amino acid position 1221 (e.g., R1221K)[53]
Amino acid position 1223 (e.g., E1223D)[7]
Amino acid position 1226 (e.g., R1226P)[73]
Amino acid position 1228 (e.g., A1228V)[7]
Amino acid position 1231 (e.g., R1231W[5,7], R1231Q[5,7])
Amino acid position 1232 (e.g., A1232D)[17]
Amino acid position 1235 (e.g., R1235X)[5,12]
Amino acid position 1242 (e.g., L1242I)[5,7]
Amino acid position 1243 (e.g., D1243G)[67]
Amino acid position 1249 (e.g., L1249X)[73]
Amino acid position 1256 (e.g., T1256fs*1296)[83]
Amino acid position 1268 (e.g., R1268Q)[2,7]
Amino acid position 1276 (e.g., R1276H)[30]
Amino acid position 1283 (e.g., A1283A[28], A1283V[88])
Amino acid position 1292 (e.g., G1292V)[73]
Amino acid position 1298 (e.g., G1298R)[5]
Amino acid position 1302 (e.g., E1302X)[5]
Amino acid position 1311 (e.g., Y1311X)[57]
Amino acid position 1316 (e.g., T1316Lfs*64)[15]
Amino acid position 1321 (e.g., S1321N)[57]
Intron 4 ((+3)A > C)[1]
IVS4 − 74A > T[89]
Splice site mutation 3' Intron 5 c.3901G > A[5]
Splice site mutation 5; Intron 7 c.6111G > A[5]
Splice site mutation IVS7 + 1G > A[14]
IVS7 + 5G > A[40]
IVS8 + 1G > C[76]
Splice site mutation 5' Intron 9 c.9081delG[5]
Splice site mutation 5' Intron 9 c.9081G > T[5]
Splice site mutation 5' Intron 9 c.9081G > A[5]
Splice site mutation IVS9 + 1G > T[14]
Splice site mutation 3' Intron 13 c.143513_1435-8del[5]
Splice site mutation IVS13del-13^-8[14]
Splice site mutation 3' Intron 16 c.20128T > G[5]
Splice site mutation IVS16 − 8T > G[14]
Splice site mutation 5' Intron 18 c.21781G > T[5]
Splice site mutation 5' Intron 18 c.21781G > A[5]
Splice site mutation 5' Intron 18 c.21781G > C[5]
Splice site mutation 3' Intron 18 c.21792A > G[5]
Splice site mutation IVS18 + 1G > A[14]

TABLE 3-continued

Exemplary ABCB11 Mutations

Splice site mutation 5' Intron 19 c.2343 + 1G > T[5]
Splice site mutation 5' Intron 19 c.2343 + 2T > C[5]
Splice site mutation IVS19 + 2T > C[14]
Splice site mutation IVS19 + 1G > A[22]
Splice site mutation 3' Intron 21 c.26112A > T[5]
IVS22 + 3A > G[89]
IVS 23 − 8 G − A[36]
IVS24 + 5G > A[51]
Splice site mutation 5' Intron 24 c.32131delG[5]
IVS35 − 6C > G[89]
Putative splice mutation 1198 − 1G > C[17]
Putative splice mutation 1810 − 3C > G[17]
Putative splice mutation 2178 + 1G > A[17]
Putative splice mutation 2344 − 1G > T[17]
Putative splice mutation 2611 − 2A > T[39]
Putative splice mutation 3213 + 1_3213 + 2delinsA[17]
c.-24C > A[44,78]
c.76 13 G > T[9]
c.77 − 19T > A[52]
c.90_93delGAAA[18]
c.124G > A[69]
c.150 + 3 A > C[10]
174C > T[54]
c.245T > C[87]
c.249_250insT[18]
270T > C[54]
402C > T[54]
585G > C[54]
c.611 + 1G > A[70]
c.611 + 4A > G[36]
c.612 − 15_-6del10bp[55]
c.625A > C[31]
c.627 + 5G > T[31]
c.625A > C/c.627 + 5G > T[31]
696G > T[54]
c. 784 + 1G > C[49]
807T > C[54]
c.886G > T[31]
c.890A > G[59]
c.908 + 1G > A[57]
c.908 + 5G > A[55]
c.908delG[59]
c.909 − 15A > G[66]
957A > G[54]
c.1084 − 2A > G[57]
1145 1 bp deletion[90]
1281C > T[54,57]
c.1309 − 165C > T[19]
c.1434 + 174G > A[19]
c.1434 + 70C > T[19]
c.1530C > A[57]
c.1587 − 1589delCTT[31]
c.1621A > C[33,59]
c.1638 + 32T > C[66]
c.1638 + 80C > T[66]
1671C > T[54]
1791G > T[54]
1939delA[14]
c.2075 + 3A > G[53]
c.2081T > A[31]
c.2093G > A[65]
2098delA[16]
c.2138 − 8T > G[67]
2142A > G[54]
c.2178 + 1G > T[36,39]
c.2179 − 17C > A[66]
c.2344 − 157T > G[66]
c.2344 − 17T > C[66]
c.2417G > A[78]
c.2541delG[87]
c.2620C > T[32,33]
c.2815 − 8A > G[55]
c.3003A > G[37]
c.3084A > G[48,54]
c.3213 + 4 A > G[9,37]
c.3213 + 5 G > A[9]
c.3268C > T[75]
3285A > G[54]

TABLE 3-continued

Exemplary ABCB11 Mutations c.3382C > T[75]
3435A > G[54]
c.3491delT[72]
c.3589C > T[57]
c.3765(+1 + 5)del5[42]
c.3766 − 34A > G[66]
c.3767 − 3768insC[6]
c.3770delA[67]
c.3826C > T[72]
c.3846C > T[57]
c.3929delG[67]
c.*236A > G[66]
1145delC[8]
Ex13__Ex17del[82]

TABLE 4

Selected ABCB11 Mutations Associated with PFIC-2

Amino acid position 1 (e.g., M1V)[9]
Amino acid position 4 (e.g., S4X)[64]
Amino acid position 19 (e.g., G19R)[56]
Amino acid position 25 (e.g., S25X)[14]
Amino acid position 26 (e.g., Y26Ifs*7)[38]
Amino acid position 50 (e.g., L50S)[7,57]
Amino acid position 52 (e.g., R52W)[26]
Amino acid position 58 (e.g., D58N)[62]
Amino acid position 62 (e.g., M62K)[9]
Amino acid position 66 (e.g., S66N)[17]
Amino acid position 68 (e.g., C68Y)[41]
Amino acid position 93 (e.g., Y93S)[13]
Amino acid position 101 (e.g., Q101Dfs*8)[9]
Amino acid position 107 (e.g., C107R)[36]
Amino acid position 112 (e.g., I112T)[9]
Amino acid position 114 (e.g., W114R)[2,9]
Amino acid position 129 (e.g., C129Y)[25]
Amino acid position 135 (e.g., E135K[13], E135L[17])
Amino acid position 167 (e.g., A167V[7], A167T[9,17])
Amino acid position 182 (e.g., I182K)[9]
Amino acid position 183 (e.g., M183V[8], M183T[9])
Amino acid position 225 (e.g., T225P)[57]
Amino acid position 226 (e.g., S226L)[9]
Amino acid position 232 (e.g., L232Cfs*9)[9]
Amino acid position 233 (e.g., L233S)[86]
Amino acid position 238 (e.g., G238V)[2,7]
Amino acid position 242 (e.g., T242I)[7]
Amino acid position 245 (e.g., I245Tfs*26)[57]
Amino acid position 256 (e.g., A256G)[9]
Amino acid position 260 (e.g., G260D)[57]
Amino acid position 284 (e.g., V284L)[7]
Amino acid position 297 (e.g., E297G)[2,7]
Amino acid position 303 (e.g., R303K[8], R303M[63], R303fsX321[83])
Amino acid position 304 (e.g., Y304X)[26]
Amino acid position 312 (e.g., Q312H)[7]
Amino acid position 313 (e.g., R313S)[7]
Amino acid position 314 (e.g., W314X)[57]
Amino acid position 318 (e.g., K318Rfs*26)[29]
Amino acid position 327 (e.g., G327E)[7]
Amino acid position 330 (e.g., V330X)[24]
Amino acid position 336 (e.g., C336S)[2,7]
Amino acid position 337 (e.g., Y337H)[21]
Amino acid position 342 (e.g., W342G)[50]
Amino acid position 354 (e.g., R354X)[9]
Amino acid position 361 (e.g., Q361X)[57]
Amino acid position 366 (e.g., V366D)[57]
Amino acid position 386 (e.g., G386X)[34]
Δ Amino acid positions 383-389[57]
Amino acid position 387 (e.g., R387H)[9]
Amino acid position 390 (e.g., A390P)[7]
Amino acid position 410 (e.g., G410D)[7]
Amino acid position 413 (e.g., L413W)[7]
Amino acid position 415 (e.g., R415X)[42]
Amino acid position 420 (e.g., I420T)[9]
Amino acid position 454 (e.g., V454X)[49]
Amino acid position 455 (e.g., G455E)[9]

TABLE 4-continued

Selected ABCB11 Mutations Associated with PFIC-2

Amino acid position 461 (e.g., K461E)[2,7]
Amino acid position 463 (e.g., T463I)[7]
Amino acid position 466 (e.g., Q466K)[7]
Amino acid position 470 (e.g., R470Q[7], R470X[9])
Amino acid position 472 (e.g., Y472X[14], Y472C[27])
Amino acid position 475 (e.g., C475X)[29]
Amino acid position 481 (e.g., V481E)[7]
Amino acid position 482 (e.g., D482G)[2,7]
Amino acid position 484 (e.g., H484Rfs*5)[9]
Amino acid position 487 (e.g., R487H[2], R487P[84])
Amino acid position 490 (e.g., N490D)[7]
Amino acid position 493 (e.g., W493X)[8]
Amino acid position 498 (e.g., I498T)[7]
Amino acid position 501 (e.g., V501G)[68]
Amino acid position 512 (e.g., I512T)[7]
Amino acid position 515 (e.g., N515T[7], N515D[64])
Amino acid position 516 (e.g., I516M)[17]
Amino acid position 517 (e.g., R517H)[7]
Amino acid position 520 (e.g., R520X)[57]
Amino acid position 523 (e.g., A523G)[13]
Amino acid position 528 (e.g., I528X)[9]
Amino acid position 540 (e.g., F540L)[46]
Amino acid position 541 (e.g., I541L[7], I541T[17])
Amino acid position 548 (e.g., F548Y)[7]
Amino acid position 549 (e.g., D549V)[9]
Amino acid position 554 (e.g., E554K)[21]
Amino acid position 559 (e.g., M559T)[57]
Amino acid position 562 (e.g., G562D)[7]
Amino acid position 570 (e.g., A570T[7], A570V[26])
Amino acid position 575 (e.g., R575X[2], R575Q[21])
Amino acid position 588 (e.g., A588V)[7]
Amino acid position 591 (e.g., N591S)[9,17]
Amino acid position 593 (e.g., S593R)[2,7]
Amino acid position 597 (e.g., V597V[9], V597L[13])
Amino acid positions 591 and 597 (e.g., N591S + V597V)[9]
Amino acid position 603 (e.g., K603K)[55]
Amino acid position 609 (e.g., H609Hfs*46)[26]
Amino acid position 610 (e.g., I610Gfs*45)[9]
Amino acid position 615 (e.g., H615R)[26]
Amino acid position 625 (e.g., T625Nfs*5)[26]
Amino acid position 627 (e.g., I627T)[7]
Amino acid position 636 (e.g., E636G)[2]
Amino acid position 669 (e.g., I669V)[26]
Amino acid position 698 (e.g., R609H)[9]
Amino acid positions 112 and 698 (e.g., I112T + R698H)[9]
Amino acid position 699 (e.g., S699P)[9]
Amino acid position 766 (e.g., G766R)[24]
Amino acid position 806 (e.g., G806G)[55]
Amino acid position 824 (e.g., G824E)[42]
Amino acid position 832 (e.g., R832C[7,26], R832H[41])
Amino acid position 842 (e.g., D842G)[2]
Amino acid position 859 (e.g., T859R)[7]
Amino acid position 865 (e.g., A865V)[45]
Amino acid position 877 (e.g., G877R)[56]
Amino acid position 893 (e.g., A893V)[57]
Amino acid position 901 (e.g., S901R)[17]
Amino acid position 903 (e.g., V903G)[57]
Δ Amino acid position 919[12]
Amino acid position 928 (e.g., R928X)[15,21]
Amino acid position 930 (e.g., K930Efs*79[10], K930Efs*49[26])
Amino acid position 948 (e.g., R948C)[7,26]
Amino acid position 979 (e.g., N979D)[7]
Amino acid position 982 (e.g., G982R)[2,7]
Amino acid positions 444 and 982 (e.g., V444A + G982R)[38]
Amino acid position 1001 (e.g., R1001R)[9]
Amino acid position 1003 (e.g., G1003R)[24]
Amino acid position 1004 (e.g., G1004D)[2,7]
Amino acid position 1027 (e.g., S1027R)[26]
Amino acid position 1028 (e.g., A1028A)[10]
Amino acid position 1032 (e.g., G1032R)[12]
Amino acid position 1041 (e.g., Y1041X)[9]
Amino acid position 1050 (e.g., R1050C)[57]
Amino acid position 1053 (e.g., Q1053X)[57]
Amino acid position 1055 (e.g., L1055P)[36]
Amino acid position 1057 (e.g., R1057X)[2]
Amino acid position 1058 (e.g., Q1058Hfs*38[9], Q1058fs*38[17])
Amino acid position 1061 (e.g., I1061Vfs*34)[9]
Amino acid position 1083 (e.g., C1083Y)[47]
Amino acid position 1090 (e.g., R1090X)[2]
Amino acid position 1099 (e.g., L1099Lfs*38)[26]
Amino acid position 1100 (e.g., S1100Qfs*38)[13]
Amino acid position 1110 (e.g., A1110E)[7]
Amino acid position 1116 (e.g., G1116R[7], G1116F[9,17], G1116E[36])
Amino acid position 1128 (e.g., R1128C)[7,13]
Amino acid position 1131 (e.g., D1131V)[27]
Amino acid position 1144 (e.g., S1144R)[7]
Amino acid position 1153 (e.g., R1153C[2,7], R1153H[7,26])
Amino acid position 1154 (e.g., S1154P)[7]
Amino acid position 1173 (e.g., N1173D)[57]
Amino acid position 1192 (e.g., A1192Efs*50)[9]
Amino acid position 1198 (e.g., H1198R)[27]
Amino acid position 1210 (e.g., T1210P[7], T1210F[57])
Amino acid position 1211 (e.g., N1211D)[7]
Amino acid position 1212 (e.g., V1212F)[36]
Amino acid position 1231 (e.g., R1231W[7], R1223Q[7])
Amino acid position 1232 (e.g., A1232D)[17]
Amino acid position 1235 (e.g., R1235X)[12]
Amino acid position 1242 (e.g., L1242I)[7]
Amino acid position 1256 (e.g., T1256fs*1296)[83]
Amino acid position 1268 (e.g., R1268Q)[2,7]
Amino acid position 1302 (e.g. E1302X)[57]
Amino acid position 1311 (e.g., Y1311X)[57]
Amino acid position 1316 (e.g., T1316Lfs*64)[15]
Intron 4 ((+3)A > C)[1]
Splice site mutation IVS7 + 1G > A[14]
IVS8 + 1G > C[76]
Splice site mutation IVS9 + 1G > T[14]
Splice site mutation IVS13del-13^-8[14]
Splice site mutation IVS16 − 8T > G[14]
Splice site mutation IVS18 + 1G > A[14]
Splice site mutation IVS19 + 2T > C[14]
IVS 23 − 8 G − A[36]
IVS24 + 5G > A[51]
Putative splice mutation 1198 − 1G > C[17]
Putative splice mutation 1810 − 3C > G[17]
Putative splice mutation 2178 + 1G > A[17]
Putative splice mutation 2344 − 1G > T[17]
Putative splice mutation 3213 + 1__3213 + 2delinsA[17]
c.-24C > A[78]
c.76 13 G > T[9]
c.77 − 19T > A[52]
c.90__93delGAAA[18]
c.124G > A[69]
c.150 + 3 A > C[10]
c.249__250insT[18]
c.611 + 1G > A[84]
c.611 + 4A > G[36]
c.612 − 15__-6del10bp[55]
c.625A > C[31]
c.627 + 5G > T[31]
c.625A > C/c.627 + 5G > T[31]
c.886C > T[31]
c.890A > G[59]
c.908 + 1G > A[57]
c.908 + 5G > A[55]
c.908delG[59]
1273 1 bp deletion[91]
c.1084 − 2A > G[57]
c.1445A > G[59]
c.1587-1589delCTT[31]
c.1621A > C[59]
1939delA[14]
c.2081T > A[31]
2098delA[16]
c.2343 + 1 G > T[80]
c.2178 + 1G > T[36]
c.2417G > A[78]
c.2620C > T[32]
c.2815 − 8A > G[55]
c.3003A > G[37]
c.3213 + 4 A > G[9,37]
c.3213 + 5 G > A[9]
c.3268C > T[75]
c.3382C > T[75]

TABLE 4-continued

Selected ABCB11 Mutations Associated with PFIC-2 c.3765(+1 + 5)del5[42]
c.3767-3768insC[6]
1145delC[8]
Ex13_Ex17del[82]

[A] A mutation to 'X' denotes an early stop codon

REFERENCES FOR TABLES 3 AND 4

[1] Noe et al., J Hepatol. 2005, vol. 43(3), p. 536-543.
[2] Lam et al., Am J Physiol Cell Physiol. 2007, vol. 293(5), p. C1709-16.
[3] Stindt et al., Liver Int. 2013, vol. 33(10), p. 1527-1735.
[4] Gao et al., Shandong Yiyao 2012, vol. 52(10), p. 14-16.
[5] Strautnieks et al., Gastroenterology. 2008, vol. 134(4), p. 1203-1214.
[6] Kagawa et al., Am J Physiol Gastrointest Liver Physiol. 2008, vol. 294(1), p. G58-67.
[7] Byrne et al., Hepatology. 2009, vol. 49(2), p. 553-567.
[8] Chen et al., J Pediatr. 2008, vol. 153(6), p. 825-832.
[9] Davit-Spraul et al., Hepatology 2010, vol. 51(5), p. 1645-1655.
[10] Dröge et al., Sci Rep. 2016, vol. 6: 24827.
[11] Lang et al., Pharmacogenet Genomics. 2007, vol. 17(1), p. 47-60.
[12] Ellinger et al., World J Gastroenterol. 2017, vol. 23(29), p.:5295-5303.
[13] Vitale et al., J Gastroenterol. 2018, vol. 53(8), p. 945-958.
[14] Knisely et al., Hepatology. 2006, vol. 44(2), p. 478-86.
[15] Ellis et al., Hepatology. 2018, vol. 67(4), p. 1531-1545.
[16] Lam et al., J Hepatol. 2006, vol. 44(1), p. 240-242.
[17] Varma et al., Hepatology 2015, vol. 62(1), p. 198-206.
[18] Treepongkaruna et al., World J Gastroenterol. 2009, vol. 15(34), p. 4339-4342.
[19] Zarenezhad et al., Hepatitis Monthly: 2017, vol. 17(2); e43500.
[20] Hayashi et al., Hepatol Res. 2016, vol. 46(2), p. 192-200.
[21] Guorui et al., Linchuang Erke Zazhi 2013, vol. 31(10), 905-909.
[22] van Mil et al., Gastroenterology. 2004, vol. 127(2), p. 379-384.
[23] Anzivino et al., Dig Liver Dis. 2013, vol. 45(3), p. 226-232.
[24] Park et al., World J Gastroenterol. 2016, vol. 22(20), p. 4901-4907.
[25] Imagawa et al., J Hum Genet. 2018, vol. 63(5), p. 569-577.
[26] Giovannoni et al., PLoS One. 2015, vol. 10(12): e0145021.
[27] Hu et al., Mol Med Rep. 2014, vol. 10(3), p. 1264-1274.
[28] Lang et al., Drug Metab Dispos. 2006, vol. 34(9), p. 1582-1599.
[29] Masahata et al., Transplant Proc. 2016, vol. 48(9), p. 3156-3162.
[30] Holz et al., Hepatol Commun. 2018, vol. 2(2), p. 152-154.
[31] Li et al., Hepatology International 2017, vol. 11, No. 1, Supp. Supplement 1, pp. S180. Abstract Number: OP284.
[32] Francalanci et al., Laboratory Investigation 2011, vol. 91, Supp. SUPPL. 1, pp. 360A. Abstract Number: 1526.
[33] Francalanci et al., Digestive and Liver Disease 2010, vol. 42, Supp. SUPPL. 1, pp. S16. Abstract Number: T.N.5.
[34] Shah et al., J Pediatr Genet. 2017, vol. 6(2), p. 126-127.
[35] Gao et al., Hepatitis Monthly 2017, vol. 17(10), e55087/1-e55087/6.
[36] Evason et al., Am J Surg Pathol. 2011, vol. 35(5), p. 687-696.
[37] Davit-Spraul et al., Mol Genet Metab. 2014, vol. 113(3), p. 225-229.
[38] Maggiore et al., J Hepatol. 2010, vol. 53(5), p. 981-6.
[39] McKay et al., Version 2. F1000Res. 2013; 2: 32. DOI: 10.12688/f1000research.2-32.v2
[40] Liu et al., Pediatr Int. 2013, vol. 55(2), p. 138-144.
[41] Waisbourd-Zinman et al., Ann Hepatol. 2017, vol. 16(3), p. 465-468.
[42] Griffin, et al., Canadian Journal of Gastroenterology and Hepatology 2016, vol. 2016. Abstract Number: A200. Meeting Info: 2016 Canadian Digestive Diseases Week, CDDW 2016. Montreal, QC, United States. 26 Feb. 2016-29 Feb. 2016
[43] Qiu et al., Hepatology 2017, vol. 65(5), p. 1655-1669.
[44] Imagawa et al., Sci Rep. 2017, 7:41806.
[45] Kang et al., J Pathol Transl Med. 2019 May 16. doi: 10.4132/jptm.2019.05.03. [Epub ahead of print]
[46] Takahashi et al., Eur J Gastroenterol Hepatol. 2007, vol. 19(11), p. 942-6.
[47] Shimizu et al., Am J Transplant. 2011, vol. 11(2), p. 394-398.
[48] Krawczyk et al., Ann Hepatol. 2012, vol. 11(5), p. 710-744.
[49] Sharma et al., BMC Gastroenterol. 2018, vol. 18(1), p. 107.
[50] Sattler et al., Journal of Hepatology 2017, vol. 66, No. 1, Suppl. S, pp. S177. Meeting Info.: International Liver Congress/52nd Annual Meeting of the European-Association-for-the-Study-of-the-Liver. Amsterdam, NETHERLANDS. Apr. 19-23, 2017. European Assoc Study Liver.
[51] Jung et al., J Pediatr Gastroenterol Nutr. 2007, vol. 44(4), p. 453-458.
[52] Sciveres. Digestive and Liver Disease 2010, vol. 42, Supp. SUPPL. 5, pp. S329. Abstract Number: CO18. Meeting Info: 17th National Congress SIGENP. Pescara, Italy. 7 Oct. 2010-9 Oct. 2010
[53] Sohn et al., Pediatr Gastroenterol Hepatol Nutr. 2019, vol. 22(2), p. 201-206.
[54] Ho et al., Pharmacogenet Genomics. 2010, vol. 20(1), p. 45-57.
[55] Wang et al., Hepatol Res. 2018, vol. 48(7), p. 574-584.
[56] Shaprio et al., J Hum Genet. 2010, vol. 55(5), p. 308-313.
[57] Bounford. University of Birmingham. Dissertation Abstracts International, (2016) Vol. 75, No. 1C. Order No.: AA110588329. ProQuest Dissertations & Theses.
[58] Stolz et al., Aliment Pharmacol Ther. 2019, vol. 49(9), p. 1195-1204.
[59] Jankowska et al., J Pediatr Gastroenterol Nutr. 2014, vol. 58(1), p. 92-95.
[60] Kim. Journal of Pediatric Gastroenterology and Nutrition 2016, vol. 62, Supp. SUPPL. 1, pp. 620. Abstract Number: H-P-045. Meeting Info: 49th Annual Meeting of the European Society for Paediatric Gastroenterology, Hepatology and Nutrition, ESPGHAN 2016. Athens, Greece. 25 May 2016-28 May 2016.
[61] Pauli-Magnus et al., Hepatology 2003, vol. 38, No. 4 Suppl. 1, pp. 518A. print. Meeting Info.: 54th Annual Meeting of the American Association for the Study of Liver Diseases. Boston, Mass., USA. Oct. 24-28, 2003. American Association for the Study of Liver Diseases.
[62] Li et al., Hepatology International 2017, vol. 11, No. 1, Supp. Supplement 1, pp. S362. Abstract Number: PP0347. Meeting Info: 26th Annual Conference of the Asian Pacific Association for the Study of the Liver, APASL 2017. Shanghai, China. 15 Feb. 2017-19 Feb. 2017.

[63] Rumbo et al., Transplantation 2018, vol. 102, No. 7, Supp. Supplement 1, pp. S848. Abstract Number: P.752. Meeting Info: 27th International Congress of The Transplantation Society, T T S 2018. Madrid, Spain. 30 Jun. 2018-5 Jul. 2018.

[64] Lee et al., Pediatr Gastroenterol Hepatol Nutr. 2017, vol. 20(2), p. 114-123.

[65] Sherrif et al., Liver international: official journal of the International Association for the Study of the Liver 2013, vol. 33, No. 8, pp. 1266-1270.

[66] Blackmore et al., J Clin Exp Hepatol. 2013, vol. 3(2), p. 159-161.

[67] Matte et al., J Pediatr Gastroenterol Nutr. 2010, vol. 51(4), p. 488-493.

[68] Lin et al., Zhongguo Dang Dai Er Ke Za Zhi. 2018, vol. 20(9), p. 758-764.

[69] Harmanci et al., Experimental and Clinical Transplantation 2015, vol. 13, Supp. SUPPL. 2, pp. 76. Abstract Number: P62. Meeting Info: 1st Congress of the Turkic World Transplantation Society. Astana, Kazakhstan. 20 May 2015-22 May 2015.

[70] Herbst et al., Mol Cell Probes. 2015, vol. 29(5), p. 291-298.

[71] Moghadamrad et al., Hepatology. 2013, vol. 57(6), p. 2539-2541.

[72] Holz et al., Zeitschrift fur Gastroenterologie 2016, vol. 54, No. 8. Abstract Number: KV275. Meeting Info: Viszeralmedizin 2016, 71. Jahrestagung der Deutschen Gesellschaft fur Gastroenterologie, Verdauungs- und Stoffwechselkrankheiten mit Sektion Endoskopie—10. Herbsttagung der Deutschen Gesellschaft fur Allgemein- und Viszeralchirurgie. Hamburg, Germany. 21 Sep. 2016-24 Sep. 2016.

[73] Wang et al., PLoS One. 2016; vol. 11(4): e0153114.

[74] Hao et al., International Journal of Clinical and Experimental Pathology 2017, vol. 10(3), p. 3480-3487.

[75] Arnell et al., J Pediatr Gastroenterol Nutr. 2010, vol. 51(4), p. 494-499.

[76] Sharma et al., Indian Journal of Gastroenterology 2017, vol. 36, No. 1, Supp. Supplement 1, pp. A99. Abstract Number: M-20. Meeting Info: 58th Annual Conference of the Indian Society of Gastroenterology, ISGCON 2017. Bhubaneswar, India. 14 Dec. 2017-17 Dec. 2017.

[77] Beauséjour et al., Can J Gastroenterol. 2011, vol. 25(6), p. 311-314.

[78] Imagawa et al., Journal of Pediatric Gastroenterology and Nutrition 2016, vol. 63, Supp. Supplement 2, pp. S51. Abstract Number: 166. Meeting Info: World Congress of Pediatric Gastroenterology, Hepatology and Nutrition 2016. Montreal, QC, Canada. 5 Oct. 2016-8 Oct. 2016.

[79] Peng et al., Zhonghua er ke za zhi (Chinese journal of pediatrics) 2018, vol. 56, No. 6, pp. 440-444.

[80] Tibesar et al., Case Rep Pediatr. 2014, vol. 2014: 185923.

[81] Ng et al., Journal of Pediatric Gastroenterology and Nutrition 2018, vol. 66, Supp. Supplement 2, pp. 860. Abstract Number: H-P-127. Meeting Info: 51st Annual Meeting European Society for Paediatric Gastroenterology, Hepatology and Nutrition, ESPGHAN 2018. Geneva, Switzerland. 9 May 2018-12 May 2018.

[82] Wong et al., Clin Chem. 2008, vol. 54(7), p. 1141-1148.

[83] Pauli-Magnus et al., J Hepatol. 2005, vol. 43(2), p. 342-357.

[84] Jericho et al., Journal of Pediatric Gastroenterology and Nutrition. 60, vol. 3, p. 368-374.

[85] Scheimann et al., Gastroenterology 2007, vol. 132, No. 4, Suppl. 2, pp. A452. Meeting Info.: Digestive Disease Week Meeting/108th Annual Meeting of the American-Gastroenterological-Association. Washington, D.C., USA. May 19-24, 2007. Amer Gastroenterol Assoc; Amer Assoc Study Liver Dis; Amer Soc Gastrointestinal Endoscopy; Soc Surg Alimentary Tract.

[86] Jaquotot-Haerranz et al., Rev Esp Enferm Dig. 2013, vol. 105(1), p. 52-54.

[87] Khosla et al., American Journal of Gastroenterology 2015, vol. 110, No. Suppl. 1, pp. S397. Meeting Info.: 80th Annual Scientific Meeting of the American-College-of-Gastroenterology. Honolulu, Hi., USA. Oct. 16-21, 2015.

[88] Dróge et al., J Hepatol. 2017, vol. 67(6), p. 1253-1264.

[89] Liu et al., Liver International 2010, vol. 30(6), p. 809-815.

[90] Chen et al., Journal of Pediatrics 2002, vol. 140(1), p. 119-124.

[91] U.S. Pat. No. 9,295,677

In some embodiments, the mutation in ABCB11 is selected from A167T, G238V, V284L, E297G, R470Q, R470X, D482G, R487H, A570T, N591S, A865V, G982R, R1153C, and R1268Q.

Provided are methods of treating PFIC (e.g., PFIC-1 and PFIC-2) in a subject that includes performing an assay on a sample obtained from the subject to determine whether the subject has a mutation associated with PFIC (e.g., a ATP8B1, ABCB11, ABCB4, TJP2, NR1H4 or Myo5b mutation), and administering (e.g., specifically or selectively administering) a therapeutically effective amount of a compound of formula (I), or a pharmaceutically acceptable salt thereof, to the subject determined to have a mutation associated with PFIC. In some embodiments, the mutation is an ATP8B1 or ABCB11 mutation. For example, a mutation as provided in any one of Tables 1-4. In some embodiments, the mutation in ATP8B1 is selected from L127P, G308V, T456M, D554N, F529del, I661T, E665X, R930X, R952X, R1014X, and G1040R. In some embodiments, the mutation in ABCB11 is selected from A167T, G238V, V284L, E297G, R470Q, R470X, D482G, R487H, A570T, N591S, A865V, G982R, R1153C, and R1268Q.

Also provided are methods for treating PFIC (e.g., PFIC-1 and PFIC-2) in a subject in need thereof, the method comprising: (a) detecting a mutation associated with PFIC (e.g., a ATP8B1, ABCB11, ABCB4, TJP2, NR1H4 or Myo5b mutation) in the subject; and (b) administering to the subject a therapeutically effective amount of crystal modification I of odevixibat. In some embodiments, methods for treating PFIC can include administering a therapeutically effective amount of a compound of formula (I), or a pharmaceutically acceptable salt thereof, to a subject having a mutation associated with PFIC (e.g., an ATP8B1, ABCB11, ABCB4, TJP2, NR1H4 or Myo5b mutation). In some embodiments, the mutation is an ATP8B1 or ABCB11 mutation. For example, a mutation as provided in any one of Tables 1-4. In some embodiments, the mutation in ATP8B1 is selected from L127P, G308V, T456M, D554N, F529del, I661T, E665X, R930X, R952X, R1014X, and G1040R. In some embodiments, the mutation in ABCB11 is selected from A167T, G238V, V284L, E297G, R470Q, R470X, D482G, R487H, A570T, N591S, A865V, G982R, R1153C, and R1268Q.

In some embodiments, the subject is determined to have a mutation associated with PFIC in a subject or a biopsy sample from the subject through the use of any art recognized tests, including next generation sequencing (NGS). In some embodiments, the subject is determined to have a mutation associated with PFIC using a regulatory agency-approved, e.g., FDA-approved test or assay for identifying a mutation associated with PFIC in a subject or a biopsy sample from the subject or by performing any of the non-limiting examples of assays described herein. Additional methods of diagnosing PFIC are described in Gunaydin, M. et al., Hepat Med. 2018, vol. 10, p. 95-104, incorporated by reference in its entirety herein.

In some embodiments, the treatment of PFIC (e.g., PFIC-1 or PFIC-2) decreases the level of serum bile acids in the subject. In some embodiments, the level of serum bile acids is determined by, for example, an ELISA enzymatic assay or the assays for the measurement of total bile acids as described in Danese et al., PLoS One. 2017, vol. 12(6): e0179200, which is incorporated by reference herein in its entirety. In some embodiments, the level of serum bile acids can decrease by, for example, 10% to 40%, 20% to 50%, 30% to 60%, 40% to 70%, 50% to 80%, or by more than 90% of the level of serum bile acids prior to administration of crystal modification I of odevixibat. In some embodiments, the treatment of PFIC includes treatment of pruritus.

Thus, in one embodiment, the invention relates to crystal modification 1 of odevixibat described herein for use in the treatment or prevention of a disease or disorder as listed above.

In another embodiment, the invention relates to the use of crystal modification 1 of odevixibat described herein in the manufacture of a medicament for the treatment or prevention of a disease or disorder as listed above.

In yet another embodiment, the invention relates to a method of treatment or prevention of a disease or disorder as listed above in a warm-blooded animal, comprising administering a therapeutically effective amount of crystal modification 1 of odevixibat described herein to a warm-blooded animal in need of such treatment and/or prophylaxis.

Another aspect of the invention relates to a pharmaceutical composition comprising a therapeutically effective amount of crystal modification 1 of odevixibat described herein, in association with a pharmaceutically acceptable diluent or carrier.

The pharmaceutical composition may further comprise at least one other active substance, such as an active substance selected from an IBAT inhibitor; an enteroendocrine peptide or enhancer thereof; a dipeptidyl peptidase-IV inhibitor; a biguanidine; an incretin mimetic; a thiazolidinone; a PPAR agonist; a HMG Co-A reductase inhibitor; a bile acid binder; a TGR5 receptor modulator; a member of the prostone class of compounds; a guanylate cyclase C agonist; a 5-HT4 serotonin agonist; or a pharmaceutically acceptable salt of any one these active substances. Examples of such combinations are also described in WO2012/064268.

Crystal modification 1 of odevixibat can be administered to a warm-blooded animal at a unit dose within the range of about 0.01 to 1.0 mg/kg, such as about 0.01 to 0.5 mg/kg, or such as about 0.01 to 0.2 mg/kg, and this can provide a therapeutically effective dose. A unit dose form, such as a tablet or capsule, can contain about 0.1 to 20 mg of active ingredient, such as about 0.1 to 10 mg, or such as about 0.2 to 5 mg, or such as about 0.2 to 1.0 mg. The daily dose can be administered as a single dose or divided into one, two, three or more unit doses. An orally administered daily dose of odevixibat is preferably within about 0.1 to 50 mg, more preferably within about 0.1 to 20 mg, such as within about 0.2 to 10 mg, or such as within about 0.2 to 5.0 mg.

Pharmaceutical formulations of odevixibat may comprise a therapeutically effective amount of crystal modification 1 of odevixibat, and one or more pharmaceutically acceptable excipients. The excipients may e.g. include fillers, binders, disintegrants, glidants and lubricants. In general, pharmaceutical compositions may be prepared in a conventional manner using conventional excipients.

In some embodiments, the pharmaceutical formulation is a multiparticulate formulation containing low doses of crystal modification 1 of odevixibat. Such a formulation enables weight-based dosing and may be particularly suitable for administering to paediatric patients. In some embodiments, the pharmaceutical formulation is a paediatric formulation.

In some embodiment, the particles are small enough that they can be sprinkled onto food and easily swallowed. In some embodiments, the particles can be swallowed without causing a perception of grittiness. In some embodiments, the particles do not give the patient an urge to chew the particles.

In some embodiments, each particle comprises a core and a coating layer surrounding the core. The core of each particle may be a pellet, a granule, a minitablet, a bead, a microparticle or a microsphere. The active pharmaceutical ingredient may be in the core or in the coating layer. In some embodiments, the coating layer of each particle comprises the active pharmaceutical ingredient, while the core of each particle does not comprise the active pharmaceutical ingredient.

The cores may be orally dispersible and comprise soluble ingredients such as a sugar (e.g., sucrose) or a soluble polymer (e.g. hydroxypropyl methylcellulose) or may be non-orally dispersible and comprise non-soluble ingredients such as a non-soluble polymer (e.g., microcrystalline cellulose). In some embodiments, the cores are microcrystalline cellulose spheres.

The coating layer can further comprise a film-forming polymer, such as a cellulose-based polymer, a polysaccharide-based polymer, an N-vinylpyrrolidone-based polymer, an acrylate, an acrylamide, or copolymers thereof. Examples of suitable film-forming polymers include polyvinyl alcohol (PVA), polyvinyl acetate phthalate (PVAP), polyethylene glycol (PEG), polyvinylpyrrolidone (PVP), methacrylic acid copolymers, starch, hydroxypropyl starch, chitosan, shellac, methyl cellulose, hydroxypropyl cellulose (HPC), low-substituted hydroxypropyl cellulose, hydroxypropyl methylcellulose (HPMC; or hypromellose), hydroxypropyl methylcellulose acetate succinate (HPMCAS), hydroxypropyl methylcellulose phthalate (HPMCP), cellulose acetate phthalate (CAP), cellulose acetate trimellitate (CAT), as well as combinations thereof, such as a mixture of methyl cellulose and hydroxypropyl methylcellulose (metolose). In some embodiments, the coating layer comprises a film-forming polymer selected from the group consisting of hydroxypropyl methylcellulose, polyvinyl alcohol (PVA), polyethylene glycol (PEG), starch, hydroxypropyl starch and hydroxypropyl cellulose (HPC).

The coating layer may optionally comprise one or more additional ingredients, such as a plasticizer (e.g. polyethylene glycol, triacetin or triethyl citrate), an anti-tack agent (e.g. talc or magnesium stearate) or a colouring agent (e.g. titanium dioxide, iron oxides, riboflavin or turmeric).

The dosage required for the therapeutic or prophylactic treatment will depend on the route of administration, the severity of the disease, the age and weight of the patient and other factors normally considered by the attending physician when determining the individual regimen and dosage levels appropriate for a particular patient.

Definitions

The term "crystal modification" refers to a crystalline solid phase of an organic compound. A crystal modification can be either a solvate or an ansolvate.

The term "solvate" refers to a crystalline solid phase of an organic compound, which has solvent (i.e., solvent molecules) incorporated into its crystal structure. A "hydrate" is a solvate wherein the solvent is water.

The term "sesquihydrate" refers to a hydrate containing about 1.5 moles of water associated with the crystal per mole of organic compound (i.e., a 1.5 hydrate). As used herein, a sesquihydrate includes from about 1.2 to about 1.8, more preferably from about 1.3 to about 1.7, more preferably from about 1.4 to about 1.6 and even more preferably from about 1.45 to about 1.55 moles of water associated with each mole of odevixibat in a crystal. The amount of water calculated herein excludes water adsorbed to the surface of the crystal.

The term "mixed solvate" refers to a crystalline solid phase of an organic compound, which has two or more different solvent molecules incorporated into its crystal structure. One of the at least two solvent molecules may be water.

The term "isostructural solvate" refers to a crystalline solid phase of an organic compound, wherein the crystalline solid phase can accommodate different solvents without distortion of the crystalline structure.

The term "slurry" refers to a saturated solution to which an excess of solid is added, thereby forming a mixture of solid and saturated solution.

As used herein, the term "void volumes" refers to channels, layers or other more or less isolated voids in the crystal structure.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

As used herein, the term "pharmaceutically acceptable" refers to those compounds, materials, compositions and/or dosage forms that are suitable for human pharmaceutical use and that are generally safe, non-toxic and neither biologically nor otherwise undesirable.

As used herein, the term "about" refers to a value or parameter herein that includes (and describes) embodiments that are directed to that value or parameter per se. For example, description referring to "about 20" includes description of "20." Numeric ranges are inclusive of the numbers defining the range. Generally speaking, the term "about" refers to the indicated value of the variable and to all values of the variable that are within the experimental error of the indicated value (e.g., within the 95% confidence interval for the mean) or within 10 percent of the indicated value, whichever is greater.

The crystallinity of a crystalline sample of odevixibat may be measured e.g. by X-Ray Powder Diffraction (XRPD) methods or by Differential Scanning Calorimetry (DSC) methods, such as the method disclosed in the experimental section. When reference is made herein to a crystalline compound, preferably the crystallinity as measured by DSC methods is greater than about 70%, such as greater than about 80%, particularly greater than about 90%, more particularly greater than about 95%. In some embodiments, the degree of crystallinity as measured by DSC methods is greater than about 98%. In some embodiments, the degree of crystallinity as measured by DSC methods is greater than about 99%. The % crystallinity refers to the percentage by weight of the total sample mass which is crystalline.

Preferably a crystal modification according to the invention is substantially free from other crystal modifications of the compound. Preferably, the described crystal modifications of odevixibat include less than, for example, about 20%, about 15%, about 10%, about 5%, about 3%, or particularly, less than about 1% by weight of other crystal modifications of odevixibat. Thus, preferably, the solid phase purity of the described crystal modifications of odevixibat is greater than about 80%, greater than about 85%, greater than about 90%, greater than about 95%, greater than about 97%, or particularly greater than about 99%.

The invention will now be described by the following examples which do not limit the invention in any respect. All cited documents and references mentioned herein are incorporated by reference in their entireties.

Abbreviations

DMF dimethylformamide
DMSO dimethyl sulfoxide
EtOH ethanol
MeOH methanol
RH relative humidity
2-PrOH 2-propanol

EXPERIMENTAL METHODS

X-Ray Powder Diffraction (XRPD) Analysis

Analyses were performed at 22° C. on a PANalytical X'Pert Pro diffractometer equipped with a Cu long fine focus X-ray tube and a PIXcel detector. Automatic divergence and anti-scatter slits were used together with 0.02 rad Soller slits and a Ni-filter. Dry samples were smeared onto cut Silicon Zero Background Holders (ZBH) and analysed between 2-40° in 2-theta with an analysis time of 17 minutes. All slurry samples were dripped on tempered porous Alumina filter substrates and analysed twice as they dried, first with a one minute 16-second scan (2-30° in 2-theta) and then a 7-minute scan (2-30° in 2-theta). A final 17-minute scan was performed when the sample had dried for several hours.

The samples were spun during analysis in order to increase the randomness of the samples. The following experimental settings were used:

Tube tension and current: 40 kV, 50 mA
Wavelength alpha1 (CuKα1): 1.5406 Å
Wavelength alpha2 (CuKα2): 1.5444 Å
Wavelength alpha1 and alpha2 mean (CuKα): 1.5418 Å

It is known in the art that an X-ray powder diffraction pattern may be obtained having one or more measurement errors depending on measurement conditions (such as equipment, sample preparation or machine used). In particular, it is generally known that intensities in an XRPD pattern may fluctuate depending on measurement conditions and sample preparation. For example, persons skilled in the art of XRPD will realise that the relative intensities of peaks may vary according to the orientation of the sample under the test and on the type and setting of the instrument used. The skilled person will also realise that the position of reflections can be affected by the precise height at which the sample sits in the diffractometer and the zero calibration of the diffractometer. The surface planarity of the sample may also have a small effect. Hence a person skilled in the art will appreciate that the diffraction pattern presented herein is not to be construed as absolute and any crystalline form that provides a powder diffraction pattern substantially identical to those disclosed herein fall within the scope of the present disclosure (for further information, see R. Jenkins and R. L. Snyder, "Introduction to X-ray powder diffractometry", John Wiley & Sons, 1996).

Thermogravimetric Analysis (TGA)

The analyses were performed on a Mettler TGA/SDTA 851e, equipped with a Julabo FP40 cooler. 1-10 mg of sample was weighed into 100 µL Al-cups and flushed with dry nitrogen gas during the analysis. Two different methods were used: in the "standard scan" the sample was scanned from 25 to 200° C. with a scan rate of 10° C./minute, and in the "careful scan" the sample was kept at 25° C. for 30 minutes and was then scanned from 25 to 100° C. with a scan rate of 10° C./minute.

Dynamic Vapor Sorption (DVS)

DVS measurements were performed with an SPS11-100n "Sorptions Prufsystem" from ProUmid (formerly "Projekt Messtechnik"), August-Nagel-Str. 23, 89079 Ulm (Germany). About 20 mg of sample was used. Humidity change rates of 5% per hour were used. The sample was placed on an aluminum or platinum holder on top of a microbalance and allowed to equilibrate at 0% RH before starting the pre-defined humidity program:

(1) 5h at 0% RH
(2) 0→95% RH (5%/h); 5 h at 95% RH
(3) 95→0% RH (5%/h); 5 h at 0% RH
(4) 0→95% RH (5%/h); 5 h at 95% RH
(5) 95→0% RH (5%/h); 5 h at 0% RH

High-Performance Liquid Chromatography (HPLC)

Analyses were performed on an Agilent, Series 1100, equipped with an Agilent 1260 Infinity degasser. Column: Waters XSelcet CHS C18 (150×3 mm, 3.5 am); Mobile phase A: 0.1% formic acid in water, mobile phase B: 0.1% formic acid in acetonitrile; Gradient 45% to 90% B; flow rate 0.425 mL/min; Acquisition time 35 minutes; Run time 42 minutes; Wave length: 283 nm; Column temperature 20° C. The Chromeleon Version 6.8 software was used.

Differential Scanning Calorimetry (DSC)

Experiments were performed using a TA Instruments Q2000 Differential Scanning Calorimeter. The DCS crucible used was a TZero aluminum pan with pinhole (diameter >0.2 mm) in the lid. A dry nitrogen purge at a constant flow rate of 50 mL/min was maintained in the DSC cell throughout the measurement.

EXAMPLES

Example 1

Preparation of Crystal Modification 1

Absolute alcohol (100.42 kg) and crude odevixibat (18.16 kg) were charged to a 250-L GLR with stirring under nitrogen atmosphere. Purified water (12.71 kg) was added and the reaction mass was stirred under nitrogen atmosphere at 25±5° C. for 15 minutes. Stirring was continued at 25±5° C. for 3 to 60 minutes, until a clear solution had formed. The solution was filtered through a 5.0µ SS cartridge filter, followed by a 0.2µ PP cartridge filter and then transferred to a clean reactor. Purified water (63.56 kg) was added slowly over a period of 2 to 3 hours at 25±5° C., and the solution was seeded with crystal modification 1 of odevixibat. The solution was stirred at 25±5° C. for 12 hours. During this time, the solution turned turbid. The precipitated solids were filtered through centrifuge and the material was spin dried for 30 minutes. The material was thereafter vacuum dried in a Nutsche filter for 12 hours. The material was then dried in a vacuum tray drier at 25±5° C. under vacuum (550 mm Hg) for 10 hours and then at 30±5° C. under vacuum (550 mm Hg) for 16 hours. The material was isolated as an off-white crystalline solid. The isolated crystalline material was milled and stored in LDPE bags.

An overhydrated sample was analyzed with XRPD and the diffractogram is shown in FIG. 2. Another sample was dried at 50° C. in vacuum and thereafter analysed with XRPD. The diffractogram of the dried sample is shown in FIG. 1.

The diffractograms for the drying of the sample are shown in FIGS. 3 and 4 for 2θ ranges 5-13° and 18-25°, respectively (overhydrated sample at the bottom and dry sample at the top).

Example 2

Preparation of Crystal Modification 2A from Ethanol and Water 105.9 mg of odevixibat were weighed into a 1 mL Chromacol vessel. A magnetic stir bar and 1.0 mL of an ethanol:water 70:30% v/v mixture were added and the vessel was closed with a crimped cap. The resulting slurry was then left stirred at 25° C. for 1 week.

The wet sample was analyzed with XRPD and the diffractogram is shown in FIG. 6. Upon drying of the sample, it transformed into crystal modification 1.

Example 3

Preparation of Crystal Modification 2A from Acetone and Water 27.0 mg of odevixibat were weighed into a 1 mL Chromacol vessel. A magnetic stir bar and 0.5 mL of a acetone:water 50:50% v/v mixture were added and the vessel was closed with a crimped cap. The resulting slurry was then left stirred at 3° C. for 2 weeks.

The wet sample was analyzed with XRPD and the diffractogram is shown in FIG. 7. Upon drying of the sample, it transformed into crystal modification 1.

Example 4

Preparation of Crystal Modification 2A from 2-Propanol and Water 27.4 mg of odevixibat were weighed into a 1 mL Chromacol vessel. A magnetic stir bar and 0.5 mL of a 2-propanol:water 50:50% v/v mixture were added and the vessel was closed with a crimped cap. The resulting slurry was then left stirred at 3° C. for 2 weeks.

The wet sample was analyzed with XRPD and the diffractogram is shown in FIG. 8. Upon drying of the sample, it transformed into crystal modification 1.

Example 5

Preparation of Crystal Modification 2A from 1,4-Dioxane and Water 31.6 mg of odevixibat were weighed into a 1 mL Chromacol vessel. A magnetic stir bar and 0.5 mL of a 1,4-dioxane:water 50:50% v/v mixture were added and the vessel was closed with a crimped cap. The resulting slurry was then left stirred at 3° C. for 2 weeks.

The wet sample was analyzed with XRPD and the diffractogram is shown in FIG. 9. Upon drying of the sample, it transformed into crystal modification 1.

Example 6

Preparation of Crystal Modification 2B from Methanol 103.9 mg of odevixibat were weighed into a 1 mL Chromacol vessel. A magnetic stir bar and 0.9 mL of methanol was added and the vessel was closed with a crimped cap. The resulting slurry was then left stirred at 22° C. for 1 week.

The wet sample was analyzed with XRPD and the diffractogram is shown in FIG. 9. Upon drying of the sample, it transformed into crystal modification 1.

Example 7

Preparation of Crystal Modification 2B from Acetonitrile and Water 20.2 mg of odevixibat were dissolved in 1.5 mL acetonitrile. To the stirred solution, 2.5 mL water was added as an antisolvent. Within 20-30 minutes a slurry had precipitated.

The wet sample was analyzed with XRPD and the diffractogram is shown in FIG. 10. Upon drying of the sample, it transformed into crystal modification 1.

Example 8

Preparation of Crystal Modification 2C from DMSO and Water 29.8 mg of odevixibat were weighed into a 1 mL Chromacol vessel. A magnetic stir bar and 0.5 mL of a DMSO:water 50:50% v/v mixture were added and the vessel was closed with a crimped cap. The resulting slurry was then left stirred at 3° C. for 2 weeks.

The wet sample was analyzed with XRPD and the diffractogram is shown in FIG. 12. Upon drying of the sample, it transformed into crystal modification 1.

Example 9

Analysis of the Water and Solvent Content of Crystal Modifications 1 and 2

Figure 13:
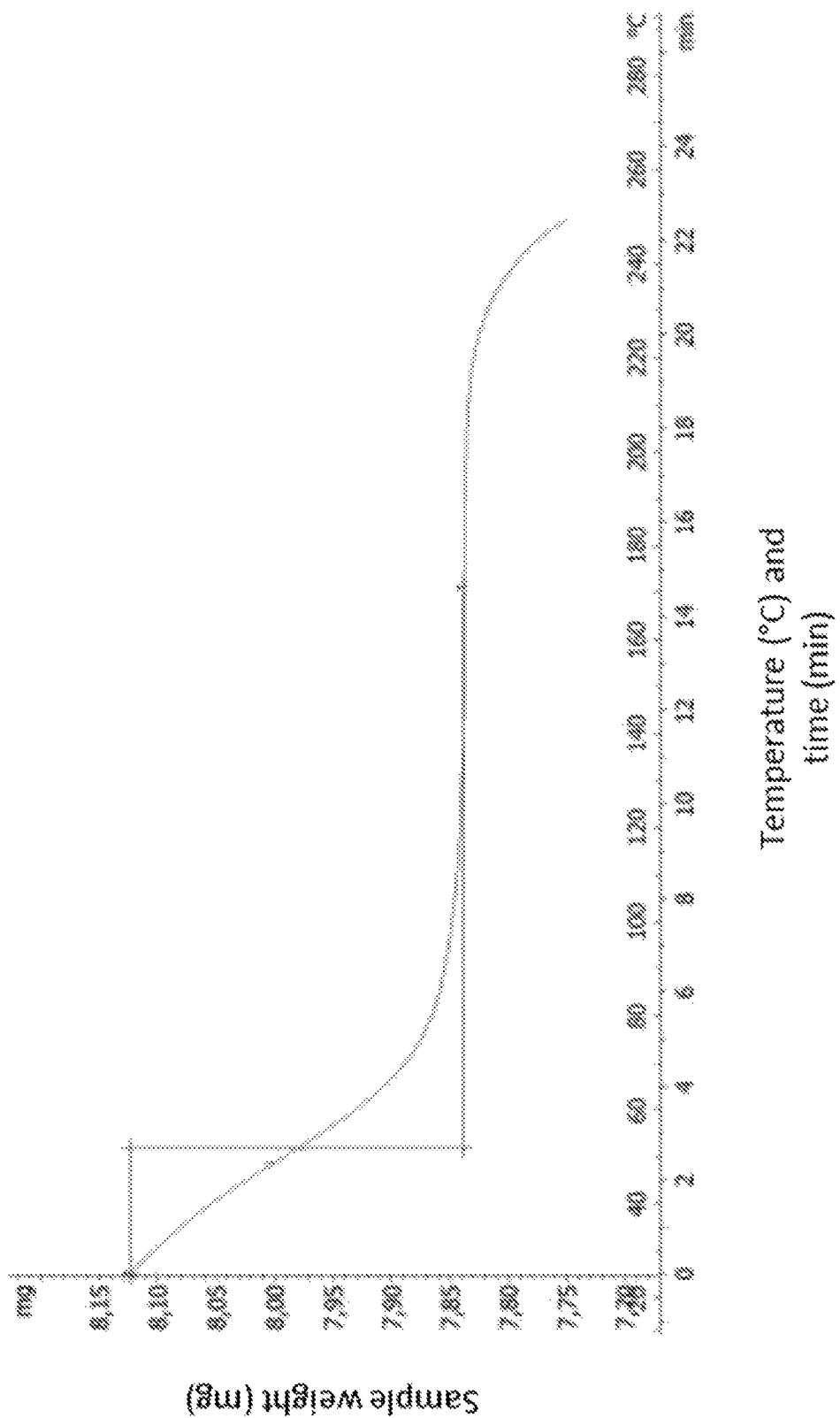
FIG. 13 shows the thermogravimetric analysis (TGA) mass change plot for crystal modification 1.

Karl-Fischer analysis of crystals of modification 1 showed a water content of 3.4% w/w. Thermal gravimetric analysis (TGA) of the same material showed a total mass loss of 3.5% (see FIG. 13). These similar findings indicate that crystal modification 1 contains 1.5 moles of water per mole of odevixibat, corresponding to a 1.5 hydrate.

The water and solvent content in crystal modification 2 were analysed by using samples prepared from a slurry of odevixibat in ethanol:water (60:40% v/v) that had been allowed to equilibrate during 3 days. Form 2 had formed according to XRPD. Slurry samples were taken from the slurry to Porous Plates and then stored in a desiccator with ethanol:water (60:40% v/v) and equilibrated at least overnight. Plates were taken out and dried in air for a certain time (5-30 minutes), and then analysed with a fast scan on XRPD (1 min 16 s) to verify the crystal form. Some samples contained crystal modification 2 and were still very wet, whereas crystal modification 1 already started to appear in the drier samples. Karl-Fischer analysis of the dried samples of crystal modification 2 indicated a water content of slightly more than 4% w/w. Thermal gravimetric analysis of the very wet samples of crystal modification 2 showed that these samples initially lost a lot of mass. A change in drying rate was thereafter observed, which probably indicates the start of the transformation from modification 2 to modification 1. After performing several experiments, a mass loss of approximately 12% w/w could be determined for the transformation of modification 2 to modification 1. Since dry modification 1 is a sesquihydrate (see FIG. 13), the total mass loss of approximately 12% (w/w) for the transformation of crystal modification 2 to crystal modification 1 would correspond to a loss of two moles of ethanol and 0.5 moles of water.

Figure 14:
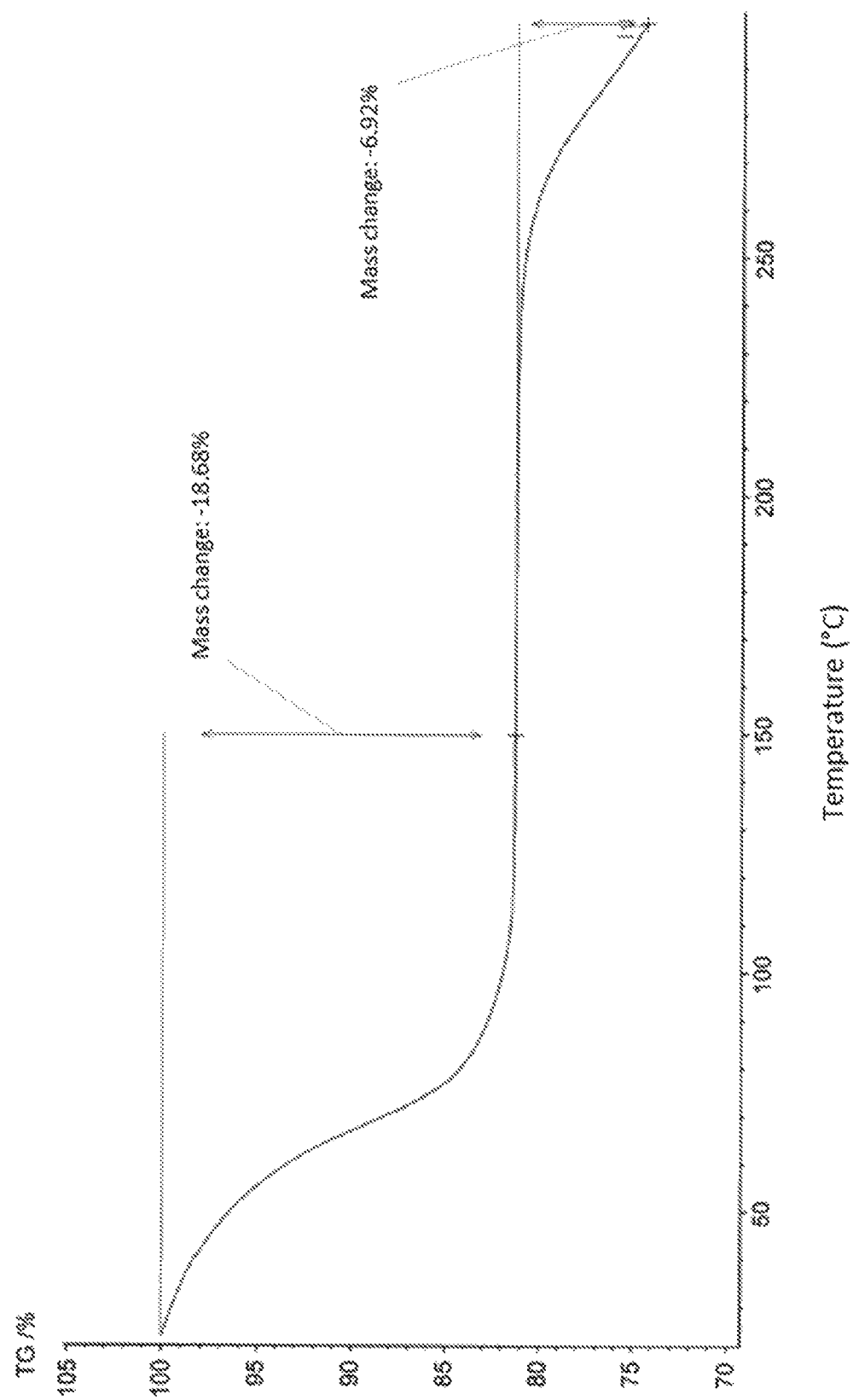
FIG. 14 shows the thermogravimetric analysis (TGA) mass change plot for crystal modification 2 produced by exposure of crystal modification 1 to the vapor phase of a mixture of ethanol and water

In another experiment, a sample of crystal modification 1 was kept in a dessicator and exposed to the vapour phase of a 60:40 (% v/v) mixture of ethanol and water for 4 days at room temperature. Thermal gravimetric analysis of the sample showed a mass loss of about 18.7% (see FIG. 14). The mass loss begins readily at the beginning of the experiment. Further examination of the sample by 1H-NMR suggested that the ethanol content corresponded to about 2.7 equivalents and the water content to about 1.9 equivalents.

Example 10

Dynamic Vapor Sorption Analysis of Crystal Modification 1

Figure 15:
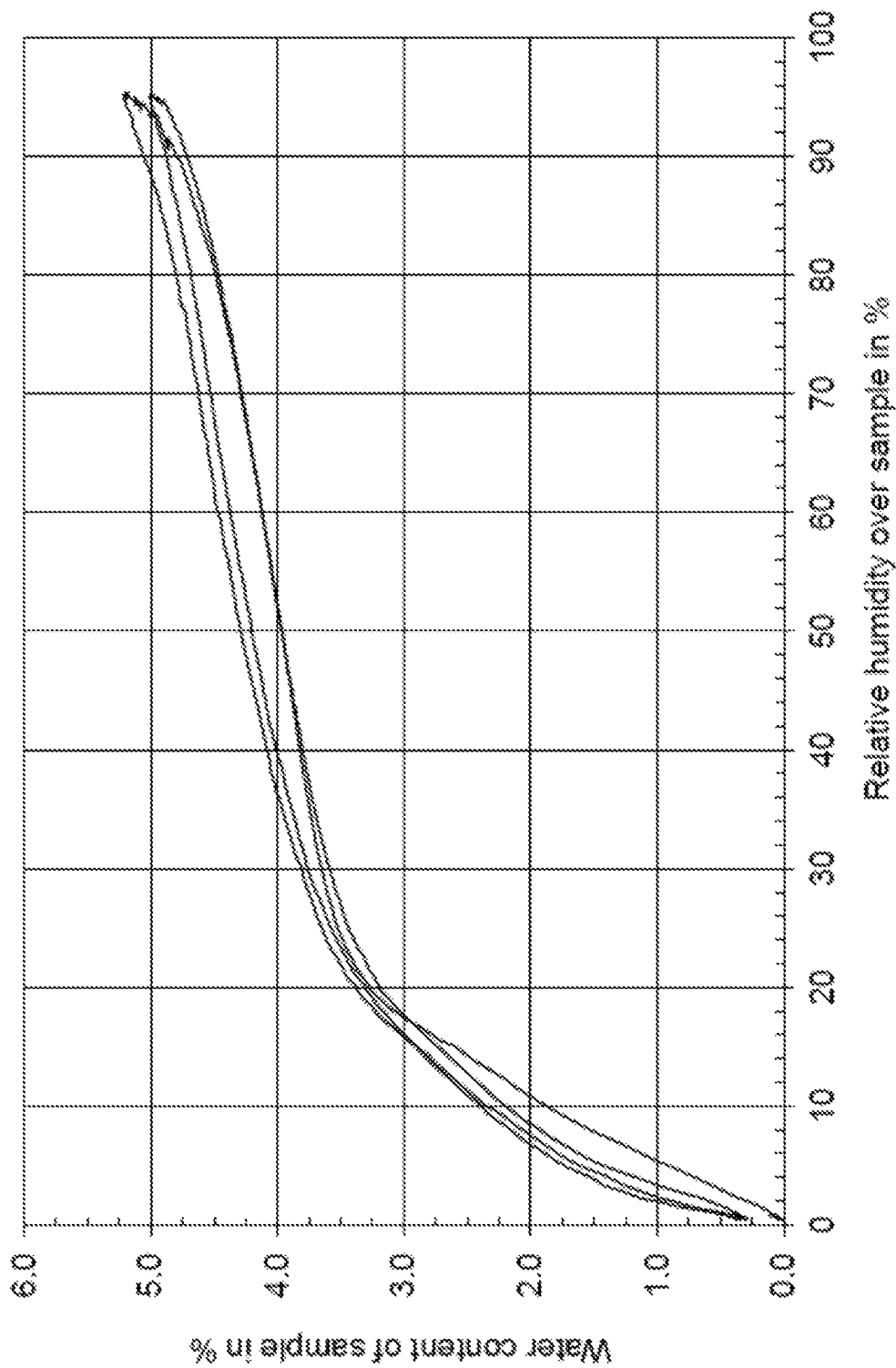
FIG. 15 shows the dynamic vapour sorption (DVS) mass change plot for crystal modification 1.

The water uptake of crystal modification 1 was measured using dynamic vapour sorption (DVS). The measurements demonstrate that the water content is reversibly dependent on the environmental humidity with maximum uptakes of about 5.0% (w/w) at 95% RH, as shown in FIG. 15.

After drying the sample at 0% RH and increasing the relative humidity, most of the water was taken back up to about 25% RH. This corresponds to a water content of about 3.5% (w/w). An additional 1.5% (w/w) of water was then taken up when the humidity was increased up to 95% RH. The sorption/desorption process shows minimal hysteresis. XRPD analysis has shown that the hydrate structure is almost completely restored at 20% RH and is completely restored at 30% RH. Crystal modification 1 therefore seems to require about 3.5% (w/w) of water, which corresponds to a sesquihydrate. The further water uptake at higher relative humidities does not change the structure any further. Crystal modification 1 is therefore likely a slightly hygroscopic sesquihydrate that can take up additional 1.5% (w/w) of water at elevated relative humidity in the range of 30-95% RH.

Example 11

Stability Testing

Samples of amorphous odevixibat (purity ~91%) and of crystal modification 1 of odevixibat (purity >99%; crystallinity 100%) were stored in a closed container under air at 80° C. The amount of odevixibat in the samples was determined by HPLC at the beginning of the experiment, and was again determined after 1, 2 and 4 weeks. The results are shown in the table below. After 4 weeks of storage, the amorphous sample showed 0.3% decomposition, whereas the purity of the crystalline sample had not changed.

| Time (weeks) | Odevixibat content (%) | |
| --- | --- | --- |
| | Amorphous odevixibat | crystal modification 1 |
| 0 | 91.1 | 99.13 |
| 1 | 90.9 | 99.15 |
| 2 | 91.04 | 99.18 |
| 4 | 90.8 | 99.24 |

Example 12

Determination of Crystalline Fraction by Differential Scanning Calorimetry

This method quantifies the crystalline fraction of odevixibat drug substance in partially crystalline samples. The quantification is based on the assumption that partially crystalline samples are binary mixtures of the crystalline hydrate and the amorphous phase of odevixibat. The crystalline fraction is quantified based on the melting enthalpy of an anhydrous form. This anhydrous form is the dehydrated hydrate which spontaneously and reproducibly forms by drying the hydrate at elevated temperature.

5-6 mg of a sample of a crystalline or partially crystalline sample of odevixibat was accurately weighed into a DSC crucible which was then closed with a perforated lid using a suitable press. The total weight of the DSC crucible (pan+lid+sample) was noted and the total weight of the crucible was again determined after the DSC test. The weight loss during the DSC test must not be more than 5%.

The DSC test consists of three cycles:
Cycle 1: an increase in temperature from 20° C. to 120° C. at a scanning rate of 5° C./min;
Cycle 2: a decrease in temperature from 120° C. to 80° C. at a scanning rate of 10° C./min; and
Cycle 3: an increase in temperature from 80° C. to 200° C. at a scanning rate of 10° C./min.

Figure 16:
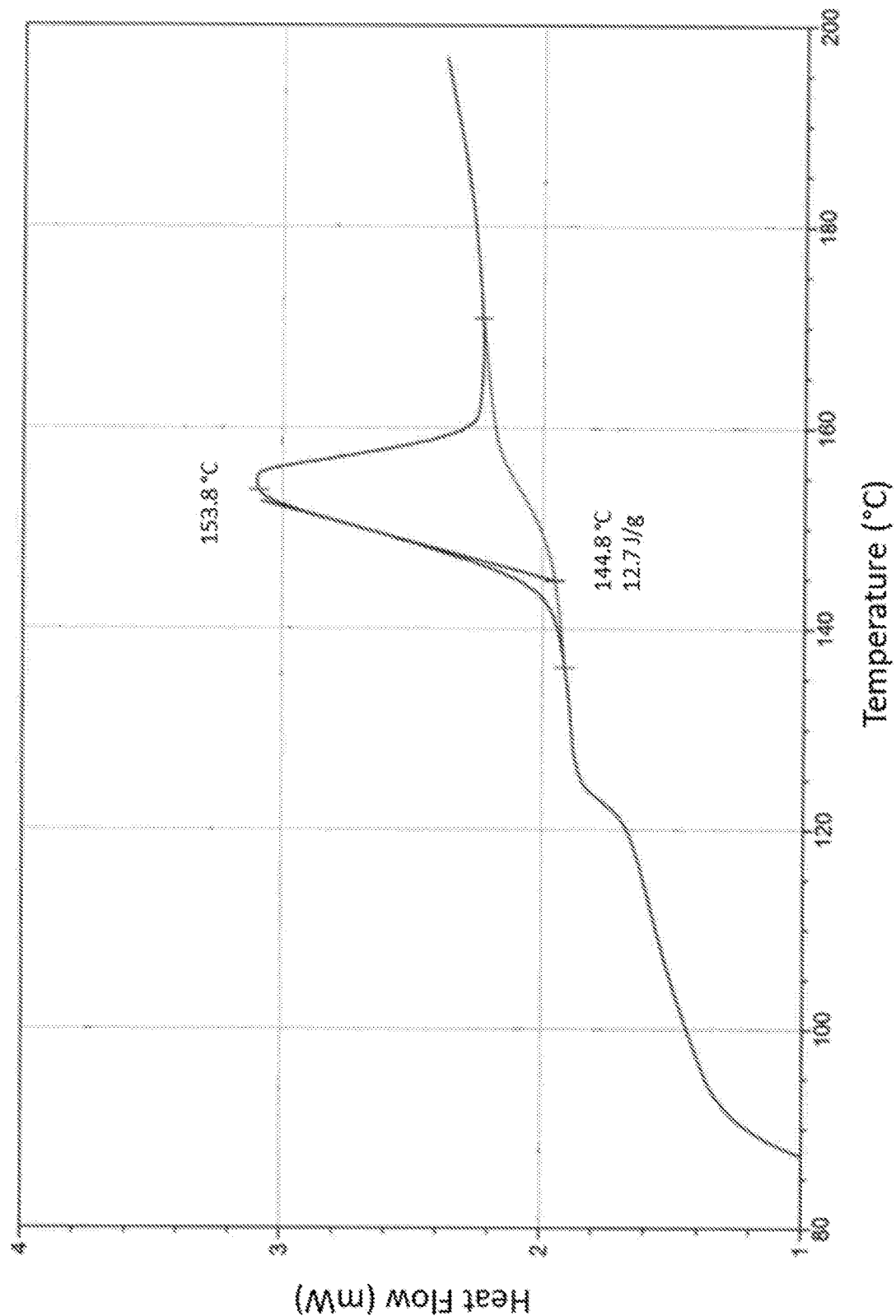
FIG. 16 shows the DSC trace of a sample of odevixibat with about 50% crystalline fraction (after pre-heating and cooling).

The first scan cycle dries the sample and thereby converts the hydrate form into a dehydrated hydrate (an anhydrous form). In the second scan cycle, the sample is cooled down to obtain a stable baseline in the subsequent heat-up for signal integration. The melting enthalpy is determined in the third scan cycle, where the sample is heated through the melting of the anhydrous form. The endothermic event due to melting appears in the temperature range of 140-165° C. The peak must be integrated over a sigmoidal tangent baseline using the Sig Tangent integration function of the TA Universal Analysis software. The integration should start at a temperature between 130° C. and 140° C., and end at a temperature between 165° C. and 175° C., depending on the actual baseline. The glass transition of the amorphous part may appear in the temperature range of 120-130° C., depending on the actual amorphous fraction (see FIG. 16 for an example). If an irregular baseline does not allow the integration, it should be assessed whether the drying of the sample was incomplete.

The evaluation of the melting enthalpy is done by using the dry weight of the sample, which is obtained by subtracting the total weight of the DSC crucible (pan+lid+sample) after the DSC test from the total weight of the crucible before the test. The percent weight loss during the DSC scan, which is the difference between the initial weight and the dry weight divided by the initial weight, must not be more than 5%; otherwise the crystalline content of the sample cannot be calculated. The crystalline fraction expressed in weight percent is to be calculated from the melting enthalpy ($\Delta H_{sample}$) based on the following formula. The value shall be given on an integer number.

$$\% \text{ crystalline content} = \frac{\Delta H_{sample} + 1.1626}{0.2815}$$

Example 13

Effect of Drying on the Crystallinity of Crystal Modification 1

In these experiments, crystal modification 2 was obtained after slurring of crystal modification 1 in a 6:4 mixture of ethanol/water; the obtained wet material was thereafter stored in a desiccator under ethanol/water (6:4) vapor for two months.

Samples of crystal modification 2 were then dried using different drying techniques, in order to see the impact of drying on the crystallinity of crystal modification 1. The dried samples were analyzed using XRPD (samples were prepared in an ambient air atmosphere) and the results are shown in the table below. The results suggest that crystal modification 1 is obtained by rehydration of the dehydrated form, which is obtained by drying of crystal modification 2 under vacuum or under nitrogen flow. When crystal modification 2 is stored at ambient conditions, the ethanol-water exchange seems to be very low.

| Drying conditions | Results |
|---|---|
| Vacuum (<5 mbar), room temperature. | Crystal modification 1 |
| Nitrogen flow, room temperature | Crystal modification 1 |
| Ambient conditions | Poorly crystalline crystal modification 1 |

Example 14

Effect of Solvent on Crystallinity of Crystal Modification 2

Crystal modification 1 was suspended in a 30:70 (% v/v) mixture of ethanol and water (sample A) or in a 70:30 (% v/v) mixture of ethanol and water (sample B) at room temperature. After stirring overnight, filtration was conducted and the recovered wet samples were submitted for XRPD (transmission). The XRPD patterns for both samples essentially corresponded to crystal modification 2, but some slight peak shifts were observed between the two samples, possibly due to the difference in ethanol content of the two samples.

Both samples were then subjected to air drying at room temperature and retested by XRPD. In both cases, crystal modification 1 was obtained, but based on the peak resolution in the XRPD patterns the sample obtained from the 70:30 (% v/v) mixture of ethanol and water appeared considerably more crystalline.

DSC measurements were conducted on the air-dried samples. It was found that sample A, obtained from the mixture containing 30% ethanol, was less crystalline than sample B, obtained from the mixture containing 70% ethanol. An enthalpy of fusion of 25.7 J/g was found for sample A which corresponds to 95% of crystallinity. For sample B, an enthalpy of 28.9 J/g was found, which corresponds to more than 100% crystallinity.

The invention claimed is:

1. A crystalline hydrate of odevixibat.

2. The hydrate according to claim 1, which is a channel hydrate.

3. The hydrate according to claim 1, which comprises from about 0 to about 2 moles of water associated with the crystal per mole of odevixibat.

4. The hydrate according to claim 1, which is a sesquihydrate.

5. The hydrate according to claim 1, having an XRPD pattern, obtained with CuKα1-radiation, with peaks at °2θ positions 5.6±0.2, 6.7±0.2 and/or 12.1±0.2.

6. The hydrate according to claim 5, having an XRPD pattern, obtained with CuKα1-radiation, with specific peaks at °2θ positions 5.6±0.2, 6.7±0.2 and 12.1±0.2 and one or more of the characteristic peaks: 4.1±0.2, 4.6±0.2, 9.3±0.2, 9.4±0.2 and 10.7±0.2.

7. The hydrate according to claim 5, having a crystallinity of greater than about 99%.

8. A mixed solvate of odevixibat, containing about two moles of water per mole of odevixibat.

9. The mixed solvate according to claim 8, wherein the organic solvent is methanol, ethanol, 2-propanol, acetone, acetonitrile, 1,4-dioxane, DMF or DMSO.

10. The mixed solvate according to claim 8, wherein the organic solvent is ethanol.

11. The mixed solvate according to claim 8, having an XRPD pattern, obtained with CuKα1-radiation, with peaks at °2θ positions 5.0±0.2, 5.1±0.2 and/or 11.8±0.2.

12. The mixed solvate according to claim 11, having an XRPD pattern, obtained with CuKα1-radiation, with peaks at °2θ positions 5.0±0.2, 5.1±0.2, 6.4±0.2, 6.6±0.2, 9.5±0.2 and 11.8±0.2.

13. The mixed solvate according to claim 8, having an XRPD pattern, obtained with CuKα1-radiation, with peaks at °2θ positions 4.8±0.2, 5.1±0.2 and/or 11.6±0.2.

14. The mixed solvate according to claim 13, having an XRPD pattern, obtained with CuKα1-radiation, with peaks at °2θ positions 4.8±0.2, 5.1±0.2, 6.2±0.2, 6.67±0.2, 9.5±0.2, 11.6±0.2 and 20.3±0.

15. The mixed solvate according to claim 8, having an XRPD pattern, obtained with CuKα1-radiation, with peaks at °2θ positions 5.0±0.2, 6.2±0.2, 9.4±0.2 and/or 23.9±0.2.

16. The mixed solvate according to claim 15, having an XRPD pattern, obtained with CuKα1-radiation, with peaks at °2θ positions 5.0±0.2, 6.2±0.2, 9.4±0.2 and 23.9±0.2 and one or more of the characteristic peaks: 11.5±0.2, 19.5±0.2 and 20.2±0.2.

17. A process for the preparation of crystal modification 1 of odevixibat, comprising isolating crystal modification 2 of odevixibat from a solution of odevixibat in a solvent mixture comprising water and an organic solvent selected from the group consisting of methanol, ethanol, 2-propanol, acetone, acetonitrile, 1,4-dioxane, DMF and DMSO.

18. The process according to claim 17, wherein the crystal modification 2 of odevixibat is crystal modification 2A of odevixibat.

19. The process according to claim 17, wherein crystal modification 2A of odevixibat is obtained from a mixture of water and ethanol.

20. The process according to claim 19, wherein the ethanol content in the solvent mixture is about 55 to about 75% (v/v).

* * * * *

UNITED STATES PATENT AND TRADEMARK OFFICE
CERTIFICATE OF CORRECTION

PATENT NO. : 10,975,046 B2
APPLICATION NO. : 16/508036
DATED : April 13, 2021
INVENTOR(S) : Robert Lundqvist et al.

It is certified that error appears in the above-identified patent and that said Letters Patent is hereby corrected as shown below:

On the Title Page

Item (56), Column 2, Line 7, under "OTHER PUBLICATIONS," delete "Alagile" and insert -- Alagille --.

Signed and Sealed this
Twenty-ninth Day of August, 2023

Katherine Kelly Vidal
*Director of the United States Patent and Trademark Office*

SEQUENCE LISTING

<160> NUMBER OF SEQ ID NOS: 4

<210> SEQ ID NO 1
<211> LENGTH: 1251

```
<212> TYPE: PRT
<213> ORGANISM: Homo sapiens

<400> SEQUENCE: 1

Met Ser Thr Glu Arg Asp Ser Glu Thr Thr Phe Asp Glu Asp Ser Gln
1               5                   10                  15

Pro Asn Asp Glu Val Val Pro Tyr Ser Asp Glu Thr Glu Asp Glu
            20                  25                  30

Leu Asp Asp Gln Gly Ser Ala Val Glu Pro Glu Gln Asn Arg Val Asn
        35                  40                  45

Arg Glu Ala Glu Glu Asn Arg Glu Pro Phe Arg Lys Glu Cys Thr Trp
    50                  55                  60

Gln Val Lys Ala Asn Asp Arg Lys Tyr His Glu Gln Pro His Phe Met
65                  70                  75                  80

Asn Thr Lys Phe Leu Cys Ile Lys Glu Ser Lys Tyr Ala Asn Asn Ala
                85                  90                  95

Ile Lys Thr Tyr Lys Tyr Asn Ala Phe Thr Phe Ile Pro Met Asn Leu
            100                 105                 110

Phe Glu Gln Phe Lys Arg Ala Ala Asn Leu Tyr Phe Leu Ala Leu Leu
        115                 120                 125

Ile Leu Gln Ala Val Pro Gln Ile Ser Thr Leu Ala Trp Tyr Thr Thr
130                 135                 140

Leu Val Pro Leu Leu Val Val Leu Gly Val Thr Ala Ile Lys Asp Leu
145                 150                 155                 160

Val Asp Asp Val Ala Arg His Lys Met Asp Lys Glu Ile Asn Asn Arg
                165                 170                 175

Thr Cys Glu Val Ile Lys Asp Gly Arg Phe Lys Val Ala Lys Trp Lys
            180                 185                 190

Glu Ile Gln Val Gly Asp Val Ile Arg Leu Lys Lys Asn Asp Phe Val
        195                 200                 205

Pro Ala Asp Ile Leu Leu Leu Ser Ser Ser Glu Pro Asn Ser Leu Cys
210                 215                 220

Tyr Val Glu Thr Ala Glu Leu Asp Gly Glu Thr Asn Leu Lys Phe Lys
225                 230                 235                 240

Met Ser Leu Glu Ile Thr Asp Gln Tyr Leu Gln Arg Glu Asp Thr Leu
                245                 250                 255

Ala Thr Phe Asp Gly Phe Ile Glu Cys Glu Glu Pro Asn Asn Arg Leu
            260                 265                 270

Asp Lys Phe Thr Gly Thr Leu Phe Trp Arg Asn Thr Ser Phe Pro Leu
        275                 280                 285

Asp Ala Asp Lys Ile Leu Leu Arg Gly Cys Val Ile Arg Asn Thr Asp
290                 295                 300

Phe Cys His Gly Leu Val Ile Phe Ala Gly Ala Asp Thr Lys Ile Met
305                 310                 315                 320

Lys Asn Ser Gly Lys Thr Arg Phe Lys Arg Thr Lys Ile Asp Tyr Leu
                325                 330                 335

Met Asn Tyr Met Val Tyr Thr Ile Phe Val Val Leu Ile Leu Leu Ser
            340                 345                 350

Ala Gly Leu Ala Ile Gly His Ala Tyr Trp Glu Ala Gln Val Gly Asn
        355                 360                 365

Ser Ser Trp Tyr Leu Tyr Asp Gly Glu Asp Asp Thr Pro Ser Tyr Arg
370                 375                 380

Gly Phe Leu Ile Phe Trp Gly Tyr Ile Ile Val Leu Asn Thr Met Val
385                 390                 395                 400
```

-continued

Pro Ile Ser Leu Tyr Val Ser Val Glu Val Ile Arg Leu Gly Gln Ser
                405                 410                 415

His Phe Ile Asn Trp Asp Leu Gln Met Tyr Tyr Ala Glu Lys Asp Thr
                420                 425                 430

Pro Ala Lys Ala Arg Thr Thr Thr Leu Asn Glu Gln Leu Gly Gln Ile
                435                 440                 445

His Tyr Ile Phe Ser Asp Lys Thr Gly Thr Leu Thr Gln Asn Ile Met
450                 455                 460

Thr Phe Lys Lys Cys Cys Ile Asn Gly Gln Ile Tyr Gly Asp His Arg
465                 470                 475                 480

Asp Ala Ser Gln His Asn His Asn Lys Ile Glu Gln Val Asp Phe Ser
                485                 490                 495

Trp Asn Thr Tyr Ala Asp Gly Lys Leu Ala Phe Tyr Asp His Tyr Leu
                500                 505                 510

Ile Glu Gln Ile Gln Ser Gly Lys Glu Pro Glu Val Arg Gln Phe Phe
                515                 520                 525

Phe Leu Leu Ala Val Cys His Thr Val Met Val Asp Arg Thr Asp Gly
                530                 535                 540

Gln Leu Asn Tyr Gln Ala Ala Ser Pro Asp Glu Gly Ala Leu Val Asn
545                 550                 555                 560

Ala Ala Arg Asn Phe Gly Phe Ala Phe Leu Ala Arg Thr Gln Asn Thr
                565                 570                 575

Ile Thr Ile Ser Glu Leu Gly Thr Glu Arg Thr Tyr Asn Val Leu Ala
                580                 585                 590

Ile Leu Asp Phe Asn Ser Asp Arg Lys Arg Met Ser Ile Ile Val Arg
                595                 600                 605

Thr Pro Glu Gly Asn Ile Lys Leu Tyr Cys Lys Gly Ala Asp Thr Val
610                 615                 620

Ile Tyr Glu Arg Leu His Arg Met Asn Pro Thr Lys Gln Glu Thr Gln
625                 630                 635                 640

Asp Ala Leu Asp Ile Phe Ala Asn Glu Thr Leu Arg Thr Leu Cys Leu
                645                 650                 655

Cys Tyr Lys Glu Ile Glu Glu Lys Glu Phe Thr Glu Trp Asn Lys Lys
                660                 665                 670

Phe Met Ala Ala Ser Val Ala Ser Thr Asn Arg Asp Glu Ala Leu Asp
                675                 680                 685

Lys Val Tyr Glu Glu Ile Glu Lys Asp Leu Ile Leu Leu Gly Ala Thr
                690                 695                 700

Ala Ile Glu Asp Lys Leu Gln Asp Gly Val Pro Glu Thr Ile Ser Lys
705                 710                 715                 720

Leu Ala Lys Ala Asp Ile Lys Ile Trp Val Leu Thr Gly Asp Lys Lys
                725                 730                 735

Glu Thr Ala Glu Asn Ile Gly Phe Ala Cys Glu Leu Leu Thr Glu Asp
                740                 745                 750

Thr Thr Ile Cys Tyr Gly Glu Asp Ile Asn Ser Leu Leu His Ala Arg
                755                 760                 765

Met Glu Asn Gln Arg Asn Arg Gly Gly Val Tyr Ala Lys Phe Ala Pro
                770                 775                 780

Pro Val Gln Glu Ser Phe Phe Pro Gly Gly Asn Arg Ala Leu Ile
785                 790                 795                 800

Ile Thr Gly Ser Trp Leu Asn Glu Ile Leu Leu Glu Lys Lys Thr Lys
                805                 810                 815

```
Arg Asn Lys Ile Leu Lys Leu Lys Phe Pro Arg Thr Glu Glu Arg
            820                 825                 830

Arg Met Arg Thr Gln Ser Lys Arg Arg Leu Glu Ala Lys Lys Glu Gln
            835                 840                 845

Arg Gln Lys Asn Phe Val Asp Leu Ala Cys Glu Cys Ser Ala Val Ile
            850                 855                 860

Cys Cys Arg Val Thr Pro Lys Gln Lys Ala Met Val Val Asp Leu Val
865                 870                 875                 880

Lys Arg Tyr Lys Lys Ala Ile Thr Leu Ala Ile Gly Asp Gly Ala Asn
                885                 890                 895

Asp Val Asn Met Ile Lys Thr Ala His Ile Gly Val Gly Ile Ser Gly
            900                 905                 910

Gln Glu Gly Met Gln Ala Val Met Ser Ser Asp Tyr Ser Phe Ala Gln
            915                 920                 925

Phe Arg Tyr Leu Gln Arg Leu Leu Leu Val His Gly Arg Trp Ser Tyr
            930                 935                 940

Ile Arg Met Cys Lys Phe Leu Arg Tyr Phe Phe Tyr Lys Asn Phe Ala
945                 950                 955                 960

Phe Thr Leu Val His Phe Trp Tyr Ser Phe Asn Gly Tyr Ser Ala
            965                 970                 975

Gln Thr Ala Tyr Glu Asp Trp Phe Ile Thr Leu Tyr Asn Val Leu Tyr
            980                 985                 990

Thr Ser Leu Pro Val Leu Leu Met  Gly Leu Leu Asp Gln Asp Val Ser
        995                 1000                1005

Asp Lys Leu Ser Leu Arg Phe  Pro Gly Leu Tyr Ile  Val Gly Gln
    1010                1015                1020

Arg Asp Leu Leu Phe Asn Tyr  Lys Arg Phe Phe Val  Ser Leu Leu
    1025                1030                1035

His Gly Val Leu Thr Ser Met  Ile Leu Phe Phe Ile  Pro Leu Gly
    1040                1045                1050

Ala Tyr Leu Gln Thr Val Gly  Gln Asp Gly Glu Ala  Pro Ser Asp
    1055                1060                1065

Tyr Gln Ser Phe Ala Val Thr  Ile Ala Ser Ala Leu  Val Ile Thr
    1070                1075                1080

Val Asn Phe Gln Ile Gly Leu  Asp Thr Ser Tyr Trp  Thr Phe Val
    1085                1090                1095

Asn Ala Phe Ser Ile Phe Gly  Ser Ile Ala Leu Tyr  Phe Gly Ile
    1100                1105                1110

Met Phe Asp Phe His Ser Ala  Gly Ile His Val Leu  Phe Pro Ser
    1115                1120                1125

Ala Phe Gln Phe Thr Gly Thr  Ala Ser Asn Ala Leu  Arg Gln Pro
    1130                1135                1140

Tyr Ile Trp Leu Thr Ile Ile  Leu Ala Val Ala Val  Cys Leu Leu
    1145                1150                1155

Pro Val Val Ala Ile Arg Phe  Leu Ser Met Thr Ile  Trp Pro Ser
    1160                1165                1170

Glu Ser Asp Lys Ile Gln Lys  His Arg Lys Arg Leu  Lys Ala Glu
    1175                1180                1185

Glu Gln Trp Gln Arg Arg Gln  Gln Val Phe Arg Arg  Gly Val Ser
    1190                1195                1200

Thr Arg Arg Ser Ala Tyr Ala  Phe Ser His Gln Arg  Gly Tyr Ala
    1205                1210                1215

Asp Leu Ile Ser Ser Gly Arg  Ser Ile Arg Lys Lys  Arg Ser Pro
```

| | | | |
|---|---|---|---|
| | 1220 | 1225 | 1230 |

Leu Asp Ala Ile Val Ala Asp Gly Thr Ala Glu Tyr Arg Arg Thr
　　　1235　　　　　　1240　　　　　　1245

Gly Asp Ser
　　1250

<210> SEQ ID NO 2
<211> LENGTH: 3756
<212> TYPE: DNA
<213> ORGANISM: Homo sapiens

<400> SEQUENCE: 2

| | | | | | |
|---|---|---|---|---|---|
| atgagtacag | aaagagactc | agaaacgaca | tttgacgagg | attctcagcc | taatgacgaa | 60 |
| gtggttccct | acagtgatga | tgaaacagaa | gatgaacttg | atgaccaggg | gtctgctgtt | 120 |
| gaaccagaac | aaaaccgagt | caacagggaa | gcagaggaga | accggagcc | attcagaaaa | 180 |
| gaatgtacat | ggcaagtcaa | agcaaacgat | cgcaagtacc | acgaacaacc | tcactttatg | 240 |
| aacacaaaat | tcttgtgtat | taaggagagt | aaatatgcga | taatgcaat | taaaacatac | 300 |
| aagtacaacg | catttacctt | tataccaatg | aatctgtttg | agcagtttaa | gagagcagcc | 360 |
| aatttatatt | tcctggctct | tcttatctta | caggcagttc | ctcaaatctc | taccctggct | 420 |
| tggtacacca | cactagtgcc | cctgcttgtg | gtgctgggcg | tcactgcaat | caaagacctg | 480 |
| gtggacgatg | tggctcgcca | taaatggat | aaggaaatca | acaataggac | gtgtgaagtc | 540 |
| attaaggatg | gcaggttcaa | agttgctaag | tggaaagaaa | ttcaagttgg | agacgtcatt | 600 |
| cgtctgaaaa | aaatgatttt | tgttccagct | gacattctcc | tgctgtctag | ctctgagcct | 660 |
| aacagcctct | gctatgtgga | aacagcagaa | ctggatggag | aaaccaattt | aaaatttaag | 720 |
| atgtcacttg | aaatcacaga | ccagtacctc | caaagagaag | atacattggc | tacatttgat | 780 |
| ggttttattg | aatgtgaaga | acccaataac | agactagata | agtttacagg | aacactattt | 840 |
| tggagaaaca | caagttttcc | tttggatgct | gataaaattt | tgttacgtgg | ctgtgtaatt | 900 |
| aggaacaccg | atttctgcca | cggcttagtc | atttttgcag | gtgctgacac | taaaataatg | 960 |
| aagaatagtg | gaaaaccag | atttaaaaga | actaaaattg | attacttgat | gaactacatg | 1020 |
| gtttacacga | tctttgttgt | tcttattctg | ctttctgctg | gtcttgccat | cggccatgct | 1080 |
| tattgggaag | cacaggtggg | caattcctct | tggtacctct | atgatggaga | agacgataca | 1140 |
| ccctcctacc | gtggattcct | catttttctgg | ggctatatca | ttgttctcaa | caccatggta | 1200 |
| cccatctctc | tctatgtcag | cgtggaagtg | attcgtcttg | gacagagtca | cttcatcaac | 1260 |
| tgggaccdtgc | aaatgtacta | tgctgagaag | gacacacccg | caaaagctag | aaccaccaca | 1320 |
| ctcaatgaac | agctcgggca | gatccattat | atcttctctg | ataagacggg | gacactcaca | 1380 |
| caaaatatca | tgacctttaa | aaagtgctgt | atcaacgggc | agatatatgg | ggaccatcgg | 1440 |
| gatgcctctc | aacacaacca | caaaatata | gagcaagttg | attttagctg | gaatacatat | 1500 |
| gctgatggga | agcttgcatt | ttatgaccac | tatcttattg | agcaaatcca | gtcagggaaa | 1560 |
| gagccagaag | tacgacagtt | cttcttcttg | ctcgcagttt | gccacacagt | catggtggat | 1620 |
| aggactgatg | tcagctcaa | ctaccaggca | gcctctcccg | atgaaggtgc | cctggtaaac | 1680 |
| gctgccagga | actttggctt | tgccttcctc | gccaggaccc | agaacaccat | caccatcagt | 1740 |
| gaactgggca | ctgaaaggac | ttacaatgtt | cttgccattt | tggacttcaa | cagtgaccgg | 1800 |
| aagcgaatgt | ctatcattgt | aagaaccccca | gaaggcaata | tcaagcttta | ctgtaaaggt | 1860 |
| gctgacactg | ttatttatga | acggttacat | cgaatgaatc | ctactaagca | agaaacacag | 1920 |

-continued

```
gatgccctgg atatctttgc aaatgaaact cttagaaccc tatgcctttg ctacaaggaa    1980
attgaagaaa aagaatttac agaatggaat aaaaagttta tggctgccag tgtggcctcc    2040
accaaccggg acgaagctct ggataaagta tatgaggaga ttgaaaaaga cttaattctc    2100
ctgggagcta cagctattga agacaagcta caggatggat tccagaaaac catttcaaaa    2160
cttgcaaaag ctgacattaa gatctgggtg cttactggag acaaaaagga aactgctgaa    2220
aatataggat ttgcttgtga acttctgact gaagacacca ccatctgcta tggggaggat    2280
attaattctc ttcttcatgc aaggatggaa aaccagagga atagaggtgg cgtctacgca    2340
aagtttgcac ctcctgtgca ggaatctttt tttccacccg gtgaaaaccg tgccttaatc    2400
atcactggtt cttggttgaa tgaaattctt ctcgagaaaa agaccaagag aaataagatt    2460
ctgaagctga agttcccaag aacagaagaa gaaagacgga tgcggaccca agtaaaagg    2520 aggctagaag ctaagaaaga gcagcggcag aaaaactttg tggacctggc ctgcgagtgc    2580
agcgcagtca tctgctgccg cgtcaccccc aagcagaagg ccatggtggt ggacctggtg    2640
aagaggtaca agaaagccat cacgctggcc atcggagatg gggccaatga cgtgaacatg    2700
atcaaaactg cccacattgg cgttggaata agtggacaag aaggaatgca agctgtcatg    2760
tcgagtgact attcctttgc tcagttccga tatctgcaga ggctactgct ggtgcatggc    2820
cgatggtctt acataaggat gtgcaagttc ctacgatact tcttttacaa aaactttgcc    2880
tttactttgg ttcatttctg gtactccttc ttcaatggct actctgcgca gactgcatac    2940
gaggattggt tcatcaccct ctacaacgtg ctgtacacca gcctgcccgt gctcctcatg    3000
gggctgctcg accaggatgt gagtgacaaa ctgagcctcc gattccctgg gttatacata    3060
gtgggacaaa gagacttact attcaactat aagagattct ttgtaagctt gttgcatggg    3120
gtcctaacat cgatgatcct cttcttcata cctcttggag cttatctgca aaccgtaggg    3180
caggatggag aggcaccttc cgactaccag tcttttgccg tcaccattgc ctctgctctt    3240
gtaataacag tcaatttcca gattggcttg gatacttctt attggacttt tgtgaatgct    3300
ttttcaattt ttggaagcat tgcactttat tttggcatca tgtttgactt tcatagtgct    3360
ggaatacatg ttctctttcc atctgcattt caatttacag gcacagcttc aaacgctctg    3420
agacagccat acatttggtt aactatcatc ctggctgttg ctgtgtgctt actacccgtc    3480
gttgccattc gattcctgtc aatgaccatc tggccatcag aaagtgataa gatccagaag    3540
catcgcaagc ggttgaaggc ggaggagcag tggcagcgac ggcagcaggt gttccgccgg    3600
ggcgtgtcaa cgcggcgctc ggcctacgcc ttctcgcacc agcggggcta cgcggacctc    3660
atctcctccg ggcgcagcat ccgcaagaag cgctcgccgc ttgatgccat cgtggcggat    3720
ggcaccgcgg agtacaggcg caccggggac agctga                              3756
```

<210> SEQ ID NO 3
<211> LENGTH: 1321
<212> TYPE: PRT
<213> ORGANISM: Homo sapiens

<400> SEQUENCE: 3

```
Met Ser Asp Ser Val Ile Leu Arg Ser Ile Lys Lys Phe Gly Glu Glu
1               5                   10                  15

Asn Asp Gly Phe Glu Ser Asp Lys Ser Tyr Asn Asn Asp Lys Lys Ser
            20                  25                  30

Arg Leu Gln Asp Glu Lys Lys Gly Asp Gly Val Arg Val Gly Phe Phe
        35                  40                  45
```

```
Gln Leu Phe Arg Phe Ser Ser Thr Asp Ile Trp Leu Met Phe Val
    50                  55                  60
Gly Ser Leu Cys Ala Phe Leu His Gly Ile Ala Gln Pro Gly Val Leu
 65                  70                  75                  80
Leu Ile Phe Gly Thr Met Thr Asp Val Phe Ile Asp Tyr Asp Val Glu
                     85                  90                  95
Leu Gln Glu Leu Gln Ile Pro Gly Lys Ala Cys Val Asn Asn Thr Ile
                100                 105                 110
Val Trp Thr Asn Ser Ser Leu Asn Gln Asn Met Thr Asn Gly Thr Arg
            115                 120                 125
Cys Gly Leu Leu Asn Ile Glu Ser Glu Met Ile Lys Phe Ala Ser Tyr
130                 135                 140
Tyr Ala Gly Ile Ala Val Ala Val Leu Ile Thr Gly Tyr Ile Gln Ile
145                 150                 155                 160
Cys Phe Trp Val Ile Ala Ala Arg Gln Ile Gln Lys Met Arg Lys
                165                 170                 175
Phe Tyr Phe Arg Arg Ile Met Arg Met Glu Ile Gly Trp Phe Asp Cys
                180                 185                 190
Asn Ser Val Gly Glu Leu Asn Thr Arg Phe Ser Asp Asp Ile Asn Lys
            195                 200                 205
Ile Asn Asp Ala Ile Ala Asp Gln Met Ala Leu Phe Ile Gln Arg Met
210                 215                 220
Thr Ser Thr Ile Cys Gly Phe Leu Leu Gly Phe Phe Arg Gly Trp Lys
225                 230                 235                 240
Leu Thr Leu Val Ile Ile Ser Val Ser Pro Leu Ile Gly Ile Gly Ala
                245                 250                 255
Ala Thr Ile Gly Leu Ser Val Ser Lys Phe Thr Asp Tyr Glu Leu Lys
                260                 265                 270
Ala Tyr Ala Lys Ala Gly Val Val Ala Asp Glu Val Ile Ser Ser Met
                275                 280                 285
Arg Thr Val Ala Ala Phe Gly Gly Glu Lys Arg Glu Val Glu Arg Tyr
            290                 295                 300
Glu Lys Asn Leu Val Phe Ala Gln Arg Trp Gly Ile Arg Lys Gly Ile
305                 310                 315                 320
Val Met Gly Phe Phe Thr Gly Phe Val Trp Cys Leu Ile Phe Leu Cys
                325                 330                 335
Tyr Ala Leu Ala Phe Trp Tyr Gly Ser Thr Leu Val Leu Asp Glu Gly
                340                 345                 350
Glu Tyr Thr Pro Gly Thr Leu Val Gln Ile Phe Leu Ser Val Ile Val
            355                 360                 365
Gly Ala Leu Asn Leu Gly Asn Ala Ser Pro Cys Leu Glu Ala Phe Ala
            370                 375                 380
Thr Gly Arg Ala Ala Ala Thr Ser Ile Phe Glu Thr Ile Asp Arg Lys
385                 390                 395                 400
Pro Ile Ile Asp Cys Met Ser Glu Asp Gly Tyr Lys Leu Asp Arg Ile
                405                 410                 415
Lys Gly Glu Ile Glu Phe His Asn Val Thr Phe His Tyr Pro Ser Arg
                420                 425                 430
Pro Glu Val Lys Ile Leu Asn Asp Leu Asn Met Val Ile Lys Pro Gly
            435                 440                 445
Glu Met Thr Ala Leu Val Gly Pro Ser Gly Ala Gly Lys Ser Thr Ala
            450                 455                 460
```

```
Leu Gln Leu Ile Gln Arg Phe Tyr Asp Pro Cys Glu Gly Met Val Thr
465                 470                 475                 480

Val Asp Gly His Asp Ile Arg Ser Leu Asn Ile Gln Trp Leu Arg Asp
            485                 490                 495

Gln Ile Gly Ile Val Glu Gln Glu Pro Val Leu Phe Ser Thr Thr Ile
            500                 505                 510

Ala Glu Asn Ile Arg Tyr Gly Arg Glu Asp Ala Thr Met Glu Asp Ile
        515                 520                 525

Val Gln Ala Ala Lys Glu Ala Asn Ala Tyr Asn Phe Ile Met Asp Leu
    530                 535                 540

Pro Gln Gln Phe Asp Thr Leu Val Gly Glu Gly Gly Gln Met Ser
545                 550                 555                 560

Gly Gly Gln Lys Gln Arg Val Ala Ile Ala Arg Ala Leu Ile Arg Asn
            565                 570                 575

Pro Lys Ile Leu Leu Leu Asp Met Ala Thr Ser Ala Leu Asp Asn Glu
            580                 585                 590

Ser Glu Ala Met Val Gln Glu Val Leu Ser Lys Ile Gln His Gly His
    595                 600                 605

Thr Ile Ile Ser Val Ala His Arg Leu Ser Thr Val Arg Ala Ala Asp
610                 615                 620

Thr Ile Ile Gly Phe Glu His Gly Thr Ala Val Glu Arg Gly Thr His
625                 630                 635                 640

Glu Glu Leu Leu Glu Arg Lys Gly Val Tyr Phe Thr Leu Val Thr Leu
                645                 650                 655

Gln Ser Gln Gly Asn Gln Ala Leu Asn Glu Glu Asp Ile Lys Asp Ala
            660                 665                 670

Thr Glu Asp Asp Met Leu Ala Arg Thr Phe Ser Arg Gly Ser Tyr Gln
        675                 680                 685

Asp Ser Leu Arg Ala Ser Ile Arg Gln Arg Ser Lys Ser Gln Leu Ser
    690                 695                 700

Tyr Leu Val His Glu Pro Pro Leu Ala Val Val Asp His Lys Ser Thr
705                 710                 715                 720

Tyr Glu Glu Asp Arg Lys Asp Lys Asp Ile Pro Val Gln Glu Glu Val
                725                 730                 735

Glu Pro Ala Pro Val Arg Arg Ile Leu Lys Phe Ser Ala Pro Glu Trp
            740                 745                 750

Pro Tyr Met Leu Val Gly Ser Val Gly Ala Ala Val Asn Gly Thr Val
        755                 760                 765

Thr Pro Leu Tyr Ala Phe Leu Phe Ser Gln Ile Leu Gly Thr Phe Ser
    770                 775                 780

Ile Pro Asp Lys Glu Glu Gln Arg Ser Gln Ile Asn Gly Val Cys Leu
785                 790                 795                 800

Leu Phe Val Ala Met Gly Cys Val Ser Leu Phe Thr Gln Phe Leu Gln
                805                 810                 815

Gly Tyr Ala Phe Ala Lys Ser Gly Glu Leu Leu Thr Lys Arg Leu Arg
            820                 825                 830

Lys Phe Gly Phe Arg Ala Met Leu Gly Gln Asp Ile Ala Trp Phe Asp
        835                 840                 845

Asp Leu Arg Asn Ser Pro Gly Ala Leu Thr Thr Arg Leu Ala Thr Asp
    850                 855                 860

Ala Ser Gln Val Gln Gly Ala Ala Gly Ser Gln Ile Gly Met Ile Val
865                 870                 875                 880

Asn Ser Phe Thr Asn Val Thr Val Ala Met Ile Ile Ala Phe Ser Phe
```

-continued

```
              885                 890                 895
Ser Trp Lys Leu Ser Leu Val Ile Leu Cys Phe Phe Pro Phe Leu Ala
            900                 905                 910
Leu Ser Gly Ala Thr Gln Thr Arg Met Leu Thr Gly Phe Ala Ser Arg
            915                 920                 925
Asp Lys Gln Ala Leu Glu Met Val Gly Gln Ile Thr Asn Glu Ala Leu
            930                 935                 940
Ser Asn Ile Arg Thr Val Ala Gly Ile Gly Lys Glu Arg Arg Phe Ile
945                 950                 955                 960
Glu Ala Leu Glu Thr Glu Leu Glu Lys Pro Phe Lys Thr Ala Ile Gln
            965                 970                 975
Lys Ala Asn Ile Tyr Gly Phe Cys Phe Ala Phe Ala Gln Cys Ile Met
            980                 985                 990
Phe Ile Ala Asn Ser Ala Ser Tyr Arg Tyr Gly Gly Tyr Leu Ile Ser
            995                1000                1005
Asn Glu Gly Leu His Phe Ser Tyr Val Phe Arg Val Ile Ser Ala
       1010                1015                1020
Val Val Leu Ser Ala Thr Ala Leu Gly Arg Ala Phe Ser Tyr Thr
       1025                1030                1035
Pro Ser Tyr Ala Lys Ala Lys Ile Ser Ala Ala Arg Phe Phe Gln
       1040                1045                1050
Leu Leu Asp Arg Gln Pro Pro Ile Ser Val Tyr Asn Thr Ala Gly
       1055                1060                1065
Glu Lys Trp Asp Asn Phe Gln Gly Lys Ile Asp Phe Val Asp Cys
       1070                1075                1080
Lys Phe Thr Tyr Pro Ser Arg Pro Asp Ser Gln Val Leu Asn Gly
       1085                1090                1095
Leu Ser Val Ser Ile Ser Pro Gly Gln Thr Leu Ala Phe Val Gly
       1100                1105                1110
Ser Ser Gly Cys Gly Lys Ser Thr Ser Ile Gln Leu Leu Glu Arg
       1115                1120                1125
Phe Tyr Asp Pro Asp Gln Gly Lys Val Met Ile Asp Gly His Asp
       1130                1135                1140
Ser Lys Lys Val Asn Val Gln Phe Leu Arg Ser Asn Ile Gly Ile
       1145                1150                1155
Val Ser Gln Glu Pro Val Leu Phe Ala Cys Ser Ile Met Asp Asn
       1160                1165                1170
Ile Lys Tyr Gly Asp Asn Thr Lys Glu Ile Pro Met Glu Arg Val
       1175                1180                1185
Ile Ala Ala Ala Lys Gln Ala Gln Leu His Asp Phe Val Met Ser
       1190                1195                1200
Leu Pro Glu Lys Tyr Glu Thr Asn Val Gly Ser Gln Gly Ser Gln
       1205                1210                1215
Leu Ser Arg Gly Glu Lys Gln Arg Ile Ala Ile Ala Arg Ala Ile
       1220                1225                1230
Val Arg Asp Pro Lys Ile Leu Leu Leu Asp Glu Ala Thr Ser Ala
       1235                1240                1245
Leu Asp Thr Glu Ser Glu Lys Thr Val Gln Val Ala Leu Asp Lys
       1250                1255                1260
Ala Arg Glu Gly Arg Thr Cys Ile Val Ile Ala His Arg Leu Ser
       1265                1270                1275
Thr Ile Gln Asn Ala Asp Ile Ile Ala Val Met Ala Gln Gly Val
       1280                1285                1290
```

| Val | Ile | Glu | Lys | Gly | Thr | His | Glu | Glu | Leu | Met | Ala | Gln | Lys | Gly |
| | 1295 | | | | 1300 | | | | 1305 | | | | | |

| Ala | Tyr | Tyr | Lys | Leu | Val | Thr | Thr | Gly | Ser | Pro | Ile | Ser |
| | 1310 | | | | 1315 | | | | 1320 | | | |

<210> SEQ ID NO 4
<211> LENGTH: 3966
<212> TYPE: DNA
<213> ORGANISM: Homo sapiens

<400> SEQUENCE: 4

| | | | | | |
|---|---|---|---|---|---|
| atgtctgact | cagtaattct | tcgaagtata | aagaaatttg | gagaggagaa | tgatggtttt | 60 |
| gagtcagata | aatcatataa | taatgataag | aaatcaaggt | tacaagatga | aagaaaggt | 120 |
| gatggcgtta | gagttggctt | ctttcaattg | tttcggtttt | cttcatcaac | tgacatttgg | 180 |
| ctgatgtttg | tgggaagttt | gtgtgcattt | ctccatggaa | tagcccagcc | aggcgtgcta | 240 |
| ctcattttg | gcacaatgac | agatgttttt | attgactacg | acgttgagtt | acaagaactc | 300 |
| cagattccag | gaaaagcatg | tgtgaataac | accattgtat | ggactaacag | ttccctcaac | 360 |
| cagaacatga | caaatggaac | acgttgtggg | ttgctgaaca | tcgagagcga | aatgatcaaa | 420 |
| tttgccagtt | actatgctgg | aattgctgtc | gcagtactta | tcacaggata | tattcaaata | 480 |
| tgcttttggg | tcattgccgc | agctcgtcag | atacagaaaa | tgagaaaatt | ttactttagg | 540 |
| agaataatga | gaatggaaat | agggtggttt | gactgcaatt | cagtggggga | gctgaataca | 600 |
| agattctctg | atgatattaa | taaaatcaat | gatgccatag | ctgaccaaat | ggcccttttc | 660 |
| attcagcgca | tgacctcgac | catctgtggt | ttcctgttgg | gattttttcag | gggttggaaa | 720 |
| ctgaccttgg | ttattatttc | tgtcagccct | ctcattggga | ttggagcagc | caccattggt | 780 |
| ctgagtgtgt | ccaagtttac | ggactatgag | ctgaaggcct | atgccaaagc | aggggtggtg | 840 |
| gctgatgaag | tcatttcatc | aatgagaaca | gtggctgctt | ttggtggtga | aaaagagag | 900 |
| gttgaaaggt | atgagaaaaa | tcttgtgttc | gcccagcgtt | ggggaattag | aaaaggaata | 960 |
| gtgatgggat | tctttactgg | attcgtgtgg | tgtctcatct | ttttgtgtta | tgcactggcc | 1020 |
| ttctggtacg | gctccacact | tgtcctggat | gaaggagaat | atacaccagg | aacccttgtc | 1080 |
| cagatttttcc | tcagtgtcat | agtaggagct | ttaaatcttg | gcaatgcctc | tccttgtttg | 1140 |
| gaagcctttg | caactggacg | tgcagcagcc | accagcattt | tgagacaat | agacaggaaa | 1200 |
| cccatcattg | actgcatgtc | agaagatggt | tacaagttgg | atcgaatcaa | gggtgaaatt | 1260 |
| gaattccata | atgtgaccctt | ccattatcct | tccagaccag | aggtgaagat | tctaaatgac | 1320 |
| ctcaacatgg | tcattaaacc | aggggaaatg | acagctctgg | taggacccag | tggagctgga | 1380 |
| aaaagtacag | cactgcaact | cattcagcga | ttctatgacc | cctgtgaagg | aatggtgacc | 1440 |
| gtggatggcc | atgacattcg | ctctcttaac | attcagtggc | ttagagatca | gattgggata | 1500 |
| gtggagcaag | agccagttct | gttctctacc | accattgcag | aaaatattcg | ctatggcaga | 1560 |
| gaagatgcaa | caatggaaga | catagtccaa | gctgccaagg | aggccaatgc | ctacaacttc | 1620 |
| atcatggacc | tgccacagca | atttgacacc | cttgttggag | aaggaggagg | ccagatgagt | 1680 |
| ggtggccaga | aacaaagggt | agctatcgcc | agagccctca | tccgaaatcc | caagattctg | 1740 |
| cttttggaca | tggccaccct | agctctggac | aatgagagtg | aagccatggt | gcaagaagtg | 1800 |
| ctgagtaaga | ttcagcatgg | gcacacaatc | atttcagttg | ctcatcgctt | gtctacggtc | 1860 |
| agagctgcag | ataccatcat | tggttttgaa | catggcactg | cagtggaaag | agggaccca | 1920 |

```
gaagaattac tggaaaggaa aggtgtttac ttcactctag tgactttgca aagccaggga      1980
aatcaagctc ttaatgaaga ggacataaag gatgcaactg aagatgacat gcttgcgagg      2040
acctttagca gagggagcta ccaggatagt ttaagggctt ccatccggca acgctccaag      2100
tctcagcttt cttacctggt gcacgaacct ccattagctg ttgtagatca taagtctacc      2160
tatgaagaag atagaaagga caaggacatt cctgtgcagg aagaagttga acctgcccca      2220
gttaggagga ttctgaaatt cagtgctcca gaatggccct acatgctggt agggtctgtg      2280
ggtgcagctg tgaacgggac agtcacaccc ttgtatgcct ttttattcag ccagattctt      2340
gggactttt caattcctga taagaggaa caaaggtcac agatcaatgg tgtgtgccta       2400
cttttttgtag caatgggctg tgtatctctt ttcacccaat ttctacaggg atatgccttt     2460
gctaaatctg gggagctcct aacaaaaagg ctacgtaaat ttggtttcag ggcaatgctg      2520
gggcaagata ttgcctggtt tgatgacctc agaaatagcc ctggagcatt gacaacaaga      2580
cttgctacag atgcttccca agttcaaggg gctgccggct ctcagatcgg gatgatagtc      2640
aattccttca ctaacgtcac tgtggccatg atcattgcct tctcctttag ctggaagctg      2700
agcctggtca tcttgtgctt cttcccttc ttggctttat caggagccac acagaccagg       2760
atgttgacag gatttgcctc tcgagataag caggccctgg agatggtggg acagattaca      2820
aatgaagccc tcagtaacat ccgcactgtt gctggaattg gaaaggagag gcggttcatt      2880
gaagcacttg agactgagct ggagaagccc ttcaagacag ccattcagaa agccaatatt      2940
tacggattct gctttgcctt tgcccagtgc atcatgttta ttgcgaattc tgcttcctac      3000
agatatggag gttacttaat ctccaatgag gggctccatt tcagctatgt gttcagggtg      3060
atctctgcag ttgtactgag tgcaacagct cttggaagag ccttctctta cacccccaagt    3120
tatgcaaaag ctaaaatatc agctgcacgc ttttttcaac tgctggaccg acaaccccca      3180
atcagtgtat acaatactgc aggtgaaaaa tgggacaact tccagggaa gattgatttt       3240
gttgattgta aatttacata tccttctcga cctgactcgc aagttctgaa tggtctctca      3300
gtgtcgatta gtccagggca gacactggcg tttgttggga gcagtggatg tggcaaaagc      3360
actagcattc agctgttgga acgttttctat gatcctgatc aagggaaggt gatgatagat     3420
ggtcatgaca gcaaaaaagt aaatgtccag ttcctccgct caaacattgg aattgtttcc      3480
caggaaccag tgttgtttgc ctgtagcata atggacaata tcaagtatgg agacaacacc      3540
aaagaaattc ccatggaaag agtcatagca gctgcaaaac aggctcagct gcatgatttt      3600
gtcatgtcac tcccagagaa atatgaaact aacgttgggt cccaggggtc tcaactctct      3660
agaggggaga acaacgcat tgctattgct cgggccattg tacgagatcc taaaatcttg       3720
ctactagatg aagccacttc tgccttagac acagaaagtg aaaagacggt gcaggttgct      3780
ctagacaaag ccagagaggg tcggacctgc attgtcattg cccatcgctt gtccaccatc      3840
cagaacgcgg atatcattgc tgtcatggca caggggtgg tgattgaaaa ggggacccat       3900
gaagaactga tggcccaaaa aggagcctac tacaaactag tcaccactgg atcccccatc      3960
agttga                                                                3966
```